US010125140B1

(12) United States Patent
Purro et al.

(10) Patent No.: US 10,125,140 B1
(45) Date of Patent: Nov. 13, 2018

(54) CRYSTALLINE FORMS OF A BRUTON'S TYROSINE KINASE INHIBITOR

(71) Applicant: Pharmacyclics LLC, Sunnyvale, CA (US)

(72) Inventors: Norbert Purro, Los Gatos, CA (US); Mark S. Smyth, Foster City, CA (US); Erick Goldman, Concord, CA (US); David D. Wirth, Oak Ridge, NC (US)

(73) Assignee: Pharmacyclics LLC, Sunnyvale, CA (US)

( * ) Notice: Subject to any disclaimer, the term of this patent is extended or adjusted under 35 U.S.C. 154(b) by 0 days.

(21) Appl. No.: 16/036,258

(22) Filed: Jul. 16, 2018

Related U.S. Application Data

(60) Continuation of application No. 15/900,660, filed on Feb. 20, 2018, which is a continuation of application No. 15/887,744, filed on Feb. 2, 2018, which is a continuation of application No. 15/645,319, filed on Jul. 10, 2017, which is a continuation of application No. 15/497,896, filed on Apr. 26, 2017, now Pat. No. 9,725,455, which is a continuation of application No. 15/386,118, filed on Dec. 21, 2016, now Pat. No. 9,713,617, which is a division of application No. 14/405,317, filed as application No. PCT/US2013/043888 on Jun. 3, 2013, now Pat. No. 9,540,382.

(60) Provisional application No. 61/655,381, filed on Jun. 4, 2012.

(51) Int. Cl.
| | | |
|---|---|---|
| A61K 31/519 | (2006.01) |
| C07D 487/04 | (2006.01) |
| A61K 9/20 | (2006.01) |
| A61K 45/06 | (2006.01) |
| B65D 75/36 | (2006.01) |
| A61K 9/00 | (2006.01) |
| A61K 9/48 | (2006.01) |
| A61J 1/03 | (2006.01) |

(52) U.S. Cl.
CPC ............ *C07D 487/04* (2013.01); *A61J 1/035* (2013.01); *A61K 9/0053* (2013.01); *A61K 9/2013* (2013.01); *A61K 9/2018* (2013.01); *A61K 9/2054* (2013.01); *A61K 9/4825* (2013.01); *A61K 9/4858* (2013.01); *A61K 9/4866* (2013.01); *A61K 31/519* (2013.01); *A61K 45/06* (2013.01); *B65D 75/36* (2013.01); *C07B 2200/13* (2013.01)

(58) Field of Classification Search
CPC ....................................................... A61K 31/519
USPC ..................................................... 514/258.1
See application file for complete search history.

(56) References Cited

U.S. PATENT DOCUMENTS

| | | |
|---|---|---|
| 4,824,982 A | 4/1989 | Vahlensieck et al. |
| 5,033,252 A | 7/1991 | Carter |
| 5,052,558 A | 10/1991 | Carter |
| 5,145,684 A | 9/1992 | Liversidge et al. |
| 5,323,907 A | 6/1994 | Kalvelage |
| 5,397,787 A | 3/1995 | Buzzetti et al. |
| 5,593,997 A | 1/1997 | Dow et al. |
| 6,160,010 A | 12/2000 | Uckun et al. |
| 6,221,900 B1 | 4/2001 | Uckun et al. |
| 6,303,652 B1 | 10/2001 | Uckun et al. |
| 6,306,897 B1 | 10/2001 | Uckun et al. |
| 6,326,469 B1 | 12/2001 | Ullrich et al. |
| 6,410,054 B1 | 6/2002 | Thosar et al. |
| 6,506,769 B2 | 1/2003 | Snow et al. |
| 6,660,744 B1 | 12/2003 | Hirst et al. |
| 6,753,348 B2 | 6/2004 | Uckun et al. |
| 6,770,639 B2 | 8/2004 | Snow et al. |
| 6,921,763 B2 | 7/2005 | Hirst et al. |
| 7,138,420 B2 | 11/2006 | Bentzien et al. |
| 7,332,497 B2 | 2/2008 | Hirst et al. |
| 7,514,444 B2 | 4/2009 | Honigberg et al. |
| 7,718,662 B1 | 5/2010 | Chen et al. |
| 7,732,454 B2 | 6/2010 | Verner |
| 7,741,330 B1 | 6/2010 | Chen et al. |
| 7,825,118 B2 | 11/2010 | Honigberg et al. |
| 7,960,396 B2 | 6/2011 | Honigberg et al. |
| 8,008,309 B2 | 8/2011 | Honigberg et al. |
| 8,088,781 B2 | 1/2012 | Honigberg et al. |
| 8,124,126 B2 | 2/2012 | Bosse et al. |
| 8,158,786 B2 | 4/2012 | Honigberg et al. |

(Continued)

FOREIGN PATENT DOCUMENTS

| | | |
|---|---|---|
| CN | 101610676 A | 12/2009 |
| CN | 103121999 A | 5/2013 |

(Continued)

OTHER PUBLICATIONS

"Imbruvica," EPAR Summary for the Public, European Medicines Agency Science Medicines Health last updated Aug. 2016, retrieved from: <http://www.ema.europa.eu/ema/index.jsp?curl=pages/medicines/human/medicines/003791/human_med_001801.jsp&mid=WC0b01ac058001d124>.

ACS 2015 (http://www.cancer.org/cancer/non-hodgkinlymphoma/detailedguide/non-hodgkin-lymphoma-types-of-non-hodgkinlymphoma).

(Continued)

*Primary Examiner* — Raymond J Henley, III
(74) *Attorney, Agent, or Firm* — Foley Hoag LLP

(57) ABSTRACT

Described herein is the Bruton's tyrosine kinase (Btk) inhibitor 1-((R)-3-(4-amino-3-(4-phenoxyphenyl)-1H-pyrazolo[3,4-d]pyrimidin-1-yl)piperidin-1-yl)prop-2-en-1-one, including crystalline forms, solvates and pharmaceutically acceptable salts thereof. Also disclosed are pharmaceutical compositions that include the Btk inhibitor, as well as methods of using the Btk inhibitor, alone or in combination with other therapeutic agents, for the treatment of autoimmune diseases or conditions, heteroimmune diseases or conditions, cancer, including lymphoma, and inflammatory diseases or conditions.

4 Claims, 16 Drawing Sheets

(56) References Cited

U.S. PATENT DOCUMENTS

| | | |
|---|---|---|
| 8,232,280 B2 | 7/2012 | Honigberg et al. |
| 8,236,812 B2 | 8/2012 | Honigberg et al. |
| 8,306,897 B2 | 11/2012 | Yolles |
| 8,377,946 B1 | 2/2013 | Chen et al. |
| 8,399,470 B2 | 3/2013 | Honigberg et al. |
| 8,399,471 B2 | 3/2013 | Figueroa Perez et al. |
| 8,476,284 B2 | 7/2013 | Honigberg et al. |
| 8,497,277 B2 | 7/2013 | Honigberg et al. |
| 8,501,724 B1 | 8/2013 | Chen et al. |
| 8,501,751 B2 | 8/2013 | Honigberg et al. |
| 8,552,010 B2 | 10/2013 | Honigberg et al. |
| 8,557,803 B2 | 10/2013 | Yamamoto et al. |
| 8,563,563 B2 | 10/2013 | Honigberg et al. |
| 8,633,311 B2 | 1/2014 | Bommer et al. |
| 8,642,604 B2 | 2/2014 | Knight et al. |
| 8,658,653 B2 | 2/2014 | Honigberg et al. |
| 8,691,546 B2 | 4/2014 | Honigberg et al. |
| 8,697,711 B2 | 4/2014 | Honigberg et al. |
| 8,703,780 B2 | 4/2014 | Honigberg et al. |
| 8,735,403 B2 | 5/2014 | Honigberg et al. |
| 8,735,404 B2 | 5/2014 | Honigberg et al. |
| 8,741,908 B2 | 6/2014 | Honigberg et al. |
| 8,748,438 B2 | 6/2014 | Honigberg et al. |
| 8,748,439 B2 | 6/2014 | Honigberg et al. |
| 8,754,090 B2 | 6/2014 | Buggy et al. |
| 8,754,091 B2 | 6/2014 | Honigberg et al. |
| 8,759,516 B2 | 6/2014 | Honigberg et al. |
| 8,809,273 B2 | 8/2014 | Honigberg et al. |
| 8,883,435 B2 | 11/2014 | Honigberg et al. |
| 8,883,803 B2 | 11/2014 | Honigberg et al. |
| 8,940,750 B2 | 1/2015 | Honigberg et al. |
| 8,952,015 B2 | 2/2015 | Honigberg et al. |
| 8,957,079 B2 | 2/2015 | Honigberg et al. |
| 8,975,266 B2 | 3/2015 | Honigberg et al. |
| 8,987,233 B2 | 3/2015 | Pan et al. |
| 8,999,999 B2 | 4/2015 | Buggy et al. |
| 9,012,463 B2 | 4/2015 | Chen et al. |
| 9,079,908 B2 | 7/2015 | Honigberg et al. |
| 9,107,924 B2 | 8/2015 | Buggy et al. |
| 9,117,924 B2 | 8/2015 | Kitagawa et al. |
| 9,125,889 B2 | 9/2015 | Buggy et al. |
| 9,127,012 B2 | 9/2015 | Honigberg et al. |
| 9,127,069 B1 | 9/2015 | Tabuteau |
| 9,133,198 B2 | 9/2015 | Honigberg et al. |
| 9,133,201 B2 | 9/2015 | Honigberg et al. |
| 9,133,202 B2 | 9/2015 | Honigberg et al. |
| 9,139,591 B2 | 9/2015 | Honigberg et al. |
| 9,181,257 B2 | 11/2015 | Honigberg et al. |
| 9,181,263 B2 | 11/2015 | Honigberg et al. |
| 9,193,735 B2 | 11/2015 | Honigberg et al. |
| 9,206,189 B2 | 12/2015 | Honigberg et al. |
| 9,212,185 B2 | 12/2015 | Honigberg et al. |
| 9,266,893 B2 | 2/2016 | Honigberg et al. |
| 9,273,051 B2 | 3/2016 | Chen et al. |
| 9,278,100 B2 | 3/2016 | Honigberg et al. |
| 9,296,753 B2 | 3/2016 | Smyth et al. |
| 9,409,911 B2 | 8/2016 | Honigberg et al. |
| 9,540,382 B2 | 1/2017 | Purro et al. |
| 9,545,407 B2 | 1/2017 | Shu et al. |
| 9,655,857 B2 | 5/2017 | Chong et al. |
| 9,713,617 B2 | 7/2017 | Purro et al. |
| 9,725,455 B1 | 8/2017 | Purro et al. |
| 9,828,383 B1 | 11/2017 | Purro et al. |
| 10,010,507 B1 | 7/2018 | Chong et al. |
| 2002/0016460 A1 | 2/2002 | Snow et al. |
| 2002/0155505 A1 | 10/2002 | Wells et al. |
| 2003/0013125 A1 | 1/2003 | Braisted et al. |
| 2003/0035833 A1 | 2/2003 | He |
| 2003/0040461 A1 | 2/2003 | McAtee |
| 2003/0118078 A1 | 6/2003 | Carlson et al. |
| 2003/0125235 A1 | 7/2003 | Foxwell |
| 2003/0225144 A1 | 12/2003 | Woodward et al. |
| 2004/0006083 A1 | 1/2004 | Hirst et al. |
| 2005/0008640 A1 | 1/2005 | Waegell et al. |
| 2005/0084905 A1 | 4/2005 | Prescott et al. |
| 2005/0090499 A1 | 4/2005 | Currie et al. |
| 2005/0101604 A1 | 5/2005 | Currie et al. |
| 2005/0153990 A1 | 7/2005 | Watkins |
| 2005/0196851 A1 | 9/2005 | Uckun |
| 2005/0209255 A1 | 9/2005 | Jimenez et al. |
| 2006/0079494 A1 | 4/2006 | Santi et al. |
| 2006/0167090 A1 | 7/2006 | Uckun et al. |
| 2007/0065449 A1 | 3/2007 | Verschraegen |
| 2007/0105136 A1 | 5/2007 | Staudt et al. |
| 2007/0281907 A1 | 12/2007 | Watkins |
| 2008/0076921 A1 | 3/2008 | Honigberg et al. |
| 2008/0108636 A1 | 5/2008 | Honigberg et al. |
| 2008/0214501 A1 | 9/2008 | Pan et al. |
| 2008/0242707 A1 | 10/2008 | Schuckler et al. |
| 2009/0010911 A1 | 1/2009 | Andreotti et al. |
| 2009/0105209 A1 | 4/2009 | Dewdney et al. |
| 2009/0186898 A1 | 7/2009 | Dewdney et al. |
| 2009/0317836 A1 | 12/2009 | Kuhn et al. |
| 2010/0022561 A1 | 1/2010 | Honigberg et al. |
| 2010/0041677 A1 | 2/2010 | Honigberg et al. |
| 2010/0254905 A1 | 10/2010 | Honigberg et al. |
| 2010/0324050 A1 | 12/2010 | Honigberg et al. |
| 2011/0039868 A1 | 2/2011 | Honigberg et al. |
| 2011/0086866 A1 | 4/2011 | Chen et al. |
| 2011/0160273 A1 | 6/2011 | Buschmann et al. |
| 2011/0177011 A1 | 7/2011 | Currie et al. |
| 2011/0224235 A1 | 9/2011 | Honigberg et al. |
| 2011/0281322 A1 | 11/2011 | Honigberg et al. |
| 2012/0065201 A1 | 3/2012 | Honigberg et al. |
| 2012/0071497 A1 | 3/2012 | Buggy et al. |
| 2012/0087915 A1 | 4/2012 | Buggy et al. |
| 2012/0088912 A1 | 4/2012 | Honigberg et al. |
| 2012/0095026 A1 | 4/2012 | Honigberg et al. |
| 2012/0100138 A1 | 4/2012 | Buggy et al. |
| 2012/0101113 A1 | 4/2012 | Honigberg et al. |
| 2012/0101114 A1 | 4/2012 | Honigberg et al. |
| 2012/0108547 A1 | 5/2012 | Jankowski et al. |
| 2012/0108612 A1 | 5/2012 | Honigberg et al. |
| 2012/0115889 A1 | 5/2012 | Honigberg et al. |
| 2012/0122894 A1 | 5/2012 | Honigberg et al. |
| 2012/0129821 A1 | 5/2012 | Honigberg et al. |
| 2012/0129873 A1 | 5/2012 | Honigberg et al. |
| 2012/0135944 A1 | 5/2012 | Honigberg et al. |
| 2012/0165328 A1 | 6/2012 | Honigberg et al. |
| 2012/0178753 A1 | 7/2012 | Honigberg et al. |
| 2012/0183535 A1 | 7/2012 | Buggy et al. |
| 2012/0184013 A1 | 7/2012 | Honigberg et al. |
| 2012/0184567 A1 | 7/2012 | Honigberg et al. |
| 2012/0202264 A1 | 8/2012 | Honigberg et al. |
| 2012/0214826 A1 | 8/2012 | Honigberg et al. |
| 2012/0238733 A1 | 9/2012 | Vasudevan et al. |
| 2012/0252821 A1 | 10/2012 | Honigberg et al. |
| 2012/0252822 A1 | 10/2012 | Honigberg et al. |
| 2012/0277177 A1 | 11/2012 | Amparo et al. |
| 2012/0277225 A1 | 11/2012 | Honigberg et al. |
| 2012/0277254 A1 | 11/2012 | Honigberg et al. |
| 2012/0277255 A1 | 11/2012 | Honigberg et al. |
| 2012/0283276 A1 | 11/2012 | Honigberg et al. |
| 2012/0283277 A1 | 11/2012 | Honigberg et al. |
| 2012/0296089 A1 | 11/2012 | Honigberg et al. |
| 2012/0328679 A1 | 12/2012 | Curatolo et al. |
| 2012/0329130 A1 | 12/2012 | Honigberg et al. |
| 2013/0005745 A1 | 1/2013 | Honigberg et al. |
| 2013/0005746 A1 | 1/2013 | Honigberg et al. |
| 2013/0012525 A1 | 1/2013 | Honigberg et al. |
| 2013/0018060 A1 | 1/2013 | Honigberg et al. |
| 2013/0035334 A1 | 2/2013 | Honigberg et al. |
| 2013/0079327 A1 | 3/2013 | Yamamoto et al. |
| 2013/0172314 A1 | 7/2013 | Chen et al. |
| 2013/0195852 A1 | 8/2013 | Buggy et al. |
| 2013/0202611 A1 | 8/2013 | Buggy et al. |
| 2013/0273030 A1 | 10/2013 | Buggy et al. |
| 2013/0310402 A1 | 11/2013 | Buggy et al. |
| 2013/0338172 A1 | 12/2013 | Smyth et al. |
| 2014/0039186 A1 | 2/2014 | Honigberg et al. |
| 2014/0057907 A1 | 2/2014 | Honigberg et al. |
| 2014/0079690 A1 | 3/2014 | Buggy et al. |
| 2014/0080844 A1 | 3/2014 | Chen et al. |
| 2014/0088116 A1 | 3/2014 | Morales Rojas et al. |

(56) References Cited

U.S. PATENT DOCUMENTS

| | | |
|---|---|---|
| 2014/0128413 A1 | 5/2014 | Honigberg et al. |
| 2014/0128414 A1 | 5/2014 | Honigberg et al. |
| 2014/0135347 A1 | 5/2014 | Honigberg et al. |
| 2014/0142123 A1 | 5/2014 | Honigberg et al. |
| 2014/0163027 A1 | 6/2014 | Verner et al. |
| 2014/0163046 A1 | 6/2014 | Honigberg et al. |
| 2014/0171453 A1 | 6/2014 | Honigberg et al. |
| 2014/0187564 A1 | 7/2014 | Honigberg et al. |
| 2014/0187565 A1 | 7/2014 | Honigberg et al. |
| 2014/0194446 A1 | 7/2014 | Buggy et al. |
| 2014/0212485 A1 | 7/2014 | Honigberg et al. |
| 2014/0243355 A1 | 8/2014 | Honigberg et al. |
| 2014/0288037 A1 | 9/2014 | Casebier et al. |
| 2014/0336203 A1 | 11/2014 | Smyth et al. |
| 2014/0336206 A1 | 11/2014 | Honigberg et al. |
| 2014/0377258 A1 | 12/2014 | Stern et al. |
| 2014/0378446 A1 | 12/2014 | Chen et al. |
| 2015/0018336 A1 | 1/2015 | Chen et al. |
| 2015/0031710 A1 | 1/2015 | Buggy et al. |
| 2015/0031711 A1 | 1/2015 | Buggy et al. |
| 2015/0038518 A1 | 2/2015 | Balasubramanian |
| 2015/0110871 A1 | 4/2015 | Wong |
| 2015/0118222 A1 | 4/2015 | Levy et al. |
| 2015/0133661 A1 | 5/2015 | Honigberg et al. |
| 2015/0152115 A1 | 6/2015 | Honigberg et al. |
| 2015/0158871 A1 | 6/2015 | Purro et al. |
| 2015/0224060 A1 | 8/2015 | Wong |
| 2015/0231077 A1 | 8/2015 | Egusa et al. |
| 2015/0238490 A1 | 8/2015 | Burger |
| 2015/0239897 A1 | 8/2015 | Chen et al. |
| 2015/0265618 A1 | 9/2015 | Honigberg et al. |
| 2015/0267261 A1 | 9/2015 | Byrd et al. |
| 2015/0267752 A1 | 9/2015 | Navarro |
| 2015/0306103 A1 | 10/2015 | Honigberg et al. |
| 2015/0306106 A1 | 10/2015 | Honigberg et al. |
| 2015/0307500 A1 | 10/2015 | Honigberg et al. |
| 2016/0000792 A1 | 1/2016 | Buggy et al. |
| 2016/0008777 A1 | 1/2016 | Patel et al. |
| 2016/0067241 A1 | 3/2016 | Brown |
| 2016/0243033 A1 | 8/2016 | Buggy et al. |
| 2016/0287594 A1 | 10/2016 | Gupta et al. |
| 2017/0002009 A1 | 1/2017 | Chen et al. |
| 2017/0079981 A1 | 3/2017 | Atluri et al. |
| 2017/0226114 A1 | 8/2017 | Cohen et al. |
| 2017/0258729 A1 | 9/2017 | Chong et al. |
| 2017/0305919 A1 | 10/2017 | Purro et al. |
| 2018/0028537 A1 | 2/2018 | Atluri et al. |
| 2018/0072738 A1 | 3/2018 | Goldman et al. |
| 2018/0072739 A1 | 3/2018 | Goldman et al. |
| 2018/0155352 A1 | 6/2018 | Purro et al. |
| 2018/0170940 A1 | 6/2018 | Purro et al. |
| 2018/0179214 A1 | 6/2018 | Purro et al. |
| 2018/0179215 A1 | 6/2018 | Purro et al. |

FOREIGN PATENT DOCUMENTS

| | | |
|---|---|---|
| CN | 103923084 A | 7/2014 |
| CN | 104523695 A | 4/2015 |
| CN | 105085529 A | 11/2015 |
| CN | 105294696 A | 2/2016 |
| CN | 105440040 A | 3/2016 |
| CN | 105640961 A | 6/2016 |
| CN | 105646484 A | 6/2016 |
| CN | 105646498 A | 6/2016 |
| CN | 105646499 A | 6/2016 |
| CN | 106619643 A | 5/2017 |
| EP | 1473039 A1 | 11/2004 |
| JP | 2010504324 A | 2/2010 |
| JP | 2010535232 A | 11/2010 |
| JP | 5841998 B2 | 1/2016 |
| WO | WO-1997/028161 A1 | 8/1997 |
| WO | WO-1997/049706 A1 | 12/1997 |
| WO | WO-1998/041525 A1 | 9/1998 |
| WO | WO-1999/054286 A2 | 10/1999 |
| WO | WO-2000/000823 | 1/2000 |
| WO | WO-2000/056737 A2 | 9/2000 |
| WO | WO-2001/019829 A2 | 3/2001 |
| WO | WO-2001/019829 A3 | 3/2001 |
| WO | WO-2001/025238 A2 | 4/2001 |
| WO | WO-2001/041754 | 6/2001 |
| WO | WO-2001/044258 A1 | 6/2001 |
| WO | WO-2002/038797 A2 | 5/2002 |
| WO | WO-2002/38797 A2 | 5/2002 |
| WO | WO-2002/076986 A1 | 10/2002 |
| WO | WO-2002/080926 | 10/2002 |
| WO | WO-2003/000187 | 1/2003 |
| WO | WO-2003/013540 | 2/2003 |
| WO | WO-2003/046200 | 6/2003 |
| WO | WO-2003/097645 | 11/2003 |
| WO | WO-2004/074290 A1 | 9/2004 |
| WO | WO-2004/096253 A1 | 11/2004 |
| WO | WO-2004/100868 A2 | 11/2004 |
| WO | WO-2004/100868 A3 | 11/2004 |
| WO | WO-2005/000197 A2 | 1/2005 |
| WO | WO-2005/005429 A1 | 1/2005 |
| WO | WO-2005/014599 A1 | 2/2005 |
| WO | WO-2005/037836 A2 | 4/2005 |
| WO | WO-2005/037843 A1 | 4/2005 |
| WO | WO-2005/060956 A1 | 7/2005 |
| WO | WO-2005/074603 A2 | 8/2005 |
| WO | WO-2006/002871 A1 | 1/2006 |
| WO | WO-2006/012422 A1 | 2/2006 |
| WO | WO-2006/036527 A1 | 4/2006 |
| WO | WO-2006/050946 A1 | 5/2006 |
| WO | WO-2006/053121 A2 | 5/2006 |
| WO | WO-2006/099075 A2 | 9/2006 |
| WO | WO-2006/124462 A2 | 11/2006 |
| WO | WO-2007/002325 A1 | 1/2007 |
| WO | WO-2007/058832 A2 | 5/2007 |
| WO | WO-2007/087068 A2 | 8/2007 |
| WO | WO-2007/136790 A2 | 11/2007 |
| WO | WO-2008/039218 A2 | 4/2008 |
| WO | WO-2008/054827 A2 | 5/2008 |
| WO | WO-2008/108636 A1 | 9/2008 |
| WO | WO-2008/121742 A2 | 10/2008 |
| WO | WO-2009/018233 A1 | 2/2009 |
| WO | WO-2009/051822 A1 | 4/2009 |
| WO | WO-2009/129246 A2 | 10/2009 |
| WO | WO-2009/158571 A1 | 12/2009 |
| WO | WO-2010/009342 A2 | 1/2010 |
| WO | WO-2010/009342 A3 | 1/2010 |
| WO | WO-2010/065898 A2 | 6/2010 |
| WO | WO-2010/0068806 A1 | 6/2010 |
| WO | WO-2010/126960 A1 | 11/2010 |
| WO | WO-2011/034907 A2 | 3/2011 |
| WO | WO-2011046964 A2 | 4/2011 |
| WO | WO-2011/152351 A1 | 12/2011 |
| WO | WO-2011/153514 A2 | 12/2011 |
| WO | WO-2011/162515 A2 | 12/2011 |
| WO | WO-2012/021444 A1 | 2/2012 |
| WO | WO-2012/158764 A1 | 11/2012 |
| WO | WO-2013105894 A1 | 7/2013 |
| WO | WO-2013/184572 A1 | 12/2013 |
| WO | WO-2013191965 A1 | 12/2013 |
| WO | WO-2014/004707 A1 | 1/2014 |
| WO | WO-2014/018567 A1 | 1/2014 |
| WO | WO-2015/034478 A1 | 3/2015 |
| WO | WO-2015/038887 A1 | 3/2015 |
| WO | WO-2015071432 A1 | 5/2015 |
| WO | WO-2015081180 A1 | 6/2015 |
| WO | WO-2015/095772 A2 | 6/2015 |
| WO | WO-2015120110 A2 | 8/2015 |
| WO | WO-2015/145415 A2 | 10/2015 |
| WO | WO-2016/022942 A1 | 2/2016 |
| WO | WO-2016/025720 A1 | 2/2016 |
| WO | WO-2016016665 A1 | 2/2016 |
| WO | WO-2016020697 A1 | 2/2016 |
| WO | WO-2016/050422 A1 | 4/2016 |
| WO | WO-201679216 A1 | 5/2016 |
| WO | WO-2016127960 A1 | 8/2016 |
| WO | WO-2016/141068 A1 | 9/2016 |
| WO | WO-2016139588 A1 | 9/2016 |
| WO | WO-2016/160598 A1 | 10/2016 |
| WO | WO-2016/160604 A1 | 10/2016 |

(56) References Cited

FOREIGN PATENT DOCUMENTS

| WO | WO-2016156127 A1 | 10/2016 |
|----|------------------|---------|
| WO | WO-2017/125423 A1 | 7/2017 |
| WO | WO-2017/125424 A1 | 7/2017 |

OTHER PUBLICATIONS

Advani et al. Effect of Btk inhibitor PCI-32765 monotherapy on responses in patients with relapsed aggressive NHL: Evidence of antitumor activity from a phase I study. J. Clin. Oncol., 2010 ASCO Annual Meeting Proceedings (Post-Meeting Edition), 28(15 Supp):8012 (2010).
Advani et al., "The Btk inhibitor PCI-32765 is highly active and well tolerated in patients (PTS) with relapsed/refractory B cell malignancies: final results from a phase I study," Ann Oncol, 22(Supp 4):abstract 153 (2011).
Advani, R.H., et al., 2013, "Bruton tyrosine kinase inhibitor Ibrutinib (PCI-32765) ha significant activity in patients with relapsed/refractory B-cell malignancies", Journal of Clinical Oncology, vol. 31, No. 1 ,pp. 88-94.
Agathocleous et al. Preliminary Results of a Phase I/II Study of Weekly or Twice Weekly Bortezomib in Combination with Rituximab, in Patients with Follicular Lymphoma, Mantle Cell Lymphoma and Waldenstrom's Macroglobulinaemia. Blood (ASH Annual Meeting Abstracts) 110:Abstract 2559 (2007).
Agency for Toxic Substances and Disease Registry, Public Health Assessment Guidance Manual, (2005).
Ahn et al. Michael acceptors as a tool for anticancer drug design. Current Pharmaceutical Design 2(3):247-262 (1996).
Apsel et al. Targeted Polypharmacology: Discovery of Dual Inhibitors of Tyrosine and Phosphoinositide Kinases. Nature Chem. Bio., 4(11):691-699 (2008).
Arnold et al. Pyrrolo[2,3-d]pyrimidines Containing an Extended 5-Substituent as Potent and Selective Inhibitors of Ick 1. Bioorg. Med. Chem. Ltrs. 10:2167-2170 (2000).
Banker et al. Modern Pharmaceutics, 3ed., Marcel Dekker, New York 1996, p. 596.
Bernstein, "Polymorphism—A Perspective," Crystal Growth & Design, 11: 632-650 (2011).
Bharate S.S., et al., "Incompatibilities of Pharmaceutical Excipients with Active Pharmaceutical Ingredients: A Comprehensive Review", Journal of Excipients and Food Chemicals, 2010, vol. 1 (3), pp. 3-26.
Biospace, 20091208, pharmacyclics, Inc. (PCYC) announces presentation of interim results from phase I trial of its first-in-human btk inhibitor PCI-32765.
Brown et al., "Phase lb trial of AVL-292, a covalent inhibitor of Bruton's tyrosine kinase (Btk), in chronic lymphocytic leukemia (CLL) and B-non-Hodgkin lymphoma (B-NHL)," J Clin Oncol, 30(supp):abstract 8032 (2012); [online][retrieved on Jan. 14, 2016] Retrieved from the Internet: <http://meetinglibrary.asco.org/content/98841-114>.
Browning. B cells move to centre stage: novel opportunities for autoimmune disease treatment. Nature Reviews/Drug Discovery 5:564-576 (Jul. 2006).
Burchat et al. Pyrazolo[3,4-d]pyrimidines Containing an Extended 3-Substituent as Potent Inhibitors of Lck—a Selectivity Insight. Bioorg. Med. Chem. Ltrs. 12:1687-1690 (2002).
Burger et al. CXCR4 antagonists: targeting the microenvironment in leukemia and other cancers, Leukemia 23:43-52 (2009).
Burger et al. High-Level Expression of the T-Cell Chemokines CCL3 and CCL4 by Chronic Lymphocytic Leukemia B Cells in Nurselike Cell Cocultures and After BCR Stimulation. Blood 113(13):3050-3058 (2008).
Burger. Targeting the microenvironment in chronic lymphocytic leukemia is changing the therapeutic landscape. Curr. Opin. Oncol. 24(6):643-649 (Epub Sep. 6, 2012/Nov. 2012).

Byrd et al. Entering the era of targeted therapy for chronic lymphocytic leukemia: Impact on the practicing clinician. J. Clinical Oncology (Jul. 21, 2014) (pii: JCO.2014.55.8262).
Byrd et al. Targeting BTK with Ibrutinib in relapsed chronic lymphocytic leukemia, NEJM 369(1):32-42 (Jul. 4, 2013).
Byrd J.C., et al., "Three-year follow-up of treatment-naïve and previously treated patients with CLL and SLL receiving single-agent ibrutinib", Blood, Apr. 16, 2015, vol. 125 (16), pp. 2497-2506.
Byrn et al., "Pharmaceutical Solids: A Strategic Approach to Regulatory Considerations," Pharmaceutical Research, 12: 945-954 (1995).
Calderwood et al., "Pyrrolo[2,3-d]pyrimidines Containing Diverse N-7 Substituents as Potent Inhibitors of Lcks," Bioorg Med Chem Lett, 12: 1683-1686 (2002).
Cameron F., et al., "Ibrutinib: first global approval," Drugs, Feb. 2014, vol. 74 (2), pp. 263-271.
Cannon. Chapter Nineteen in Burger's Medicinal Chemistry and Drug Discovery, Fifth Edition, vol. 1: Principles and Practice, Wiley-Interscience 1995, pp. 783-802.
Carmi et al. Clinical perspectives for irreversible tyrosine kinase inhibitors in cancer. Biochem. Pharmacol. (Epub Aug. 4, 2012) 84(11):1388-1399 (Dec. 2012).
Carrle et al. Current Strategies of Chemotherapy in Osteosarcoma. International Orthopaedics 30:445-451 (2006).
Certified Translation of CN103121999A, dated Sep. 29, 2016.
Certified Translation of CN103923084A, dated Sep. 29, 2016.
Certified Translation of CN103923084B, dated Sep. 29, 2016.
Certified Translation of CN104523695A, dated Nov. 14, 2016.
Chang et al. Egress of CD19+CD5+ cells into peripheral blood following treatment with the Bruton tyrosine kinase inhibitor inbrutinib in mantel cell lymphoma patients. Blood, 122:2412-2424 (2013).
Chang et al., "PCI-45292, a novel Btk inhibitor with optimized pharmaceutical properties, demonstrates potent activities in rodent models of arthritis," ACR/ARHP Scientific Meeting, Poster #286 (2010).
Chang et al., "The Bruton tyrosine kinase inhibitor PCI-32765 ameliorates autoimmune arthritis by inhibition of multiple effector cells," Arhtritis Res Ther, 13:R115 (2011).
Chavez et al. Ibrutinib: An Evidence-Based Review of Its Potential in the Treatment of Advanced Chronic Lymphocytic Leukemia. Core Evidence 8:37-45 (2013).
Chen et al. SYK-dependent tonic B-cell receptor signaling is a rational treatment target in diffuse large B-cell lymphoma. Blood 111(4):2230-2237 (2008) [E-pub Nov. 15, 2007].
Ciric et al., "Clonal Evolution in Waldenstrom macroglobulinemia Highlights Functional Role of B-Cell Receptor," Blood, 97: 321-323 (2001).
Cohen et al. Structural Bioinformatics-Based Design of Selective, Irreversible Kinase Inhibitors. Science 308:1318-1321 (May 27, 2005).
Czuczman et al. Rituximab in combination with fludarabine chemotherapy in low-grade or follicular lymphoma. J. Clin. Oncol. 23(4):694-704 (Feb. 1, 2005).
D'Cruz et al. Novel Bruton's tyrosine kinase inhibitors currently in development. OncoTargets and Therapy 6:161-176 (2013).
Dana-Farber Cancer Institute. A Phase II Study of Ibrutinib Plus FCR in Previously Untreated, Younger Patients With Chronic Lymphocytic Leukemia (iFCR). In: ClinicalTrials.gov [Internet]. Bethesda (MD): National Library of Medicine (US). Sep. 23, 2014 [cited Feb. 5, 2015] Available from: https://clinicaltrial.gov/ct2/show/NCT02251548?term=NCT02251548 NLM Identifier: NCT02251548.
Dana-Farber Cancer Institute. Ibrutinib (PCI-32765) in Waldenstrom's Macroglobulinemia. In: ClinicalTrials.gov [Internet]. Bethesda (MD): National Library of Medicine (US). May 17, 2012—[cited Nov. 22, 2013]. Available from: http://clinicaltrials.gov/ct2/show/NCT01614821 NLM Identifier: NCT01614821.
Davids et al. Targeting the B Cell Receptor Pathway in Chronic Lymphocytic Leukemia. Leuk. Lymphoma (Epub May 23, 2012), 53(12):2362-2370 (Dec. 2012).
Davis et al. Chronic active B-cell receptor signalling in diffuse large B-cell lymphoma. Nature 463(7277):88-94 (2010).
Desiderio. Role of Btk in B cell development and signaling. Curr. Op. in Immunology 1997, 9:534-540.

(56) References Cited

OTHER PUBLICATIONS

Devos et al., "The Bruton's tyrosine kinase (BTK) inhibitor, ibrutinib (PCI-32765), has preferential activity in the activated B cell-like (ABC) subtype of relapsed/refractory (RR) DLBCL: interim phase 2 results," Haematologica 98(s1):490 (2013).
Dias et al. Ibrutinib: A New Frontier in the Treatment of Chronic Lymphocytic Leukemia by Bruton's Tyrosine Kinase Inhibition. Cardiovascular & Hematological Agents in Medicinal Chemistry 11:265-271 (2013).
Dorwald, F.Z., "Side Reactions in Organic Synthesis," Wiley:VCH, Weinheim p. IX of Preface, Wiley-VCH Verlag GmbH & C KGaA (2005).
EA200901313 Notification of Office Action dated Oct. 31, 2011.
EA201000599 Search Report dated Nov. 15, 2010.
Edwards. BTK inhibition in myeloma: targeting the seed and the soil. Blood 120(9):1757-1759 (Aug. 2012).
EP 06850039.6 Search Report and Written Opinion dated Feb. 15, 2010.
EP 06850386.1 Search Report and Written Opinion dated Sep. 10, 2010.
EP 08744513.6 Examination Report dated Jan. 16, 2013.
EP 08744513.6 Search Report and Written Opinion dated Mar. 18, 2010.
EP 09798770.5 Search Report and Written Opinion dated Oct. 28, 2011.
EP 10155834.4 Search Report and Written Opinion dated May 27, 2010.
EP 10823966 Supplementary European Search Report dated Oct. 17, 2011.
EP 10823966.6 Search Report dated Oct. 17, 2011.
EP 10823966.6 Written Opinion dated Dec. 6, 2011.
EP 12151943.3 Examination Report dated Feb. 5, 2013.
EP 12151943.3 Search Report and Written Opinion dated Mar. 13, 2012.
EP 12166295.1 Search Report and Written Opinion dated Nov. 6, 2012.
EP 12166296.9 Search Report and Written Opinion dated Nov. 8, 2012.
EP 12166298.5 Search Report and Written Opinion dated Nov. 7, 2012.
EP 12166300.9 Search Report and Written Opinion dated Oct. 31, 2012.
EP 12166301.7 Search Report and Written Opinion dated Nov. 6, 2012.
EP 12166302.5 Search Report and Written Opinion dated Nov. 6, 2012.
EP 12166305.8 Examination Report dated Dec. 3, 2013.
EP 12166305.8 Search Report and Written Opinion dated Nov. 6, 2012.
EP 12166306.6 Search Report and Written Opinion dated Nov. 8, 2012.
EP 12172840.6 Search Report and Written Opinion dated Dec. 12, 2012.
EP 12172841.4 Search Report and Written Opinion dated Jan. 2, 2013.
EP 12172842.2 Extended Search Report dated May 14, 2013.
EP 12172842.2 Partial Search Report dated Jan. 24, 2013.
EP 12172843.0 Search Report and Written Opinion dated Jan. 18, 2013.
EP06850039 Supplemental Search Report dated Feb. 15, 2010.
EP06850039 Supplemental Search Report dated Feb. 9, 2010.
EP11790524.0 Extended European Search Report dated Oct. 9, 2013.
EP12172840.6 Office Action dated Jun. 12, 2014.
EP12172841.4 Office action dated Jun. 12, 2014.
EP12172842.2 Office Action dated Jul. 1, 2014.
EP12172843.0 Office action dated Jul. 1, 2014.
EP15170739.5 Extended European Search Report, dated Nov. 10, 2015.
Extended European Search Report for EP Application No. 16759417 dated Jun. 29, 2018.
Fabian et al. A small molecule-kinase interaction map for clinical kinase inhibitors. Nature Biotechnology, 23(3): 329-336 (2005).
FDA, International Conference on Harmonisation of Technical Requirements for Registration of Pharmaceuticals for Human Use (ICH), Federal Register of Nov. 25, 1997, draft of "Q6A Specifications: Test Procedures and Acceptance Criteria for New Drug Substances and New Drug Products: Chemical Substances." endorsed final guidance Oct. 6, 1999.
Federal Drug Administration, Draft Guidance for Industry, ANDAs: Pharmaceutical Solid Polymorphism at 3 (Dec. 2004).
Fedorak et al. A novel colon-specific steroid prodrug enhances sodium chloride absorption in rat colitis. Am. J. Physiol. 269:G210-218 (1995).
Fisher et al. Prolonged disease-free survival in Hodgkin's disease with MOPP reinduction after first relapse. Ann. Intern. Med., 90(5):761-763 (1979).
Fowler et al., "The Bruton's tyrosine kinase inhibitor ibrutinib (PCI-32765) is active and tolerated in relapsed follicular lymphoma," 54th American Society of Hematology Annual Meeting and Exposition, Abstract 156 (2012).
Friedberg et al. Inhibition of Syk with fostamatinib disodium has significant clinical activity in non-Hodgkin lymphoma and chronic lymphocytic leukemia. Blood 115(13):2578-2585 (2010) [E-pub Nov. 17, 2009].
Fruman. Xid-like Phenotypes: A B Cell Signalosome Takes Shape. Immunity 13:1-3 (Jul. 2000).
Fry et al., "Specific Irreversible Inactivation of the Epidermal Growth Factor Receptor and erbB2, by a New Class of Tyrosine Kinase Inhibitor," Proc Natl Acad Sci, 95: 12022-12027 (1998).
Gazitt et al. Differential mobilization of CD34+ Cells and lymphoma cells in non-Hodgkin's lymphoma patients mobilized with different growth factors, J of Hematotherapy & Stem Cell Research 10:167-176 (2001).
Ghia. Ibrutinib: better combined with other drugs? Lancet 15:1043-1044 (2014).
Giuliani. Multiple myeloma bone disease: pathophysiology of osteoblast inhibition. Blood (Epub Aug. 17, 2006) 108(13):3992-3996 (2006).
Glassman et al., "The value of fluorescence in situ hybridization in the diagnosis and prognosis of chronic lymphocytic leukemia," Cancer Genet Cytogen, 158:88-91 (2005).
Gold. To make antibodies or not:signaling by the B-cell antigen receptor. Trends in Pharmacological Sciences, 23(7):316-324 (Jul. 2002).
Gordon et al. Somatic hypermutation of the B cell receptor genes B29 (Igb, CD79b) and mb1 (Iga, CD79a). PNAS 100(7):4126-4131 (2003).
Groshock et al. Molecular Target Class Is Predictive of In vitro Response Profile. Cancer Res. 70:3677-3686 (2010).
Gu et al., "Polymorph Screening: Influence of Solvent on the Rate of Solvent-Mediated Polymorphic Transformation," Journal of Pharmaceutical Sciences 90, 11: 1878-1890 (2001).
Hagemeister. Rituximab for the treatment of non-Hodgkin's lymphoma and chronic lymphocytic leukaemia. Drugs 70(3):261-272 (2010).
Haleblian and McCrone,"Pharmaceutical Applications of Polymorphism," 58(8): 911-929 (1969).
Hantschel et al. The Btk Tyrosine Kinase is a Major Target of the Bcr-Abl Inhibitor Dasatinib. PNAS 104(33):13283-13288 (2007).
Hata et al. Bruton's tyrosine kinase-mediated Interleukin-2 gene activation in mast cells. J. Biol. Chem. 273(18): 10979-10987 (1998).
Herman et al. Bruton tyrosine kinase represents a promising therapeutic target for treatment of chronic lymphocytic leukemia and is effectively targeted by PCI-32765. Blood (Epub Mar. 21, 2011), 117(23):6287-6296 (Jun. 2011).
Hiddeman et al. Rituximab Plus Chemotherapy in Follicular and Mantle Cell Lymphomas, Seminars in Oncology 30(1)Suppl.2:16-20 (Feb. 2003).
Hiddeman et al., "Frontline therapy with rituximab added to the combination of cyclophosphamide, doxorubicin, vincristine, and prednisone (CHOP) significantly improves the outcome for patients

(56) References Cited

OTHER PUBLICATIONS with advanced-stage follicular lymphoma compared with therapy with CHOP alone: results of a prospective randomized study of the German low-grade lymphoma study group," Blood, 106(12):3725-32 (2005).

Higuchi et al. Pro-drugs as Novel Delivery Systems, vol. 14 of the A.C.S. Symposium Series (1975).

Hochhaus et al. A selective HPLC/RIA for dexamethasone and its prodrug dexamethasone-21-sulphobenzoate sodium in biological fluids. Biomed. Chrom., 6:283-286 (1992).

Honigberg et al. Targeting Btk in lymphoma: PCI-32765 inhibits tumor growth in mouse lymphoma models and a fluorescent analog of PCI-32765 is an active-site probe that enables assessment of Btk inhibition in vivo. ASH Annual Meeting Abstracts 1592. 110(11): 475A (2007).

Honigberg et al., "The Bruton Tyrosine Kinase Inhibitor PCI-32765 Blocks B-Cell Activation and is Efficacious in Models of Autoimmune Disease and B-Cell Malignancy," PNAS USA, 107: 13075-13080 (2010).

Horwood et al. Bruton's Tyrosine Kinase Is Required for Lipopolysaccharide-induced Tumor Necrosis Factor α Production. J. Exp. Med. 197(12):1603-1611 (Jun. 2003).

http://www.uspto.gov/web/offices/pac/dapp/1pecba.htm#7, last accessed Feb. 16, 2011.

Huhn et al. Rituximab therapy of patients with B-cell chronic lymphocytic leukemia. Blood 98(5):1326-1331 (Sep. 1, 2001).

International Search Report and Written Opinion for Application No. PCT/US2016/020467, dated May 23, 2016, 10 pages.

International Search Report for International Application No. PCT/US2006/049626 dated Apr. 9, 2008.

International Search Report for International Application No. PCT/US2009/050897 dated Mar. 15, 2010.

International Search Report for International Application No. PCT/US2016/024305 dated Jun. 27, 2016.

International Search Report for International Application No. PCT/US2016/024321 dated Jun. 28, 2016.

Iqbal et al., on pp. 2-4 (Molecular Biology International, 2014, Article ID 852748, 9 pages.

Iwaki et al. Btk Plays a Crucial Role in the Amplification of FceRI-mediated Mast Cell Activation by Kit. J. Biol. Chem. 280(48):40261-40270 (Dec. 2, 2005).

Jaffe. The 2008 WHO classification of lymphomas: implications for clinical practice and translational research. Hematology 1:523-531 (2009).

Janssen Biotech, Inc. An open label treatment use protocol for ibrutinib in subjects with relapsed or refractory mantel cell lymphoma. In: ClinicalTrials.gov [Internet]. Bethesda (MD): National Library of Medicine (US). Apr. 6, 2013—[cited Nov. 22, 2013]. Available from: http://clinicaltrials.gov/ct2/show/NCT01833039 NLM Identifier: NCT01833039.

Janssen Pharmaceutical K.K. A study to evaluate the Bruton's tyrosine kinase (Btk) inhibitor PCI-32765 in patients with recurrent mature B-cell neoplasms. In: ClinicalTrials.gov [Internet]. Bethesda (MD): National Library of Medicine (US). Oct. 9, 2012—[cited Nov. 22, 2013]. Available from: http://clinicaltrials.gov/ct2/show/NCT01704963 NLM Identifier: NCT01704963.

Janssen Pharmaceutical K.K. Study of the Bruton's Tyrosine Kinase (BTK) Inhibitor Ibrutinib in Participants With Relapsed or Refractory Mantle Cell Lymphoma. In: ClinicalTrials.gov [Internet]. Bethesda (MD): National Library of Medicine (US). Jun. 19, 2014—[cited Feb. 5, 2015] Available from: https://clinicaltrial.gov/ct2/show/NCT02169180?term=NCT02169180 NLM Identifier: NCT02169180.

Janssen Research & Development, LLC. A Study to Evaluate the Effects of Ibrutinib on Cardiac Repolarization in Healthy Participants. In: ClinicalTrials.gov [Internet]. Bethesda (MD): National Library of Medicine (US). Oct. 20, 2014 [cited Feb. 5, 2015] Available from: https://clinicaltrial.gov/ct2/show/NCT02271438?term=NCT02271438 NLM Identifier: NCT02271438.

Janssen Research & Development, LLC. Pharmacokinetic and Pharmacodynamic Study to Evaluate Safety and Efficacy of the Combination of Ibrutinib With Nivolumab in Participants With Hematologic Malignancies. In: ClinicalTrials.gov [Internet]. Bethesda (MD): National Library of Medicine (US). Dec. 30, 2014 [cited Feb. 5, 2015] Available from: https://clinicaltrial.gov/ct2/show/NCT02329847?term=NCT02329847 NLM Identifier: NCT02329847.

Janssen Research and Development, LLC. A long-term extension study of PCI-32765 (Ibrutinib). In: ClinicalTrials.gov [Internet]. Bethesda (MD): National Library of Medicine (US). Mar. 4, 2013—[cited Nov. 22, 2013]. Available from: http://clinicaltrials.gov/ct2/show/NCT01804686 NLM Identifier: NCT01804686.

Janssen Research and Development, LLC. A pharmacokinetic study in healthy participants to assess the pharmacokinetics and safety of a supratherapeutic dose of PCI-32765 (Ibrutinib) capsule and solution formulations administered with food. In: ClinicalTrials.gov [Internet]. Bethesda (MD): National Library of Medicine (US). Aug. 19, 2013—[cited Nov. 22, 2013]. Available from: http://clinicaltrials.gov/ct2/show/NCT01969266 NLM Identifier: NCT01969266.

Janssen Research and Development, LLC. A study combining Ibrutinib with rituximab, cyclophosphamide, doxorubicin, vincristine, and prednisone in patients with CD20-positive B-cell non Hodgkin lymphoma. In: ClinicalTrials.gov [Internet]. Bethesda (MD): National Library of Medicine (US). Mar. 30, 2012—[cited Nov. 22, 2013]. Available from: http://clinicaltrials.gov/ct2/show/NCT01569750 NLM Identifier: NCT01569750.

Janssen Research and Development, LLC. A study of ibrutinib in combination with bendamustine and rituximab in patients with relapsed or refractory chronic lymphocytic leukemia or small lymphocytic lymphoma. In: ClinicalTrials.gov [Internet]. Bethesda (MD): National Library of Medicine (US). May 15, 2012—[cited Nov. 22, 2013]. Available from: http://clinicaltrials.gov/ct2/show/NCT01611090 NLM Identifier: NCT01611090.

Janssen Research and Development, LLC. A study of PCI-32765 (Ibrutinib) in combination with either bendamustine and rituximab or rituximab, cyclophosphamide, doxorubicin, vincristine, and prednisone in patients with previously treated indolent non-Hodgkin lymphoma. In: ClinicalTrials.gov [Internet]. Bethesda (MD): National Library of Medicine (US). Oct. 28, 2013—[cited Nov. 22, 2013]. Available from: http://clinicaltrials.gov/ct2/show/NCT01974440 NLM Identifier: NCT01974440.

Janssen Research and Development, LLC. A study of PCI-32765 (Ibrutinib) in patients with refractory follicular lymphoma. In: ClinicalTrials.gov [Internet]. Bethesda (MD): National Library of Medicine (US). Jan. 25, 2013—[cited Nov. 22, 2013]. Available from: http://clinicaltrials.gov/ct2/show/NCT01779791 NLM Identifier: NCT01779791.

Janssen Research and Development, LLC. A study of the Bruton's tyrosine kinase inhibitor ibrutinib given in combination with bendamustine and rituximab in patients with newly diagnosed mantel cell lymphoma. In: ClinicalTrials.gov [Internet]. Bethesda (MD): National Library of Medicine (US). Jan. 24, 2013—[cited Nov. 22, 2013]. Available from: http://clinicaltrials.gov/ct2/show/NCT01776840 NLM Identifier: NCT01776840.

Janssen Research and Development, LLC. A study of the Bruton's tyrosine kinase inhibitor PCI-32765 (Ibrutinib) versus rituximab in patients with relapsed or refractory chronic lymphocytic leukemia/small lymphocytic lymphoma. In: ClinicalTrials.gov [Internet]. Bethesda (MD): National Library of Medicine (US). Oct. 25, 2013—[cited Nov. 22, 2013]. Available from: http://clinicaltrials.gov/ct2/show/NCT01973387 NLM Identifier: NCT01973387.

Janssen Research and Development, LLC. A study on the Bruton's tyrosine kinase inhibitor, PCI-32765 (Ibrutinib), in combination with rituximab, cyclophosphamide, doxorubicin, vincristine, and prednisone in patients with newly diagnosed non-germinal center B-cell subtype of diffuse large B-cell lymphoma. In: ClinicalTrials.gov [Internet]. Bethesda (MD): National Library of Medicine (US). May 14, 2013—[cited Nov. 22, 2013]. Available from: http://clinicaltrials.gov/ct2/show/NCT01855750 NLM Identifier: NCT01855750.

Janssen Research and Development, LLC. A study to assess the absolute bioavailability of Oral PCI-32765 and the effect of grapefruit juice on the bioavailability of PCI-32765 in healthy participants. In: ClinicalTrials.gov [Internet]. Bethesda (MD): National

(56) References Cited

OTHER PUBLICATIONS

Library of Medicine (US). May 28, 2013—[cited Nov. 22, 2013]. Available from: http://clinicaltrials.gov/ct2/show/study/NCT01866033 NLM Identifier: NCT01866033.

Janssen Research and Development, LLC. A study to assess the effect of ketoconazole on the pharmacokinetics of ibrutinib in healthy participants. In: ClinicalTrials.gov [Internet]. Bethesda (MD): National Library of Medicine (US). Jun. 18, 2012—[cited Nov. 22, 2013]. Available from: http://clinicaltrials.gov/ct2/show/NCT01626651 NLM Identifier: NCT01626651.

Janssen Research and Development, LLC. A study to assess the effect of rifampin on the pharmacokinetics of PCI-32765 in healthy participants. In: ClinicalTrials.gov [Internet]. Bethesda (MD): National Library of Medicine (US). Jan. 4, 2013—[cited Nov. 22, 2013]. Available from: http://clinicaltrials.gov/ct2/show/NCT01763021 NLM Identifier: NCT01763021.

Janssen Research and Development, LLC. A study to determine the absorption, metabolism, and routes of excretion of (14C) radiolabeled ibrutinib in healthy male participants. In: ClinicalTrials.gov [Internet]. Bethesda (MD): National Library of Medicine (US). Aug. 9, 2012—[cited Nov. 22, 2013]. Available from: http://clinicaltrials.gov/ct2/show/NCT01674322 NLM Identifier: NCT01674322.

Janssen Research and Development, LLC. A study to determine the effect of food on the pharmacokinetics of PCI-32765. In: ClinicalTrials.gov [Internet]. Bethesda (MD): National Library of Medicine (US). Mar. 4, 2013—[cited Nov. 22, 2013]. Available from: http://clinicaltrials.gov/ct2/show/NCT01820936 NLM Identifier: NCT01820936.

Janssen Research and Development, LLC. A study to evaluate the efficacy and safety of ibrutinib, in patients with mantel cell lymphoma who progress after bortezomib therapy. In: ClinicalTrials.gov [Internet]. Bethesda (MD): National Library of Medicine (US). May 14, 2012—[cited Nov. 22, 2013]. Available from: http://clinicaltrials.gov/ct2/show/NCT01599949 NLM Identifier: NCT01599949.

Janssen Research and Development, LLC. A study to evaluate the pharmacokinetics of PCI-32765 in participants with varying degrees of hepatic impairment. In: ClinicalTrials.gov [Internet]. Bethesda (MD): National Library of Medicine (US). Jan. 9, 2013—[cited Nov. 22, 2013]. Available from: http://clinicaltrials.gov/ct2/show/NCT01767948 NLM Identifier: NCT01767948.

Janssen Research and Development, LLC. Study of ibrutinib (a Bruton's tyrosine kinase inhibitor), versus temsirolimus in patients with relapsed or refractory mantel cell lymphoma who have received at least one prior therapy. In: ClinicalTrials.gov [Internet]. Bethesda (MD): National Library of Medicine (US). Jul. 18, 2012—[cited Nov. 22, 2013]. Available from: http://clinicaltrials.gov/ct2/show/NCT01646021 NLM Identifier: NCT01646021.

Jefferies et al., "Bruton's tyrosine kinase is a toll/interleukin-1 receptor domain-binding protein that participates in nuclear factor kB activation by toll-like receptor 4," J Biol Chem, 278:26258-64 (2003).

Kamb. What's wrong with our cancer models? Nature Reviews Drug Discovery 4:161-165 (2005).

Kawakami et al. Terreic acid, a quinone epoxide inhibitor of Bruton's tyrosine kinase. PNAS USA 96:2227-2232 (1999).

Korade-Mirnics et al. Src kinase-mediated signaling in leukocytes. J. Leukoc. Bio., 68(5):603-613 (Nov. 2000).

Kozaki et al. Development of a Bruton's tyrosine kinase (Btk) inhibitor-ONO-WG-307, a potential treatment for B-cell malignancies. 53rd American Society of Hematology Annual Meeting and Exposition, San Diego, CA, Poster #857 (Dec. 10-13, 2011).

Kuglstatter et al. Insights into the conformational flexibility of Bruton's tyrosine kinase from multiple ligand complex structures. Protein Science 20(2):428-436 (2011) [E-pub Dec. 17, 2010].

Kuppers. Mechanisms of B-cell lymphoma pathogenesis. Nature Reviews/Cancer 5:251-262 (2005).

Kurosaki. Functional dissection of BCR signaling pathways. Curr. Op. Imm. 12:276-281 (2000).

Kushner et al. Pharmacological uses and perspective of heavy water and deuterated compounds. Canadian Journal of Physiology and Pharmacology 77(2):79-88 (1999).

Label for IMBRUVICA® (ibrutinib), revised Feb. 2018.

Label for TASIGNA® (nilotinib), revised Aug. 2009.

Larsen et al., "Prodrug Forms for the Sulfonamide Group. II. Water-soluble Amino Acid Derivatives of N-methylsulfonamides as Possible Prodrugs," Int J Pharmaceutics, 47: 103-110 (1988).

Larsen et al. Prodrug forms for the sulfonamide group. I. Evaluation of N-acyl derivatives, N-sulfonylaminedes, N-sulfonylsulfilimines and sulfonylureas as possible prodrug derivatives. Int. J. Pharmaceutics 37:87-95 (1987).

Le Tourneau et al. Dose Escalation Methods in Phase I Cancer Clinical Trials. J. Natl Cancer 101:708-720 (2009).

Li et al. Activation of Bruton's Tyrosine Kinase (BTK) by a Point Mutation in its Pleckstrin Homology (PH) domain. Immunity 2:451-460 (1995).

Lim et al. Asymmetric syntheses of fused bicyclic lactams. Journal of Organic chemistry 66(26):9056-9062 (2001).

Lin et al. Selective Itk inhibitors block T-cell activation and murine lung inflammation, Biochemistry 43:11056-11062 (2004).

Liu et al. Structural Basis for selective inhibition of Src family kinases by PPI. Chemistry and Biology 6:671-678, in particular table 1, p. 671 (1999).

Lossos. Molecular Pathogenesis of Diffuse Large B-Cell Lymphoma. J. Clin. Oncol. 23(26):6351-6357 (Sep. 10, 2005).

Lou et al. Bruton's tyrosine kinase inhibitors: approaches to potent and selective inhibition, preclinical and clinical evaluation for inflammatory diseases and B cell malignancies. J Med Chem. May 24, 2012;55(10):4539-50 Publication Date (Web): Mar. 6, 2012.

Luskova et al. Modulation of the Fce Receptor I Signaling by Tyrosine Kinase Inhibitors: Search for Therapeutic Targets of Inflammatory and Allergy Diseases. Curr. Pharmaceutical Design 10:1727-1737 (2004).

M.D. Anderson Cancer Center. A Phase I/II Study of Ibrutinib in Previously Treated Epidermal Growth Factor Receptor (EGFR) Mutant Non-Small Cell Lung Cancer. In: ClinicalTrials.gov [Internet]. Bethesda (MD): National Library of Medicine (US). 2014 Dec. 17, 2014[cited Feb. 5, 2015] Available from: https://clinicaltrial.gov/ct2/show/NCT02321540?term=NCT02321540 NLM Identifier: NCT02321540.

M.D. Anderson Cancer Center. A Phase I/II Trial of PCI-32765 (BTK Inhibitor) in Combination With Carfilzomib in Relapse/Refractory Mantle Cell Lymphoma. In: ClinicalTrials.gov [Internet]. Bethesda (MD): National Library of Medicine (US). Oct. 16, 2014 [cited Feb. 5, 2015] Available from: https://clinicaltrial.gov/ct2/show/NCT02269085?term=NCT02269085 NLM Identifier: NCT02269085.

M.D. Anderson Cancer Center. Ibrutinib Post Stem Cell Transplantation (SCT) in Double-Hit B-Cell Lymphoma. In: ClinicalTrials.gov [Internet]. Bethesda (MD): National Library of Medicine (US). Oct. 21, 2014 [cited Feb. 5, 2015] Available from: https://clinicaltrial.gov/ct2/show/NCT02272686?term=NCT02272686 NLM Identifier: NCT02272686.

M.D. Anderson Cancer Center. Ibrutinib versus ibrutinib + rituximab (i vs iR) in patients with relapsed chronic lymphocytic leukemia (CLL). In: ClinicalTrials.gov [Internet]. Bethesda (MD): National Library of Medicine (US). Dec. 5, 2013—[cited Apr. 15, 2014]. Available from: http://clinicaltrials.gov/ct2/show/NCT02007044 NLM Identifier: NCT02007044.

M.D. Anderson Cancer Center. Phase 2 ibrutinib + rituximab in relapsed/refractory mantel cell lymphoma (R/R MCL). In: ClinicalTrials.gov [Internet]. Bethesda (MD): National Library of Medicine (US). Jun. 14, 2013—[cited Nov. 22, 2013]. Available from: http://clinicaltrials.gov/ct2/show/NCT01880567 NLM Identifier: NCT01880567.

M.D. Anderson Cancer Center. Phase 2 study of the combination of Bruton's tyrosine kinase inhibitor PCI-32765 and rituximab in high-risk chronic lymphocytic leukemia and small lymphocytic lymphoma patients. In: ClinicalTrials.gov [Internet]. Bethesda (MD): National Library of Medicine (US). Jan. 25, 2012—[cited Nov. 22, 2013]. Available from: http://clinicaltrials.gov/ct2/show/NCT01520519 NLM Identifier: NCT01520519.

(56) References Cited

OTHER PUBLICATIONS

M.D. Anderson Cancer Center. Pilot study to determine effects of the Btk inhibitor PCI-32765 on leukemia cell kinetics and trafficking, using heavy water labeling in subjects with CLL and SLL. In: ClinicalTrials.gov [Internet]. Bethesda (MD): National Library of Medicine (US). Dec. 13, 2012—[cited Nov. 22, 2013]. Available from: http://clinicaltrials.gov/ct2/show/NCT01752426 NLM Identifier: NCT01752426.
Macpartlin et al. Bruton's tyrosine kinase is not essential for Bcr-Abl-mediated transformation of lymphoid or myeloid cells. Leukemia 22:1354-1360 (2008).
Maddocks et al. Ibrutinib in B-cell lymphomas. Current Treatment Options in Oncology 15:226-237 (2014) (Epub: Feb. 1, 2014).
Mahajan et al. Rational Design and Synthesis of a Novel Antileukemic Agent Targeting Bruton's Tyrosine Kinase (BTK), LFM-A13 [a-Cyano-β-Methyl-N-(2,5-Dibromophenyl)Propenamide]. J. of Biol. Chem. 274(14):9587-9599 (1999).
Mallis et al. Structural characterization of a proline-driven conformational switch within the Itk SH2 domain. Nat. Struct. Biol., 9(12):900-905 (2002).
Mangla et al., "Pleiotropic consequences of Bruton tyrosine kinase deficiency in myeloid lineages lead to poor inflammatory responses," Blood, 104(4):1191-1197 (2004).
Marina et al. Biology and Therapeutic Advances for Pediatric Osteosarcoma. The Oncologist 9:422-441 (2004).
McConathy et al. Stereochemistry in Drug Action. J Clinical Psychiatry. 5:70-73 (2003).
McLeod et al., "A glucocorticoid prodrug facilitates normal mucosal function in rat colitis without adrenal suppression," Gastroenterol, 106:405-413 (1994).
Memorial Sloan-Kettering Cancer Center. Bruton's Tyrosine Kinase (BTK) Inhibitor, Ibrutinib, in Patients With Refractory/Recurrent Primary Central Nervous System Lymphoma (PCNSL) and Refractory/Recurrent Secondary Central Nervous System Lymphoma (SCNSL). In: ClinicalTrials.gov [Internet]. Bethesda (MD): National Library of Medicine (US). Dec. 9, 2014 [cited Feb. 5, 2015] Available from: https://clinicaltrial.gov/ct2/show/NCT02315326?term=NCT02315326 NLM Identifier: NCT02315326.
Mendel et al., "In vivo Antitumor Activity of SU11248, A Novel Tyrosine Kinase Inhibitor Targeting Vascular Endothelial Growth Factor and Platelet-derived Growth Factor Receptors: Determination of a Pharmacokinetic/pharmacodynamic Relationship," Clin Cancer Res, 9(1): 327-337 (2003).
Merged Markush Service Search, Jun. 27, 2005.
Middendorp et al. Function of Bruton's Tyrosine Kinase during B Cell Development is Partially Independent of its Catalytic Activity. J Immunol 171:5988-5996 (2003).
Middendorp et al. Tumor Suppressor Function of Bruton Tyrosine Kinase is Independent of its catalytic activity. Blood 105(1):259-261 (2005).
Morissette et al., "High-throughput Crystallization: Polymorphs, Salts, Co-Crystals and Solvates of Pharmaceutical Solids," Advanced Drug Delivery Review, 56: 275-300 (2004).
Mukoyama et al., "Preparation of imidazol [1,5-a]pyrazine derivatives, pharmaceutical compositions containing them, and their uses for prevention or treatment of protein tyrosine kinase-related diseases," retrieved from STN Database Accession No. 2005:299462 Patent No. JP2005089352, Abstract (2005).
National Cancer Institute (NCI). A multicenter phase 2 study of the Bruton's tyrosine kinase inhibitor PCI-32765 for treatment of relapsed hairy cell leukemia. In: ClinicalTrials.gov [Internet]. Bethesda (MD): National Library of Medicine (US). Nov 2, 2013—[cited Nov. 22, 2013]. Available from: http://clinicaltrials.gov/ct2/show/NCT01981512 NLM Identifier: NCT01981512.
National Cancer Institute (NCI). Ibrutinib and rituximab compared with fludarabine phosphate, cyclophosphamide, and rituximab in treating patients with untreated chronic lymphocytic leukemia or small lymphocytic lymphoma. In: ClinicalTrials.gov [Internet]. Bethesda (MD): National Library of Medicine (US). Jan. 27, 2014—[cited Apr. 15, 2014]. Available from: http://clinicaltrials.gov/ct2/show/NCT02048813 NLM Identifier: NCT02048813.
National Cancer Institute (NCI). Ibrutinib in treating patients with relapsed hairy cell leukemia. In: ClinicalTrials.gov [Internet]. Bethesda (MD): National Library of Medicine (US). Apr. 24,2013—[cited Nov. 22, 2013]. Available from: http://clinicaltrials.gov/ct2/show/NCT01841723 NLM Identifier: NCT01841723.
National Cancer Institute (NCI). Ibrutinib in treating patients with relapsed or refractory follicular lymphoma. In: ClinicalTrials.gov [Internet]. Bethesda (MD): National Library of Medicine (US). May 6, 2013—[cited Nov. 22, 2013]. Available from: http://clinicaltrials.gov/ct2/show/NCT01849263 NLM Identifier: NCT01849263.
National Cancer Institute (NCI). Lenalidomide and ibrutinib in treating patients with relapsed or refractory B-Cell non-Hodgkin lymphoma. In: ClinicalTrials.gov [Internet]. Bethesda (MD): National Library of Medicine (US). Sep. 27, 2013—[cited Nov. 22, 2013]. Available from: http://clinicaltrials.gov/ct2/show/NCT01955499 NLM Identifier: NCT01955499.
National Cancer Institute (NCI). Rituximab and bendamustine hydrochloride, rituximab and ibrutinib, or ibrutinib alone in treating older patients with previously untreated chronic lymphocytic leukemia. In: ClinicalTrials.gov [Internet]. Bethesda (MD): National Library of Medicine (US). Jun. 24, 2013—[cited Nov. 22, 2013]. Available from: http://clinicaltrials.gov/ct2/show/NCT01886872 NLM Identifier: NCT01886872.
National Cancer Institute (NCI). Rituximab, lenalidomide, and ibrutinib in treating patients with previously untreated stage II-IV follicular lymphoma. In: ClinicalTrials.gov [Internet]. Bethesda (MD): National Library of Medicine (US). Apr. 9, 2013—[cited Nov. 22, 2013]. Available from: http://clinicaltrials.gov/ct2/show/NCT01829568 NLM Identifier: NCT01829568.
National Cancer Institute. Ibrutinib and Combination Chemotherapy in Treating Patients With Relapsed or Refractory Diffuse Large B-Cell Lymphoma. In: ClinicalTrials.gov [Internet]. Bethesda (MD): National Library of Medicine (US). Jul. 16, 2014 [cited Feb. 5, 2015] Available from: https://clinicaltrial.gov/ct2/show/NCT02219737?term=NCT02219737 NLM Identifier: NCT02219737.
National Cancer Institute. Ibrutinib and Palbociclib Isethionate in Treating Patients With Previously Treated Mantle Cell Lymphoma. In: ClinicalTrials.gov [Internet]. Bethesda (MD): National Library of Medicine (US). Jun. 9, 2014—[cited Feb. 5, 2015] Available from: https://clinicaltrial.gov/ct2/show/NCT02159755?term=NCT02159755 NLM Identifier: NCT02159755.
National Cancer Institute. Ibrutinib in Treating Patients With Relapsed or Refractory B-cell Acute Lymphoblastic Leukemia. In: ClinicalTrials.gov [Internet]. Bethesda (MD): National Library of Medicine (US). Apr. 30, 2014 [cited Feb. 5, 2015] Available from: https://clinicaltrial.gov/ct2/show/NCT02129062?term=NCT02129062 NLM Identifier: NCT02129062.
National Cancer Institute. Ibrutinib in Treating Relapsed or Refractory B-cell Non-Hodgkin Lymphoma in Patients With HIV infection. In: ClinicalTrials.gov [Internet]. Bethesda (MD): National Library of Medicine (US). Apr. 7, 2014 [ cited Feb. 5, 2015]. Available from: https://clinicaltrial.gov/ct2/show/NCT02109224?term=NCT02109224. NLM Identifier: NCT02109224.
National Cancer Institute. Lenalidomide, Ibrutinib, and Rituximab in Treating Patients With Relapsed or Refractory Chronic Lymphocytic Leukemia or Small Lymphocytic Lymphoma. In: ClinicalTrials.gov [Internet]. Bethesda (MD): National Library of Medicine (US). May 30, 2014 [cited Feb. 15, 2015] Available from: https://clinicaltrial.gov/ct2/show/NCT02160015?term=NCT02160015 NLM Identifier: NCT02160015.
National Cancer Institute. Phase 1 Study of Ibrutinib and Immuno-Chemotherapy Using Dose-Adjusted-Temozolomide, Etoposide, Doxil, Dexamethasone, Ibrutinib,Rituximab (DA-TEDDI-R) in Primary CNS Lymphoma. In: ClinicalTrials.gov [Internet]. Bethesda (MD): National Library of Medicine (US). Jul. 29, 2014 [cited Feb. 5, 2015] Available from: https://clinicaltrial.gov/ct2/show/NCT02203526?term=NCT02203526 NLM Identifier: NCT02203526.
National Center Institute (NCI). Lenalidomide and Ibrutinib in treating patients with relapsed or refractory chronic lymphocytic leukemia or small lymphocytic lymphoma. In: ClinicalTrials.gov [Internet]. Bethesda (MD): National Library of Medicine (US). Jun.

(56) References Cited

OTHER PUBLICATIONS 24, 2013—[cited Nov. 22, 2013]. Available from: http://clinicaltrials.gov/ct2/show/NCT01886859 NLM Identifier: NCT01886859.
National Heart, Lung, and Blood Institute (NHLBI). PCI-32765 for special cases of chronic lymphocytic leukemia or small lymphocytic lymphoma. In: ClinicalTrials.gov [Internet]. Bethesda (MD): National Library of Medicine (US). Dec. 22, 2011—[cited Nov. 22, 2013]. Available from: http://clinicaltrials.gov/ct2/show/NCT01500733 NLM Identifier: NCT01500733.
Niiro et al. Regulation of B-Cell Fate by Antigen-Receptor Signals. Nature Reviews 2:945-956 (2002).
Nisitani et al. In situ detection of activated Bruton's tyrosine kinase in the Ig signaling complex by phosphopeptide-specific monoclonal antibodies. PNAS USA 96:2221-2226 (1999).
Nogrady (1985) Medicinal Chemistry A Biochemical Approach, Oxford University Press, New York, pp. 388-394.
Northwestern University. Ibrutinib After Intensive Induction in Treating Patients With Previously Untreated Mantle Cell Lymphoma. In: ClinicalTrials.gov [Internet]. Bethesda (MD): National Library of Medicine (US). Sep. 12, 2014 [cited 2-15 Feb. 5] Available from: https://clinicaltrial.gov/ct2/show/NCT02242097?term=NCT02242097 NLM Identifier: NCT02242097.
Ohio State University Comprehensive Cancer Center. PCI-32765 (Ibrutinib) in treating patients with relapsed or refractory chronic lymphocytic leukemia, small lymphocytic lymphoma, or B-cell prolymphocytic leukemia. In: ClinicalTrials.gov [Internet]. Bethesda (MD): National Library of Medicine (US). Apr. 23, 2012—[cited Nov. 22, 2013]. Available from: http://clinicaltrials.gov/ct2/show/NCT01589302 NLM Identifier: NCT01589302.
Ohio State University Comprehensive Cancer Center. Rituxan/Bendamustine/PCI-32765 in relapsed DLBCL, MCL, or indolent non-Hodgkin's lymphoma. In: ClinicalTrials.gov [Internet]. Bethesda (MD): National Library of Medicine (US). Nov. 1, 2011—[cited Feb. 6, 2014]. Available from: http://clinicaltrials.gov/ct2/show/NCT01479842 NLM Identifier: NCT01479842.
Oligino et al. Targeting B cells for the treatment of rheumatoid arthritis. Arthritis Res. Ther., 5(Suppl.4):S7-S11 (2002).
Pagel et al., "Induction of apoptosis using inhibitors of lysophosphatidic acid acyltransferase-beta and anti-CD20 monoclonal antibodies for treatment of human non-Hodgkin's lymphomas," Clin Cancer Res, 11(13):4857-4866 (2005).
Pan et al., "Discovery of selective irreversible inhibitors for Bruton's tyrosine kinase," ChemMedChem, 2:58-61 (2007).
PCT/US06/49626 Search Report dated Apr. 9, 2008.
PCT/US08/058528 Search Report and Written Opinion dated Sep. 30, 2008.
PCT/US09/50897 Iper and Written Opinion dated Jan. 27, 2011.
PCT/US09/50897 Search Report dated Mar. 15, 2010.
PCT/US10/52377 Search Report and Written Opinion dated Jun. 29, 2011.
PCT/US2006/49626 International Preliminary Report on Patentability Search Report dated Mar. 24, 2009.
PCT/US2008/058528 International Preliminary Report on Patentability Search Report dated Sep. 29, 2009.
PCT/US2008/058528 International Search Report and Written Opinion dated Sep. 30, 2008.
PCT/US2009/50897 International Preliminary Examination Report and Written Opinion dated Jan. 18, 2011.
PCT/US2010/52377 International Search Report and Written Opinion dated Jun. 29, 2011.
PCT/US2013/043888 International Preliminary Report on Patentability dated Dec. 9, 2014.
PCT/US2013/043888 International Search Report and Written Opinion dated Sep. 23, 2013.
PCT/US2015/044258 International Search Report and Written Opinion dated Nov. 6, 2015.
PCT/US2015/16895 International Search Report and Written Opinion dated May 22, 2015.
PCT/US2015/21871 International Search Report and Written Opinion dated Jul. 8, 2015.
Peterson et al. Prolonged single-agent versus combination chemotherapy in indolent follicular lymphomas: a study of the cancer and leukemia group. Br. J. Clin. Oncol., 21(1):5-15 (Jan. 1, 2003).
Pharmacyclics, Inc. A Multi-Center Study of Ibrutinib in Combination With Obinutuzumab Versus Chlorambucil in Combination With Obinutuzumab in Patients With Treatment naïve CLL or SLL. In: ClinicalTrials.gov [Internet]. Bethesda (MD): National Library of Medicine (US). Oct. 1, 2014 [cited Feb. 5, 2015] Available from: https://clinicaltrial.gov/ct2/show/NCT02264574?term=NCT02264574 NLM Identifier: NCT02264574.
Pharmacyclics, Inc. A multicenter phase 2 study of PCI-32765 (Ibrutinib) in patients with relapsed or refractory chronic lymphocytic leukemia (CLL) or small lymphocytic lymphoma (SLL) with 17p deletion. In: ClinicalTrials.gov [Internet]. Bethesda (MD): National Library of Medicine (US). Dec. 3, 2012—[cited Nov. 22, 2013]. Available from: http://clinicaltrials.gov/ct2/show/NCT01744691 NLM Identifier: NCT01744691.
Pharmacyclics, Inc. A multicenter, open-label, phase 3 study of the Bruton's tyrosine kinase inhibitor PCI-32765 versus chlorambucil in patients 65 years or older with treatment-naive chronic lymphocytic leukemia or small lymphocytic lymphoma (Resonate-2). In: ClinicalTrials.gov [Internet]. Bethesda (MD): National Library of Medicine (US). Oct. 29, 2012—[cited Nov. 22, 2013]. Available from: http://clinicaltrials.gov/ct2/show/NCT01722487 NLM Identifier: NCT01722487.
Pharmacyclics, Inc. A phase 3 study of ibrutinib (PCI-32765) versus ofatumumab in patients with relapsed or refractory chronic lymphocytic leukemia (Resonate). In: ClinicalTrials.gov [Internet]. Bethesda (MD): National Library of Medicine (US). Apr. 11, 2012—[cited Nov. 22, 2013]. Available from: http://clinicaltrials.gov/ct2/show/NCT01578707 NLM Identifier: NCT01578707.
Pharmacyclics, Inc. An open-label extension study in patients 65 years or older with chronic lymphocytic leukemia (CLL) or small lymphocytic lymphoma (SLL) who participated in study PCYC-115-CA (PCI-32765 versus chlorambucil). In: ClinicalTrials.gov [Internet]. Bethesda (MD): National Library of Medicine (US). Nov. 2, 2012—[cited Nov. 22, 2013]. Available from: http://clinicaltrials.gov/ct2/show/NCT01724346 NLM Identifier: NCT01724346.
Pharmacyclics, Inc. Efficacy and safety study of PCI-32765 combined with ofatumumab in CLL (PCYC-1109-CA). In: ClinicalTrials.gov [Internet]. Bethesda (MD): National Library of Medicine (US). Oct. 7, 2010—[cited Nov. 22, 2013]. Available from: http://clinicaltrials.gov/ct2/show/NCT01217749 NLM Identifier: NCT01217749.
Pharmacyclics, Inc. Ibrutinib and Lenalidomide With Dose Adjusted EPOCH-R in Subjects With Relapsed/Refractory Diffuse Large B-cell Lymphoma. In: ClinicalTrials.gov [Internet]. Bethesda (MD): National Library of Medicine (US). May 12, 2014 [cited Feb. 5, 2015] Available from: https://clinicaltrial.gov/ct2/show/NCT02142049?term=NCT02142049 NLM Identifier: NCT02142049.
Pharmacyclics, Inc. Ibrutinib in combination with lenalidomide, with and without rituximab in participants with relapsed or refractory diffuse large B-cell lymphoma. In: ClinicalTrials.gov [Internet]. Bethesda (MD): National Library of Medicine (US). Feb. 10, 2014—[cited Apr. 15, 2014]. Available from: http://clinicaltrials.gov/ct2/show/NCT02077166 NLM Identifier: NCT02077166.
Pharmacyclics, Inc. Ibrutinib With Rituximab in Previously Treated Adults With Waldenstrom's Macroglobulinemia. In: ClinicalTrials.gov [Internet]. Bethesda (MD): National Library of Medicine (US). Jun. 9, 2014 [cited Feb. 5, 2015] Available from: https://clinicaltrial.gov/ct2/show/NCT02165397?term=NCT02165397 NLM Identifier: NCT02165397.
Pharmacyclics, Inc. Safety and efficacy of PCI-32765 in subjects with relapsed/refractory mantel cell lymphoma (MCL). In: ClinicalTrials.gov [Internet]. Bethesda (MD): National Library of Medicine (US). Oct. 18, 2010—[cited Nov. 22, 2013]. Available from: http://clinicaltrials.gov/ct2/show/NCT01236391 NLM Identifier: NCT01236391.
Pharmacyclics, Inc. Safety and efficacy study of Bruton's tyrosine kinase inhibitor in subjects with relapsed or refractory diffuse large B-cell lymphoma. In: ClinicalTrials.gov [Internet]. Bethesda (MD): National Library of Medicine (US). Feb. 2, 2011—[cited Nov. 22,

(56) References Cited

OTHER PUBLICATIONS

2013]. Available from: http://clinicaltrials.gov/ct2/show/NCT01325701 NLM Identifier: NCT01325701.
Pharmacyclics, Inc. Safety and tolerability study of PCI-32765 combined with fludarabine/cyclophosphamide/rituximab (FCR) and bendamustine/rituximab (BR) in chronic lymphocytic leukemia (CLL). In: ClinicalTrials.gov [Internet]. Bethesda (MD): National Library of Medicine (US). Feb. 2, 2011—[cited Nov. 22, 2013]. Available from: http://clinicaltrials.gov/ct2/show/NCT01292135 NLM Identifier: NCT01292135.
Pharmacyclics, Inc. Safety and tolerability study of PCI-32765 in B Cell lymphoma and chronic lymphocytic leukemia. In: ClinicalTrials.gov [Internet]. Bethesda (MD): National Library of Medicine (US). Apr. 19, 2010—[cited Nov. 25, 2013]. Available from: http://clinicaltrials.gov/ct2/show/NCT01109069 NLM Identifier: NCT01109069.
Pharmacyclics, Inc. Safety of PCI-32765 in chronic lymphocytic leukemia. In: ClinicalTrials.gov [Internet]. Bethesda (MD): National Library of Medicine (US). Apr. 13, 2010—[cited Nov. 22, 2013]. Available from: http://clinicaltrials.gov/ct2/show/NCT01105247 NLM Identifier: NCT01105247.
Pharmacyclics, Inc. Study of the Bruton's tyrosine kinase inhibitor in combination with carfilzomib (Kyprolis), in subjects with relapsed or relapsed and refractory multiple myeloma. In: ClinicalTrials.gov [Internet]. Bethesda (MD): National Library of Medicine (US). Sep. 27, 2013—[cited Nov. 22, 2013]. Available from: http://clinicaltrials.gov/ct2/show/NCT01962792 NLM Identifier: NCT01962792.
Pharmacyclics, Inc. Study of the Bruton's tyrosine kinase inhibitor in combination with rituximab in previously untreated subjects with follicular lymphoma. In: ClinicalTrials.gov [Internet]. Bethesda (MD): National Library of Medicine (US). Oct. 24, 2013—[cited Nov. 22, 2013]. Available from: http://clinicaltrials.gov/ct2/show/NCT01980654 NLM Identifier: NCT01980654.
Pharmacyclics, Inc. Study of the Bruton's Tyrosine Kinase Inhibitor in Subjects With Chronic Graft Versus Host Disease. In: ClinicalTrials.gov [Internet]. Bethesda (MD): National Library of Medicine (US). Jul. 11, 2014 [cited Feb. 5, 2015] Available from: https://clinicaltrial.gov/ct2/show/NCT02195869?term=NCT02195869 NLM Identifier: NCT02195869.
Pharmacyclics, Inc. Study of the Bruton's tyrosine kinase inhibitor in subjects with relapsed or relapsed and refractory multiple myeloma. In: ClinicalTrials.gov [Internet]. Bethesda (MD): National Library of Medicine (US). Nov. 18, 2011—[cited Nov. 22, 2013]. Available from: http://clinicaltrials.gov/ct2/show/NCT01478581 NLM Identifier: NCT01478581.
Pharmacyclics, Inc. Study of the Bruton's tyrosine kinase inhibitor in subjects with relapsed/refractory marginal zone lymphoma. In: ClinicalTrials.gov [Internet]. Bethesda (MD): National Library of Medicine (US). Oct. 29, 2013—[cited Nov. 22, 2013]. Available from: http://clinicaltrials.gov/ct2/show/NCT01980628 NLM Identifier: NCT01980628.
Pharmacyclics, Inc. Study of the safety and tolerability of PCI-32765 in patients with recurrent B cell lymphoma (PCYC-04753). In: ClinicalTrials.gov [Internet]. Bethesda (MD): National Library of Medicine (US). Feb. 20, 2009—[cited Nov. 22, 2013]. Available from: http://clinicaltrials.gov/ct2/show/NCT00849654 NLM Identifier: NCT00849654.
Pharmacyclics: Pharmacyclics initiates phase 1 clinical trial of novel oral Btk inhibitor for refractory B-cell non-Hodgkin's lymphoma. The American Association of Cancer Research (AACR) 100th Annual Meeting in Denver, CO (Apr. 13, 2009).
Pharmacyclics: Study of the Bruton's Tyrosine Kinase Inhibitor in Subjects With Chronic Graft Versus Host Disease. ClinicalTrials.gov [Internet]. Bethesda (MD): National Library of Medicine (US). Jul. 11, 2014. Available from: http://clinicaltrials.gov/show/NCT02195869.
Picci, P. et al., "Osteosarcoma (osteogenic sarcoma)," Orphanet J Rare Dis, 2(6):1-4 (2007).
Pilchik, "Pharmaceutical Blister Packaging, Part 1: Rationale and Materials," Pharmaceutical Technology, 68-77 (Nov. 2000).
Pileri et al. Mantle Cell Lymphoma. Haematologica 94(11):1488-1492 (2009).
Pollyea et al., "A phase I dose escalation study of the Btk inhibitor PCI-32765 in relapsed and refractory B cell non-Hodgkin lymphoma and use of a novel fluorescent probe pharmacodynamic assay," 51st ASH Annual Meeting and Exposition, Poster Abstract #3713 (2009).
Pollyea et al., "A Phase I Dose Escalation Study of the Btk Inhibitor PCI-32765 in Relapsed and Refractory B Cell Non-Hodgkin Lymphoma and Use of a Novel Fluorescent Probe Pharmacodynamics Assay," Blood, 114(22): Abstract No. 3713 (Nov. 20, 2009).
Ponader et al. The Bruton tyrosine kinase inhibitor PCI-32765 thwarts chronic lymphocytic leukemia cell survival and tissue homing in vitro and in vivo. Blood (Epub Dec. 16, 2011), 119(5):1182-1189 (Feb. 2012).
Powers et al. Irreversible Inhibitors of Serine, Cysteine, and Threonine Proteases. Chem. Rev., 102(12):4639-4750 (2002).
Prakash et al. Chicken sarcoma to human cancers: a lesson in molecular therapeutics. The Ochsner Journal, 7(2):61-64 (Jan. 1, 2007).
Prenata et al., "Separation on the basis of size: Gel permeation chromatography," Protein Purification Methods: A Practical Approach, (Harris & Angal Eds.) IRL Press 1989 293-306.
PRNewsire "U.S. FDA grants regular (full) approval for IMBRUVICA for two indications," Jul. 28, 2014.
PRNewswire, "Pharmacyclics, Inc. announces presentation of interim results from phase I trial of its first-in-human Btk inhibitor PCI-32765," Dec. 7, 2009.
PRNewswire, "Update on preclinical finding and development timeline for PCI-45292," Mar. 2, 2011.
Quek et al. A role for Bruton's tyrosine kinase (Btk) in platelet activation by collagen. Curr. Biol. 8(20):1137-1140 (1998).
Rabin et al. Absolute Lymphocyte Counts Refine MRD-Based Risk Stratification in Pediatric All. Blood (Ash Annual Meeting Abstracts) 114:Abstract 1593 (2009).
Rao et al., "Inhibition of Invasion, Angiogenesis, Tumor Growth, and Metastasis by Adenovirus-mediated Transfer of Antisense uPAR and MMP-9 in Non-small Cell Lung Cancer Cells," Mol Cancer Ther, 4(9): 1399-1408 (2005).
Rastetter et al. Rituximab: expanding role in therapy for lymphomas and autoimmune diseases. Ann. Rev. Med 55:477-503 (2004).
Raw et al., "Regulatory Considerations of Pharmaceutical Solid Polymorphism in Abbreviated New Drug Applications (ANDAS)," Adv Drug Deliv Rev, 56: 397-414 (2004).
Remington's Pharmaceutical Sciences, 1995, Mark Printing Co., 17th ed., p. 185.
Ritter et al. Osteosarcoma. Ann. Oncol. 21(Supplement 7):320-325 (2010).
Robak et al. A Targeted Therapy for Protein and Lipid Kinases in Chronic Lymphocytic Leukemia. Curr. Med. Chem. (Epub Jul. 24, 2012), 19(31):5294-5318 (2012).
Robak et al. Tyrosine kinase inhibitors as potential drugs for B-cell lymphoid malignancies and autoimmune disorders. Expert Opin. Investig. Drugs (Epub May 22, 2012), 21(7):921-947 (Jul. 2012).
Rushworth et al. BTK inhibitor ibrutinib is cytotoxic to myeloma and potently enhances bortezomib and lenalidomide activities through NF-κb. Cell Signal (Epub Sep. 11, 2012), 25(1):106-112 (Jan. 2013).
Sada et al. Protein-Tyrosine Kinases and Adaptor Proteins in FceRI-Mediated Signaling in Mast Cells. Curr. Mol. Med. 3(1):85-94 (2003).
Saulnier et al., "An efficient method for the synthesis of guanidine prodrugs," Bioorganic and Medicinal Chemistry Letters, vol. 4, p. 1985-90 (1994).
Schaeffer et al. Tec family kinases in lymphocyte signaling and function. Curr. Op. Imm. 12:282-288 (2000).
Schnute et al., "Bruton's tyrosine kinase (Btk)," Anti-Inflammatory Drug Discovery, Ed. J.I. Levin and S. Laufer, (2012), pp. 297-326.
Schwamb et al. B-cell receptor triggers drug sensitivity of primary CLL cells by controlling glucosylation of ceramides. Blood (Epub Aug. 27, 2012), 120(19):3978-3985 (Nov. 2012).

(56) References Cited

OTHER PUBLICATIONS

Science Daily Counting tumor cells in blood predicts treatment benefit in prostate cancer. (Jul. 7, 2008), http://www.sciencedaily.com/releases/2008/07/080706083142.htm, last accessed Jul. 23, 2013.
Science Daily, "Drug shows surprising efficacy as treatment for chronic leukemia, mantle cell lymphoma," (Jun. 19, 2013), http://www.sciencedaily.com/releases/2013/06/130619195217.htm, last accessed Jan. 15, 2016.
Science IP CAS Search, Mar. 16, 2006.
Science IP CAS Search, Sep. 5, 2006.
Shaffer et al. Lymphoid malignancies: the dark side of B-cell differentiation. Nature Reviews/Immunology 2:920-932 (2002).
Shah et al. Ibrutinib for the treatment of mantle cell lymphoma. Expert Rev. Hematol. 7(5):521-531 (2014) (Epub Aug. 27, 2014).
Silverman. The Organic Chemistry of Drug Design and Drug Action, Academic Press, Inc., San Diego, pp. 352-401 (1992).
Sinkula et al. Rationale for design of biologically reversible drug derivatives: prodrugs. J. Pharm. Sci., 64:181-210 (1975).
Sivina et al. CCL3 (MIP-1a) Plasma Levels and the Risk for Disease Progression in Chronic Lymphocytic Leukemia. Blood 117(5):1662-1669 (2010).
Smaill et al., "Irreversible Inhibitors of the Epidermal Growth Factor Receptor: 4-(Phenylamino)quinazoline- and 4-(Phenylamino)pyrido[3,2-d]pyrimidine-6-acrylamides Bearing Additional Solubilizing Functions," J Med Chem, 43: 1380-1397 (2000).
Smaill et al., "Tyrosine kinase inhibitors. 15. 4-(phenylamino)quinazoline and 4-(phenylamino)pyrido[d]pyrimidine acrylamides as irreversible inhibitors of the ATP binding site of the epidermal growth factor receptor," J Med Chem, 42(10):1803-15 (1999).
Smith et al., "The Tec family of cytoplasmic tyrosine kinases: mammalian Btk, Bmx, Itk, Tec, Txk and homologs in other species," BioEssays, 23:436-46 (2001).
Smolen et al. Therapeutic Strategies for Rheumatoid Arthritis. Nature Reviews 2:473-488 (2003).
Stead et al. Concise synthesis of (+/−)-Cytisine via lithiation of N-Boc-bispidine. Organic Letters 7(20):4459-4462 (2005).
STN Registry No. 936563-96-1. Ibrutinib. Retrieved from STN Registry Jul. 27, 2015. 1 pg.
Strimbu et al. What are biomarkers? Curr Opin HIV AIDS 5(6):463-466 (2010.
Supplementary European Search Report EP13799982.7 dated Dec. 14, 2015.
Supplementary European Search Report for EP 15829513.9, dated Mar. 7, 2018.
Supplementary European Search Report for EP13854424 dated Mar. 14, 2016.
Taiwan Search Report for Application No. 102119583, dated Oct. 24, 2016.
Takahashi et at. Serum CCL3 and CCL4 Levels Function as Novel Prognostic Markers in Diffuse Large B Cell Lymphoma [online]. 54th ASH Annual Meeting and Exposition. [retrieved on Apr. 21, 2015], Abstract 2709. Retrieved from the Internet. URL: https://ash.confex.com/ash/2012/webprogram/Paper53900.html< url:></url:>.
Teja et al., "Drug-excipient behavior in polymeric amorphous solid dispersions," Journal of Excipients and Food Chemicals, 4(3):70-94 (2013).
TG Therapeutics, Inc. Ublituximab + ibrutinib in select B-cell malignancies. In: ClinicalTrials.gov [Internet]. Bethesda (MD): National Library of Medicine (US). Dec. 11, 2013—[cited Apr. 15, 2014]. Available from: http://clinicaltrials.gov/ct2/show/NCT02013128 NLM Identifier: NCT02013128.
The Lymphoma Academic Research Organisation. Bruton's tyrosine kinase (BTK) inhibition in B-cell lymphomas (BIBLOS). In: ClinicalTrials.gov [Internet]. Bethesda (MD): National Library of Medicine (US). Jan. 21, 2014—[cited Apr. 15, 2014]. Available from: http://clinicaltrials.gov/ct2/show/NCT02055924 NLM Identifier: NCT02055924.
Tinmouth et al. Fludarabine in alkylator-resistant follicular non-Hodgkin's lymphoma. Leuk. Lymphoma 41(1-2):137-145 (2001).
Traxler et al., "Use of a pharmacophore model for the design of EGF-R tyrosine kinase inhibitors: 4-(phenylamino)pyrazolo[3,4-d]pyramidines," J Med Chem, 40(22):3601-16 (1997).
Uckun et al. Bruton's Tyrosine Kinase (BTK) as a Dual-Function Regulator of Apoptosis. Biochem. Pharmacology 56:683-691 (1998).
Uckun et al. The Anti-leukemic Bruton's Tyrosin Kinase Inhibitor a-cyano-β-hydroxy-β-mehyl-N-(2,5-dibromophenyl)Propenamide (LFM-A13)Prevents Fatal Thromboembolism. Leuk. Lymphoma 44(9):1569-1577 (2003).
Uckun et al., "Bruton's tyrosine kinase as a molecular target in treatment of leukemias and lymphomas as well as inflammatory disorders and autoimmunity," Expert Opin Ther Pat, 20(11):1-14 (2010).
Uckun et al., "Btk as a mediator of radiation-induced apoptosis in DT-40 lymphoma B cells," Science, 273(5278):1096-100 (1996).
Uckun et al., "In vivo pharmacokinetic features, toxicity profile, and chemosensitizing activity of alpha-cyano-beta-hydroxy-beta-methyl-N-(2,5-dibromophenyl)propenamide (LFM-A13), a novel antileukemic agent targeting Bruton's tyrosine kinase," Clin Cancer Res, 8(5):1224-33 (2002).
University of California, San Diego. A Phase Ib/II Study of Ibrutinib in Combination With GA101—Obinutuzumab in Previously Untreated Chronic Lymphocytic Leukemia (CLL) Patients Over 65 Years of Age or With Comorbidities That Preclude the Use of Chemotherapy Based Treatment. In: ClinicalTrials.gov [Internet]. Bethesda (MD): National Library of Medicine (US). Oct. 30, 2014 [cited Feb. 5, 2015] Available from: https://clinicaltrial.gov/ct2/show/NCT02315768?term=NCT02315768 NLM Identifier: NCT02315768.
Vasconcelos et al.,"Solid dispersions as strategy to improve oral bioavailability of poor water soluble drugs," Drug Discov Today, 12(23-24):1068-1075 (2007).
Vassilev et al. Bruton's Tyrosine Kinase as an Inhibitor of the Fas/CD95 Death-inducing Signaling Complex. J. Biol. Chem. 274(3):1646-1656 (1999).
Vassilev et al. Therapeutic Potential of Inhibiting Bruton's Tyrosine Kinase, (BTK). Current Pharmaceutical Design 10:1757-1766 (2004).
Vippagunta et al. Crystalline Solids, Advanced Drug Delivery Reviews, 48:3-26 (2001).
Vose. Mantle cell lymphoma: 2012 update on diagnosis, risk-stratification, and clinical management. Am. J. Hematol. 87(6):604-609 (Jun. 2012).
Wang et al. "Ibrutinib and rituximab are an efficacious and safe combination in relapsed mantle cell lymphoma: preliminary results from a Phase II clinical trial," Oral Abstract Session 624, 56th ASH Annual Meeting and Exposition (Dec. 6-9, 2014).
Wang et al. Targeting BTK with ibrutinib in relapsed or refractory mantel-cell lymphoma. N Engl J Med 369(6):507-516 (Aug. 8, 2013).
Wilkinson et al. Selective tyrosine kinase inhibitors. Expert Opin. Emerging Drugs 5(3):287-297 (2000).
Wilson et al., "The Bruton's tyrosine kinase (BTK) inhibitor, ibrutinib (PCI-32765), has preferential activity in the ABC subtype of relapsed/refractory de novo diffuse large B-cell lymphoma (DLBCL): interim results of a multicenter, open-label, phase 2 study," Blood 120:Abstract 686 (2012).
Witzens-Harig et al. Current treatment of mantle cell lymphoma: results of a national survey and consensus meeting. Ann Hematol. (Epub Aug. 29, 2012), 91(11):1765-1772 (Nov. 2012).
Witzig et al. Lenalidomide oral monotherapy produces durable responses in relapsed or refractory indolent non-Hodgkin's lymphoma. J. Clin. Oncol. 27:5404-5409 (Epub Oct. 5, 2009).
Wolff. Burger's Medicinal Chemistry and Drug Discovery. 5th Ed. Part 1, pp. 975-977 (1995).
Woyach et al., "Resistance Mechanisms for the Bruton's Tyrosine Kinase Inhibitor Ibrutinib," N Engl J Med, 370(24): 2286-2294 (2014).
Yamamoto et al. The Orally Available Spleen Tyrosine Kinase Inhibitor 2-[7-(3,4-Dimethoxyphenyl)-imidazo[1,2-c]pyrimidin-5-ylamino]-nicotinamide Dihydrochloride (BAY61-3606) Blocks Antigen-Induced Airway Inflammation in Rodents. J. Pharma. and Exp. Therapeutics 306(3):1174-1181 (2003).

(56) References Cited

OTHER PUBLICATIONS

Yang et al. Tyrosine kinase inhibition in diffuse large B-cell lymphoma: molecular basis for antitumor activity and drug resistance of dasatinib. Leukemia 22(9):1755-1766 (2008) [E-pub Jul. 3, 2008].

Yasuhiro et al., "ONO-WG-307, a novel, potent and selective inhibitor of Bruton's tyrosine kinase, in sustained inhibition of the Erk, Akt and PKD signaling pathways," 53rd American Society of Hematology Annual Meeting and Exposition, San Diego, CA, Poster #2021 (2011).

Zent et al. The Treatment of Recurrent/Refractory chronic Lymphocytic Leukemia/Small Lymphocytic Lymphoma (CLL) With Everolimus Results in Clinical Responses and Mobilization of CLL Cells Into the Circulation. Cancer 116(9):2201-2207 (2010).

Zhu et al., "Calpain inhibitor II induces caspase-dependent apoptosis in human acute lymphoblastic leukemia and non-Hodgkin's lymphoma cells as well as some solid tumor cells," Clin Cancer Res, 6:2456-63 (2000).

Zhu T., et al., "New Tablet Formulation of Lopinavir/Ritonavir is Bioequivalent to the Capsule at a Dose of 800/200 mg," Poster H-1894, 45th Interscience Conference on Antimicrobial Agents and Chemotherapy (ICAAC), Dec. 16-19, 2005, 4 pages.

Zvonicek et al., "First Crystal Structures of Pharmaceutical Ibrutinib: Systematic Solvate Screening and Characterization," Crystal Grwoth & Design, 17(6): 3116-3127 (2017). Ahead of print.

DSC Thermograms of Form A

TGA Thermogram of Form A

XRPD Pattern of Form B

Infrared (IR) spectrum of Form B

TGA Thermogram of Form B

XRPD Pattern of Form C

DSC Thermograms of Form C

TGA Thermogram of Form C

XRPD Pattern of Form E

Simulated XRPD Pattern of Form F

CRYSTALLINE FORMS OF A BRUTON'S TYROSINE KINASE INHIBITOR

RELATED APPLICATIONS

This application is a continuation of U.S. patent application Ser. No. 15/900,660, filed Feb. 20, 2018, which is a continuation of U.S. patent application Ser. No. 15/887,744, filed Feb. 2, 2018, which is a continuation of U.S. patent application Ser. No. 15/645,319, filed Jul. 10, 2017, which is a continuation of U.S. patent application Ser. No. 15/497,896, filed Apr. 26, 2017, now U.S. Pat. No. 9,725,455, issued Aug. 8, 2017, which is a continuation of U.S. application Ser. No. 15/386,118, filed Dec. 21, 2016, now U.S. Pat. No. 9,713,617, issued Jul. 25, 2017, which is a divisional of U.S. patent application Ser. No. 14/405,317, filed Dec. 3, 2014, now U.S. Pat. No. 9,540,382, issued Jan. 10, 2017, which is the U.S. National Stage application of PCT/US2013/043888, filed Jun. 3, 2013, which claims the benefit of U.S. provisional patent application No. 61/655,381 entitled "CRYSTALLINE FORMS OF A BRUTON'S TYROSINE KINASE INHIBITOR" filed Jun. 4, 2012, each of which is herein incorporated by reference in its entirety.

Described herein is the Bruton's tyrosine kinase (Btk) inhibitor 1-((R)-3-(4-amino-3-(4-phenoxyphenyl)-1H-pyrazolo[3,4-d]pyrimidin-1-yl)piperidin-1-yl)prop-2-en-1-one, including crystalline forms, solvates and pharmaceutically acceptable salts thereof, as well as pharmaceutical compositions that include the Btk inhibitor and methods of using the Btk inhibitor in the treatment of diseases or conditions that would benefit from inhibition of Btk activity.

BACKGROUND OF THE INVENTION

Bruton's tyrosine kinase (Btk), a member of the Tec family of non-receptor tyrosine kinases, is a key signaling enzyme expressed in all hematopoietic cells types except T lymphocytes and natural killer cells. Btk plays an essential role in the B-cell signaling pathway linking cell surface B-cell receptor (BCR) stimulation to downstream intracellular responses.

Btk is a key regulator of B-cell development, activation, signaling, and survival. In addition, Btk plays a role in a number of other hematopoetic cell signaling pathways, e.g., Toll like receptor (TLR) and cytokine receptor-mediated TNF-α production in macrophages, IgE receptor (Fcepsilon RI) signaling in Mast cells, inhibition of Fas/APO-1 apoptotic signaling in B-lineage lymphoid cells, and collagen-stimulated platelet aggregation.

1-((R)-3-(4-amino-3-(4-phenoxyphenyl)-1H-pyrazolo[3,4-d]pyrimidin-1-yl)piperidin-1-yl)prop-2-en-1-one is also known by its IUPAC name as 1-{(3R)-3-[4-amino-3-(4-phenoxyphenyl)-1H-pyrazolo[3,4-d]pyrimidin-1-yl]piperidin-1-yl}prop-2-en-1-one or 2-Propen-1-one, 1-[(3R)-3-[4-amino-3-(4-phenoxyphenyl)-1H-pyrazolo[3,4-d]pyrimidin-1-yl]-1-piperidinyl-, and has been given the USAN name, ibrutinib. The various names given for ibrutinib are used interchangeably herein.

SUMMARY OF THE INVENTION

Described herein is the Btk inhibitor 1-((R)-3-(4-amino-3-(4-phenoxyphenyl)-1H-pyrazolo[3,4-d]pyrimidin-1-yl)piperidin-1-yl)prop-2-en-1-one, including pharmaceutically acceptable solvates (including hydrates), polymorphs, and amorphous phases, and methods of uses thereof. Also described are pharmaceutically acceptable salts of the Btk inhibitor, including pharmaceutically acceptable solvates (including hydrates), polymorphs, and amorphous phases, and methods of uses thereof. 1-((R)-3-(4-Amino-3-(4-phenoxyphenyl)-1H-pyrazolo[3,4-d]pyrimidin-1-yl)piperidin-1-yl)prop-2-en-1-one, as well as the pharmaceutically acceptable salts thereof, are used in the manufacture of medicaments for the treatment of diseases or conditions that are associated with Btk activity. 1-((R)-3-(4-Amino-3-(4-phenoxyphenyl)-1H-pyrazolo[3,4-d]pyrimidin-1-yl)piperidin-1-yl)prop-2-en-1-one is an irreversible Btk inhibitor.

Also described herein are methods for preparing crystalline forms of 1-((R)-3-(4-amino-3-(4-phenoxyphenyl)-1H-pyrazolo[3,4-d]pyrimidin-1-yl)piperidin-1-yl)prop-2-en-1-one. Further described are pharmaceutical compositions that include the crystalline forms and methods of using the Btk inhibitor in the treatment of diseases or conditions (including diseases or conditions wherein irreversible inhibition of Btk provides therapeutic benefit to a mammal having the disease or condition).

In one embodiment is anhydrous 1-((R)-3-(4-amino-3-(4-phenoxyphenyl)-1H-pyrazolo[3,4-d]pyrimidin-1-yl)piperidin-1-yl)prop-2-en-1-one.

In another embodiment is crystalline anhydrous 1-((R)-3-(4-amino-3-(4-phenoxyphenyl)-1H-pyrazolo[3,4-d]pyrimidin-1-yl)piperidin-1-yl)prop-2-en-1-one.

In a further embodiment is amorphous anhydrous 1-((R)-3-(4-amino-3-(4-phenoxyphenyl)-1H-pyrazolo[3,4-d]pyrimidin-1-yl)piperidin-1-yl)prop-2-en-1-one.

In one aspect is a solvate of 1-((R)-3-(4-amino-3-(4-phenoxyphenyl)-1H-pyrazolo[3,4-d]pyrimidin-1-yl)piperidin-1-yl)prop-2-en-1-one.

In one embodiment is a solvate, wherein 1-((R)-3-(4-amino-3-(4-phenoxyphenyl)-1H-pyrazolo[3,4-d]pyrimidin-1-yl)piperidin-1-yl)prop-2-en-1-one is solvated with methyl isobutyl ketone (MIBK), toluene or methanol. In one embodiment is a solvate, wherein 1-((R)-3-(4-amino-3-(4-phenoxyphenyl)-1H-pyrazolo[3,4-d]pyrimidin-1-yl)piperidin-1-yl)prop-2-en-1-one is solvated with methyl isobutyl ketone (MIBK) or toluene. In one embodiment is a solvate, wherein 1-((R)-3-(4-amino-3-(4-phenoxyphenyl)-1H-pyrazolo[3,4-d]pyrimidin-1-yl)piperidin-1-yl)prop-2-en-1-one is solvated with methanol.

In a further embodiment, the solvate is anhydrous.

In another embodiment the solvate is crystalline.

In yet another embodiment the solvate is amorphous.

In one aspect, described herein is a crystalline Form A of 1-((R)-3-(4-amino-3-(4-phenoxyphenyl)-1H-pyrazolo[3,4-d]pyrimidin-1-yl)piperidin-1-yl)prop-2-en-1-one that has at least one of the following properties:

(a) an X-Ray powder diffraction (XRPD) pattern substantially the same as shown in FIG. 1;

(b) an X-ray powder diffraction (XRPD) pattern with characteristic peaks at 5.7±0.1° 2-Theta, 13.6±0.1° 2-Theta, 16.1±0.1° 2-Theta, 18.9±0.1° 2-Theta, 21.3±0.1° 2-Theta, and 21.6±0.1° 2-Theta;

(c) substantially the same X-ray powder diffraction (XRPD) pattern post storage at 40° C. and 75% RH for at least a week;

(d) substantially the same X-ray powder diffraction (XRPD) pattern post storage at 25° C. and 97% RH for at least a week;

(e) Infrared (IR) spectrum substantially similar to the one set forth in FIG. 2;

(f) Infrared (IR) spectrum weak peaks at about 1584 cm$^{-1}$, about 1240 cm$^{-1}$, about 1147 cm$^{-1}$, about 1134 cm$^{-1}$, about 1099 cm$^{-1}$, and about 1067 cm$^{-1}$;

(g) a DSC thermogram substantially similar to the one set forth in FIG. 3;

(h) a thermo-gravimetric analysis (TGA) thermogram substantially similar to the one set forth in FIG. 4;

(i) a DSC thermogram with an endotherm having an onset at about 154° C. and a peak at about 157° C. and an exotherm at about 159° C.;

(j) non-hygroscopicity;

(k) an observed aqueous solubility of about 0.013 mg/mL at about pH 8;

or (l) combinations thereof.

In some embodiments, the crystalline Form A has an X-Ray powder diffraction (XRPD) pattern substantially the same as shown in FIG. 1. In some embodiments, the crystalline Form A has an X-ray powder diffraction (XRPD) pattern with characteristic peaks at 5.7±0.1° 2-Theta, 13.6±0.1° 2-Theta, 16.1±0.1° 2-Theta, 18.9±0.1° 2-Theta, 21.3±0.1° 2-Theta, and 21.6±0.1° 2-Theta. In some embodiments, the crystalline Form A has substantially the same X-ray powder diffraction (XRPD) pattern post storage at 40° C. and 75% RH for at least a week. In some embodiments, the crystalline Form A has substantially the same X-ray powder diffraction (XRPD) pattern post storage at 25° C. and 97% RH for at least a week. In some embodiments, the crystalline Form A has an Infrared (IR) spectrum substantially similar to the one set forth in FIG. 2. In some embodiments, the crystalline Form A has an Infrared (IR) spectrum weak peaks at about 1584 $cm^{-1}$, about 1240 $cm^{-1}$, about 1147 $cm^{-1}$, about 1134 $cm^{-1}$, about 1099 $cm^{-1}$, and about 1067 $cm^{-1}$. In some embodiments, the crystalline Form A has a melting temperature of about 155-156° C. In some embodiments, the crystalline Form A has a DSC thermogram substantially similar to the one set forth in FIG. 3. In some embodiments, the crystalline Form A has a thermo-gravimetric analysis (TGA) thermogram substantially similar to the one set forth in FIG. 4. In some embodiments, the crystalline Form A has a DSC thermogram with an endotherm having an onset at about 154° C. and a peak at about 157° C. and an exotherm at about 159° C. In some embodiments, the crystalline Form A is non-hygroscopic. In some embodiments, the crystalline Form A has an observed aqueous solubility of about 0.013 mg/mL at about pH 8. In some embodiments, the crystalline Form A that is characterized as having properties (a), (b), (c), (d), (e), (f), (g), (h), (i), (j), and (k). In some embodiments, the crystalline Form A was obtained from ethyl acetate, isopropyl acetate, tetrahydrofuran, methyl isobutyl ketone (MIBK), methyl ethyl ketone (MEK), nitromethane, methanol, ethanol, acetonitrile, dioxane, methyl tert-butyl ether (MTBE), anisole, acetone, heptanes, a methanol/water mixture or an acetone/heptane mixture. In some embodiments, the crystalline Form A was obtained from a methanol/water mixture. In some embodiments, the crystalline Form A is unsolvated. In some embodiments, the crystalline Form A is anhydrous.

In one aspect, described herein is a crystalline Form B of 1-((R)-3-(4-amino-3-(4-phenoxyphenyl)-1H-pyrazolo[3,4-d]pyrimidin-1-yl)piperidin-1-yl)prop-2-en-1-one that has at least one of the following properties:

(a) an X-Ray powder diffraction (XRPD) pattern substantially the same as shown in FIG. 5;

(b) an X-ray powder diffraction (XRPD) pattern with characteristic peaks at 5.2±0.10 2-Theta, 10.2±0.1° 2-Theta, 16.5±0.1° 2-Theta, 18.5±0.1° 2-Theta, and 20.8±0.1° 2-Theta;

(c) substantially the same X-ray powder diffraction (XRPD) pattern post storage at 40° C. and 75% RH for at least a week;

(d) substantially the same X-ray powder diffraction (XRPD) pattern post storage at 25° C. and 97% RH for at least a week;

(e) Infrared (IR) spectrum substantially similar to the one set forth in FIG. 6;

(f) Infrared (IR) spectrum weak peaks at about about 1586 $cm^{-1}$, about 1573 $cm^{-1}$, about 1562 $cm^{-1}$, about 1229 $cm^{-1}$, about 1141 $cm^{-1}$, about 1103 $cm^{-1}$, about 1056 $cm^{-1}$, and about 1033 $cm^{-1}$;

(g) a DSC thermogram substantially similar to the one set forth in FIG. 7;

(h) a thermo-gravimetric analysis (TGA) thermogram substantially similar to the one set forth in FIG. 8;

(i) a DSC thermogram with an endotherm having an onset at about 99-106° C. and a peak at about 115-118° C.;

(j) an observed aqueous solubility of about 0.0096 mg/mL at a pH of about 7.42;

or (k) combinations thereof.

In some embodiments, the crystalline Form B has an an X-Ray powder diffraction (XRPD) pattern substantially the same as shown in FIG. 5. In some embodiments, the crystalline Form B has an an X-ray powder diffraction (XRPD) pattern with characteristic peaks at 5.2±0.1° 2-Theta, 10.2±0.10 2-Theta, 16.5±0.10 2-Theta, 18.5±0.10 2-Theta, and 20.8±0.10 2-Theta. In some embodiments, the crystalline Form B has an substantially the same X-ray powder diffraction (XRPD) pattern post storage at 40° C. and 75% RH for at least a week. In some embodiments, the crystalline Form B has an substantially the same X-ray powder diffraction (XRPD) pattern post storage at 25° C. and 97% RH for at least a week. In some embodiments, the crystalline Form B has an Infrared (IR) spectrum substantially similar to the one set forth in FIG. 6. In some embodiments, the crystalline Form B has an Infrared (IR) spectrum weak peaks at about 1586 $cm^{-1}$, about 1573 $cm^{-1}$, about 1562 $cm^{-1}$, about 1229 $cm^{-1}$, about 1141 $cm^{-1}$, about 1103 $cm^{-1}$, about 1056 $cm^{-1}$, and about 1033 $cm^{-1}$. In some embodiments, the crystalline Form B has a DSC thermogram substantially similar to the one set forth in FIG. 7. In some embodiments, the crystalline Form B has a thermogravimetric analysis (TGA) thermogram substantially similar to the one set forth in FIG. 8. In some embodiments, the crystalline Form B has a DSC thermogram with an endotherm having an onset at about 99-106° C. and a peak at about 115-118° C. In some embodiments, the crystalline Form B has an observed aqueous solubility of about 0.0096 mg/mL at a pH of about 7.42. In some embodiments, the crystalline Form B that is characterized as having properties (a), (b), (c), (d), (e), (f), (g), (h), (i), and (j). In some embodiments, the crystalline Form B was obtained from a mixture of methanol and water. In some embodiments, the crystalline Form B is unsolvated. In some embodiments, the crystalline Form B is anhydrous.

In one aspect, described herein is a crystalline Form C of 1-((R)-3-(4-amino-3-(4-phenoxyphenyl)-1H-pyrazolo[3,4-d]pyrimidin-1-yl)piperidin-1-yl)prop-2-en-1-one that has at least one of the following properties:

(a) an X-Ray powder diffraction (XRPD) pattern substantially the same as shown in FIG. 9;

(b) an X-ray powder diffraction (XRPD) pattern with characteristic peaks at 7.0±0.1° 2-Theta, 14.0±0.1° 2-Theta, 15.7±0.1° 2-Theta, 18.2±0.1° 2-Theta, 19.1±0.1° 2-Theta, 19.5±0.1° 2-Theta, 20.3±0.1° 2-Theta, 22.1±0.1° 2-Theta, and 22.9±0.1° 2-Theta;
(c) a DSC thermogram substantially similar to the one set forth in FIG. 10;
(d) a thermo-gravimetric analysis (TGA) thermogram substantially similar to the one set forth in FIG. 11;
(e) a DSC thermogram with an endotherm having an onset at about 134-135° C. and a peak at about 137-139° C.; or
(f) combinations thereof.

In some embodiments, the crystalline Form C has an X-Ray powder diffraction (XRPD) pattern substantially the same as shown in FIG. 9. In some embodiments, the crystalline Form C has an X-ray powder diffraction (XRPD) pattern with characteristic peaks at 7.0±0.1° 2-Theta, 14.0±0.10 2-Theta, 15.7±0.10 2-Theta, 18.2±0.10 2-Theta, 19.1±0.10 2-Theta, 19.5±0.10 2-Theta, 20.3±0.1° 2-Theta, 22.1±0.1° 2-Theta, and 22.9±0.1° 2-Theta. In some embodiments, the crystalline Form C has a DSC thermogram substantially similar to the one set forth in FIG. 10. In some embodiments, the crystalline Form C has a thermo-gravimetric analysis (TGA) thermogram substantially similar to the one set forth in FIG. 11. In some embodiments, the crystalline Form C has a DSC thermogram with an endotherm having an onset at about 134-135° C. and a peak at about 137-139° C. In some embodiments, the crystalline Form C that is characterized as having properties (a), (b), (c), (d), and (e). In some embodiments, the crystalline Form C was obtained from a mixture of methanol and water. In some embodiments, the crystalline Form C is unsolvated. In some embodiments, the crystalline Form C is anhydrous.

In one aspect, described herein is a crystalline Form D of 1-((R)-3-(4-amino-3-(4-phenoxyphenyl)-1H-pyrazolo[3,4-d]pyrimidin-1-yl)piperidin-1-yl)prop-2-en-1-one that has at least one of the following properties:
(a) an X-Ray powder diffraction (XRPD) pattern substantially the same as shown in FIG. 12;
(b) an X-ray powder diffraction (XRPD) pattern with characteristic peaks at 7.2±0.10 2-Theta, 8.0±0.1° 2-Theta, 9.2±0.1° 2-Theta, 14.5±0.1° 2-Theta, 18.5±0.1° 2-Theta, 19.5±0.10 2-Theta, 20.7±0.10 2-Theta, 21.0±0.10 2-Theta, 21.9±0.10 2-Theta, and 22.4±0.10 2-Theta;
(c) a thermo-gravimetric analysis (TGA) thermogram substantially similar to the one set forth in FIG. 13; or
(d) combinations thereof.

In some embodiments, the crystalline Form D has an X-Ray powder diffraction (XRPD) pattern substantially the same as shown in FIG. 12. In some embodiments, the crystalline Form D has an X-ray powder diffraction (XRPD) pattern with characteristic peaks at 7.2±0.1° 2-Theta, 8.0±0.10 2-Theta, 9.2±0.10 2-Theta, 14.5±0.10 2-Theta, 18.5±0.10 2-Theta, 19.5±0.10 2-Theta, 20.7±0.10 2-Theta, 21.0±0.10 2-Theta, 21.9±0.10 2-Theta, and 22.4±0.10 2-Theta. In some embodiments, the crystalline Form D has a thermo-gravimetric analysis (TGA) thermogram substantially similar to the one set forth in FIG. 13. In some embodiments, the crystalline Form D that is characterized as having properties (a), (b), and (c). In some embodiments, the crystalline Form D was obtained from methyl isobutyl ketone (MIBK). In some embodiments, the crystalline Form D is solvated. In some embodiments, the crystalline Form D is solvated with methyl isobutyl ketone (MIBK).

In one aspect, described herein is a crystalline Form E of 1-((R)-3-(4-amino-3-(4-phenoxyphenyl)-1H-pyrazolo[3,4-d]pyrimidin-1-yl)piperidin-1-yl)prop-2-en-1-one that has at least one of the following properties:
(a) an X-Ray powder diffraction (XRPD) pattern substantially the same as shown in FIG. 14;
(b) an X-ray powder diffraction (XRPD) pattern with characteristic peaks at 7.8±0.10 2-Theta, 8.8±0.1° 2-Theta, 16.1±0.10 2-Theta, 18.1±0.10 2-Theta, 19.3±0.10 2-Theta, 19.5±0.10 2-Theta, 20.5±0.10 2-Theta, 21.6±0.10 2-Theta, and 25.2±0.10 2-Theta;
(c) a DSC thermogram substantially similar to the one set forth in FIG. 15;
(d) a thermo-gravimetric analysis (TGA) thermogram substantially similar to the one set forth in FIG. 15; or
(e) combinations thereof.

In some embodiments, the crystalline Form E has an X-Ray powder diffraction (XRPD) pattern substantially the same as shown in FIG. 14. In some embodiments, the crystalline Form E has an X-ray powder diffraction (XRPD) pattern with characteristic peaks at 7.8±0.1° 2-Theta, 8.8±0.1° 2-Theta, 16.1±0.10 2-Theta, 18.1±0.10 2-Theta, 19.3±0.10 2-Theta, 19.5±0.10 2-Theta, 20.5±0.10 2-Theta, 21.6±0.10 2-Theta, and 25.2±0.10 2-Theta. In some embodiments, the crystalline Form E has a DSC thermogram substantially similar to the one set forth in FIG. 15. In some embodiments, the crystalline Form E has a thermo-gravimetric analysis (TGA) thermogram substantially similar to the one set forth in FIG. 15. In some embodiments, the crystalline Form E that is characterized as having properties (a), (b), (c), and (d). In some embodiments, the crystalline Form E was obtained from toluene. In some embodiments, the crystalline Form E is solvated. In some embodiments, the crystalline Form E is solvated with toluene.

In one aspect, described herein is a crystalline Form F of 1-((R)-3-(4-amino-3-(4-phenoxyphenyl)-1H-pyrazolo[3,4-d]pyrimidin-1-yl)piperidin-1-yl)prop-2-en-1-one that has at least one of the following properties:
(a) an X-Ray powder diffraction (XRPD) pattern substantially the same as shown in FIG. 16;
(b) an X-ray powder diffraction (XRPD) pattern with characteristic peaks at 6.2±0.1° 2-Theta, 10.1±0.1° 2-Theta, 17.6±0.1° 2-Theta, 18.6±0.1° 2-Theta, 20.0±0.1° 2-Theta, 20.4±0.10 2-Theta, 20.7±0.10 2-Theta, 22.4±0.10 2-Theta, 23.0±0.10 2-Theta, 23.2±0.10 2-Theta, 24.4±0.10 2-Theta, 25.1±0.10 2-Theta, 27.6±0.10 2-Theta, 29.3±0.10 2-Theta, and 29.7±0.10 2-Theta;
(c) unit cell parameters substantially equal to the following at 100(2) K:

| Crystal system | | | Triclinic | | |
|---|---|---|---|---|---|
| Space group | P1 | a | 9.6332(3) Å | α | 105.762(3)° |
| | | b | 9.7536(4) Å | β | 95.132(2)° |
| | | c | 15.0592(4) Å | γ | 111.332(3)° |
| V | | | 1240.15(7) Å$^3$ | | |
| Z | | | 1 | | |
| Density (calculated) | | | 1.308 Mg/m$^3$ | | |
| Absorption coefficient | | | 0.726 mm$^{-1}$ | | |
| Wavelength | | | 1.54178 Å | | |
| F(000) | | | 518 | | | or
(d) combinations thereof.

In some embodiments, crystalline Form F has an X-Ray powder diffraction (XRPD) pattern substantially the same as shown in FIG. 16. In some embodiments, crystalline Form F has an X-ray powder diffraction (XRPD) pattern with characteristic peaks at 6.2±0.1° 2-Theta, 10.1±0.10 2-Theta, 17.6±0.10 2-Theta, 18.6±0.10 2-Theta, 20.0±0.10 2-Theta, 20.4±0.10 2-Theta, 20.7±0.10 2-Theta, 22.4±0.10 2-Theta, 23.0±0.10 2-Theta, 23.2±0.10 2-Theta, 24.4±0.10 2-Theta, 25.1±0.1° 2-Theta, 27.6±0.1° 2-Theta, 29.3±0.1° 2-Theta, and 29.7±0.10 2-Theta.

In some embodiments, crystalline Form F has unit cell parameters substantially equal to the following at 100(2) K:

| Crystal system | | | Triclinic | | |
|---|---|---|---|---|---|
| Space group | P1 | a | 9.6332(3) Å | α | 105.762(3)° |
| | | b | 9.7536(4) Å | β | 95.132(2)° |
| | | c | 15.0592(4) Å | γ | 111.332(3)° |
| V | | | 1240.15(7) Å$^3$ | | |
| Z | | | 1 | | |
| Density (calculated) | | | 1.308 Mg/m$^3$ | | |
| Absorption coefficient | | | 0.726 mm$^{-1}$ | | |
| Wavelength | | | 1.54178 Å | | |
| F(000) | | | 518 | | |

In some embodiments, crystalline Form F was obtained from methanol.

In some embodiments, crystalline Form F is solvated. In some embodiments, crystalline Form F is solvated with methanol.

In one aspect, described herein is a pharmaceutically acceptable salt of 1-((R)-3-(4-amino-3-(4-phenoxyphenyl)-1H-pyrazolo[3,4-d]pyrimidin-1-yl)piperidin-1-yl)prop-2-en-1-one, wherein the pharmaceutically acceptable salt is an acid addition salt. In some embodiments, the pharmaceutically acceptable salt is amorphous. In some embodiments, the pharmaceutically acceptable salt is crystalline.

In a further aspect are provided pharmaceutical compositions, which include 1-((R)-3-(4-amino-3-(4-phenoxyphenyl)-1H-pyrazolo[3,4-d]pyrimidin-1-yl)piperidin-1-yl)prop-2-en-1-one as described herein, and at least one additional ingredient selected from pharmaceutically acceptable carriers, diluents and excipients. In some embodiments, the pharmaceutical composition comprises Form A. In some embodiments, the pharmaceutical composition comprises Form B. In some embodiments, the pharmaceutical composition comprises Form C. In some embodiments, the pharmaceutical composition comprises Form D. In some embodiments, the pharmaceutical composition comprises Form E. In some embodiments, the pharmaceutical composition comprises Form F. In some embodiments, the pharmaceutical composition is in a form suitable for oral administration to a mammal. In some embodiments, the pharmaceutical composition is an oral solid dosage form. In some embodiments, the pharmaceutical composition comprises about 0.5 mg to about 1000 mg of crystalline 1-((R)-3-(4-amino-3-(4-phenoxyphenyl)-1H-pyrazolo[3,4-d]pyrimidin-1-yl)piperidin-1-yl)prop-2-en-1-one.

In another aspect, provided herein is a pharmaceutical formulation for oral administration comprising:
(a) about 40 mgs to about 200 mgs of 1-((R)-3-(4-amino-3-(4-phenoxyphenyl)-1H-pyrazolo[3,4-d]pyrimidin-1-yl)piperidin-1-yl)prop-2-en-1-one;
(b) about 40 wt % to about 50 wt % of a diluent;
(c) about 3 wt % to about 10 wt % of a disintegrating agent;
(d) about 2 wt % to about 7 wt % of a surfactant; and
(e) about 0.2 wt % to about 1.0 wt % of a lubricant.

In some embodiments, the diluent is selected from the group consisting of lactose, sucrose, dextrose, dextrates, maltodextrin, mannitol, xylitol, sorbitol, cyclodextrins, calcium phosphate, calcium sulfate, starches, modified starches, microcrystalline cellulose, microcellulose, and talc. In some embodiments the diluent is microcrystalline cellulose. In some embodiments, the disintegrating agent is selected from the group consisting of natural starch, a pregelatinized starch, a sodium starch, methylcrystalline cellulose, methylcellulose, croscarmellose, croscarmellose sodium, cross-linked sodium carboxymethylcellulose, cross-linked carboxymethylcellulose, cross-linked croscarmellose, cross-linked starch such as sodium starch glycolate, cross-linked polymer such as crospovidone, cross-linked polyvinylpyrrolidone, sodium alginate, a clay, or a gum. In some embodiments, the disintegrating agent is croscarmellose sodium. In some embodiments, the surfactant is selected from the group consisting of sodium lauryl sulfate, sorbitan monooleate, polyoxyethylene sorbitan monooleate, polysorbates, polaxomers, bile salts, glyceryl monostearate, copolymers of ethylene oxide and propylene oxide. In some embodiments, the surfactant is sodium lauryl sulfate. In some embodiments, the lubricant is selected from the group consisting of stearic acid, calcium hydroxide, talc, corn starch, sodium stearyl fumerate, stearic acid, sodium stearates, magnesium stearate, zinc stearate, and waxes. In some embodiments, the lubricant is magnesium stearate.

In some embodiments, provided herein is a pharmaceutical formulation for oral administration comprising:
(a) about 40 mgs to about 200 mgs of 1-((R)-3-(4-amino-3-(4-phenoxyphenyl)-1H-pyrazolo[3,4-d]pyrimidin-1-yl)piperidin-1-yl)prop-2-en-1-one;
(b) about 40 wt % to about 50 wt % of microcrystalline cellulose;
(c) about 3 wt % to about 10 wt % of croscarmellose sodium;
(d) about 2 wt % to about 7 wt % of sodium lauryl sulfate; and
(e) about 0.2 wt % to about 1.0 wt % of magnesium stearate.

In some embodiments, provided herein is a pharmaceutical formulation for oral administration comprising:
(a) about 40 wt % to about 50 wt % of 1-((R)-3-(4-amino-3-(4-phenoxyphenyl)-1H-pyrazolo[3,4-d]pyrimidin-1-yl)piperidin-1-yl)prop-2-en-1-one;
(b) about 40 wt % to about 50 wt % of microcrystalline cellulose;
(c) about 3 wt % to about 10 wt % of croscarmellose sodium;
(d) about 2 wt % to about 7 wt % of sodium lauryl sulfate; and
(e) about 0.2 wt % to about 1.0 wt % of magnesium stearate.

In some embodiments, provided herein is a pharmaceutical formulation for oral administration comprising:
(a) 140 mgs of 1-((R)-3-(4-amino-3-(4-phenoxyphenyl)-1H-pyrazolo[3,4-d]pyrimidin-1-yl)piperidin-1-yl)prop-2-en-1-one;
(b) 45.9 wt % of microcrystalline cellulose;
(c) 7.0 wt % of croscarmellose sodium;
(d) 4.2 wt % of sodium lauryl sulfate; and
(e) 0.5 wt % of magnesium stearate.

In some embodiments, provided herein is a pharmaceutical formulation for oral administration comprising:
(a) 140 mgs of 1-((R)-3-(4-amino-3-(4-phenoxyphenyl)-1H-pyrazolo[3,4-d]pyrimidin-1-yl)piperidin-1-yl)prop-2-en-1-one;
(b) 151.4 mgs of microcrystalline cellulose;
(c) 23.0 mgs of croscarmellose sodium;

(d) 14.0 mgs of sodium lauryl sulfate; and (e) 1.6 mgs of magnesium stearate.

In another aspect, provided herein is a pharmaceutical formulation for oral administration comprising:

(a) about 40 mgs to about 200 mgs of crystalline 1-((R)-3-(4-amino-3-(4-phenoxyphenyl)-1H-pyrazolo[3,4-d]pyrimidin-1-yl)piperidin-1-yl)prop-2-en-1-one;

(b) about 40 wt % to about 50 wt % of a diluent;

(c) about 3 wt % to about 10 wt % of a disintegrating agent;

(d) about 2 wt % to about 7 wt % of a surfactant; and (e) about 0.2 wt % to about 1.0 wt % of a lubricant.

In some embodiments, the diluent is selected from the group consisting of lactose, sucrose, dextrose, dextrates, maltodextrin, mannitol, xylitol, sorbitol, cyclodextrins, calcium phosphate, calcium sulfate, starches, modified starches, microcrystalline cellulose, microcellulose, and talc. In some embodiments the diluent is microcrystalline cellulose. In some embodiments, the disintegrating agent is selected from the group consisting of natural starch, a pregelatinized starch, a sodium starch, methylcrystalline cellulose, methylcellulose, croscarmellose, croscarmellose sodium, cross-linked sodium carboxymethylcellulose, cross-linked carboxymethylcellulose, cross-linked croscarmellose, cross-linked starch such as sodium starch glycolate, cross-linked polymer such as crospovidone, cross-linked polyvinylpyrrolidone, sodium alginate, a clay, or a gum. In some embodiments, the disintegrating agent is croscarmellose sodium. In some embodiments, the surfactant is selected from the group consisting of sodium lauryl sulfate, sorbitan monooleate, polyoxyethylene sorbitan monooleate, polysorbates, polaxomers, bile salts, glyceryl monostearate, copolymers of ethylene oxide and propylene oxide. In some embodiments, the surfactant is sodium lauryl sulfate. In some embodiments, the lubricant is selected from the group consisting of stearic acid, calcium hydroxide, talc, corn starch, sodium stearyl fumerate, stearic acid, sodium stearates, magnesium stearate, zinc stearate, and waxes. In some embodiments, the lubricant is magnesium stearate.

In some embodiments, provided herein is a pharmaceutical formulation for oral administration comprising:

(a) about 40 mgs to about 200 mgs of crystalline 1-((R)-3-(4-amino-3-(4-phenoxyphenyl)-1H-pyrazolo[3,4-d]pyrimidin-1-yl)piperidin-1-yl)prop-2-en-1-one;

(b) about 40 wt % to about 50 wt % of microcrystalline cellulose;

(c) about 3 wt % to about 10 wt % of croscarmellose sodium;

(d) about 2 wt % to about 7 wt % of sodium lauryl sulfate; and (e) about 0.2 wt % to about 1.0 wt % of magnesium stearate.

In some embodiments, provided herein is a pharmaceutical formulation for oral administration comprising:

(a) about 40 wt % to about 50 wt % of crystalline 1-((R)-3-(4-amino-3-(4-phenoxyphenyl)-1H-pyrazolo[3,4-d]pyrimidin-1-yl)piperidin-1-yl)prop-2-en-1-one;

(b) about 40 wt % to about 50 wt % of microcrystalline cellulose;

(c) about 3 wt % to about 10 wt % of croscarmellose sodium;

(d) about 2 wt % to about 7 wt % of sodium lauryl sulfate; and (e) about 0.2 wt % to about 1.0 wt % of magnesium stearate.

In some embodiments, provided herein is a pharmaceutical formulation for oral administration comprising:

(a) 140 mgs of crystalline 1-((R)-3-(4-amino-3-(4-phenoxyphenyl)-1H-pyrazolo[3,4-d]pyrimidin-1-yl)piperidin-1-yl)prop-2-en-1-one;

(b) 45.9 wt % of microcrystalline cellulose;

(c) 7.0 wt % of croscarmellose sodium;

(d) 4.2 wt % of sodium lauryl sulfate; and (e) 0.5 wt % of magnesium stearate.

In some embodiments, provided herein is a pharmaceutical formulation for oral administration comprising:

(a) 140 mgs of crystalline 1-((R)-3-(4-amino-3-(4-phenoxyphenyl)-1H-pyrazolo[3,4-d]pyrimidin-1-yl)piperidin-1-yl)prop-2-en-1-one;

(b) 151.4 mgs of microcrystalline cellulose;

(c) 23.0 mgs of croscarmellose sodium;

(d) 14.0 mgs of sodium lauryl sulfate; and (e) 1.6 mgs of magnesium stearate.

In some embodiments of the aforementioned pharmaceutical formulation embodiments, crystalline 1-((R)-3-(4-amino-3-(4-phenoxyphenyl)-1H-pyrazolo[3,4-d]pyrimidin-1-yl)piperidin-1-yl)prop-2-en-1-one is crystalline Form A. In some embodiments of the aforementioned pharmaceutical formulation embodiments, crystalline 1-((R)-3-(4-amino-3-(4-phenoxyphenyl)-1H-pyrazolo[3,4-d]pyrimidin-1-yl)piperidin-1-yl)prop-2-en-1-one is crystalline Form B. In some embodiments of the aforementioned pharmaceutical formulation embodiments, crystalline 1-((R)-3-(4-amino-3-(4-phenoxyphenyl)-1H-pyrazolo[3,4-d]pyrimidin-1-yl)piperidin-1-yl)prop-2-en-1-one is crystalline Form C. In some embodiments of the aforementioned pharmaceutical formulation embodiments, crystalline 1-((R)-3-(4-amino-3-(4-phenoxyphenyl)-1H-pyrazolo[3,4-d]pyrimidin-1-yl)piperidin-1-yl)prop-2-en-1-one is crystalline Form D. In some embodiments of the aforementioned pharmaceutical formulation embodiments, crystalline 1-((R)-3-(4-amino-3-(4-phenoxyphenyl)-1H-pyrazolo[3,4-d]pyrimidin-1-yl)piperidin-1-yl)prop-2-en-1-one is crystalline Form E. In some embodiments of the aforementioned pharmaceutical formulation embodiments, crystalline 1-((R)-3-(4-amino-3-(4-phenoxyphenyl)-1H-pyrazolo[3,4-d]pyrimidin-1-yl)piperidin-1-yl)prop-2-en-1-one is crystalline Form F. In some embodiments of the aforementioned pharmaceutical formulation embodiments, crystalline 1-((R)-3-(4-amino-3-(4-phenoxyphenyl)-1H-pyrazolo[3,4-d]pyrimidin-1-yl)piperidin-1-yl)prop-2-en-1-one is a mixture of two or more crystalline forms selected from the group consisting of Form A, Form B, Form C, Form D, Form E, and Form F. In another embodiment of the aforementioned pharmaceutical formulation embodiments provided herein, is a pharmaceutical formulation wherein the dosage form is a hard gelatin capsule.

In another aspect, provided herein is a pharmaceutical formulation for oral administration comprising:

(a) about 40 mgs to about 200 mgs of crystalline Form A of 1-((R)-3-(4-amino-3-(4-phenoxyphenyl)-1H-pyrazolo[3,4-d]pyrimidin-1-yl)piperidin-1-yl)prop-2-en-1-one;

(b) about 40 wt % to about 50 wt % of a diluent;

(c) about 3 wt % to about 10 wt % of a disintegrating agent;

(d) about 2 wt % to about 7 wt % of a surfactant; and (e) about 0.2 wt % to about 1.0 wt % of a lubricant.

In some embodiments, the diluent is selected from the group consisting of lactose, sucrose, dextrose, dextrates, maltodextrin, mannitol, xylitol, sorbitol, cyclodextrins, calcium phosphate, calcium sulfate, starches, modified starches, microcrystalline cellulose, microcellulose, and talc. In some embodiments the diluent is microcrystalline cellulose. In some embodiments, the disintegrating agent is selected from the group consisting of natural starch, a pregelatinized starch, a sodium starch, methylcrystalline cellulose, methylcellulose, croscarmellose, croscarmellose sodium, cross-linked sodium carboxymethylcellulose, cross-linked carboxymethylcellulose, cross-linked croscarmellose, cross-linked starch such as sodium starch glycolate, cross-linked polymer such as crospovidone, cross-linked polyvinylpyrrolidone, sodium alginate, a clay, or a gum. In some embodiments, the disintegrating agent is croscarmellose sodium. In some embodiments, the surfactant is selected from the group consisting of sodium lauryl sulfate, sorbitan monooleate, polyoxyethylene sorbitan monooleate, polysorbates, polaxomers, bile salts, glyceryl monostearate, copolymers of ethylene oxide and propylene oxide. In some embodiments, the surfactant is sodium lauryl sulfate. In some embodiments, the lubricant is selected from the group consisting of stearic acid, calcium hydroxide, talc, corn starch, sodium stearyl fumerate, stearic acid, sodium stearates, magnesium stearate, zinc stearate, and waxes. In some embodiments, the lubricant is magnesium stearate.

In some embodiments, provided herein is a pharmaceutical formulation for oral administration comprising:
(a) about 40 mgs to about 200 mgs of crystalline Form A of 1-((R)-3-(4-amino-3-(4-phenoxyphenyl)-1H-pyrazolo[3,4-d]pyrimidin-1-yl)piperidin-1-yl)prop-2-en-1-one;
(b) about 40 wt % to about 50 wt % of microcrystalline cellulose;
(c) about 3 wt % to about 10 wt % of croscarmellose sodium;
(d) about 2 wt % to about 7 wt % of sodium lauryl sulfate; and
(e) about 0.2 wt % to about 1.0 wt % of magnesium stearate.

In some embodiments, provided herein is a pharmaceutical formulation for oral administration comprising:
(a) about 40 wt % to about 50 wt % of crystalline Form A of 1-((R)-3-(4-amino-3-(4-phenoxyphenyl)-1H-pyrazolo[3,4-d]pyrimidin-1-yl)piperidin-1-yl)prop-2-en-1-one;
(b) about 40 wt % to about 50 wt % of microcrystalline cellulose;
(c) about 3 wt % to about 10 wt % of croscarmellose sodium;
(d) about 2 wt % to about 7 wt % of sodium lauryl sulfate; and
(e) about 0.2 wt % to about 1.0 wt % of magnesium stearate.

In some embodiments, provided herein is a pharmaceutical formulation for oral administration comprising:
(a) 140 mgs of crystalline Form A of 1-((R)-3-(4-amino-3-(4-phenoxyphenyl)-1H-pyrazolo[3,4-d]pyrimidin-1-yl)piperidin-1-yl)prop-2-en-1-one;
(b) 45.9 wt % of microcrystalline cellulose;
(c) 7.0 wt % of croscarmellose sodium;
(d) 4.2 wt % of sodium lauryl sulfate; and
(e) 0.5 wt % of magnesium stearate.

In some embodiments, provided herein is a pharmaceutical formulation for oral administration comprising:
(a) 140 mgs of crystalline Form A of 1-((R)-3-(4-amino-3-(4-phenoxyphenyl)-1H-pyrazolo[3,4-d]pyrimidin-1-yl)piperidin-1-yl)prop-2-en-1-one;
(b) 151.4 mgs of microcrystalline cellulose;
(c) 23.0 mgs of croscarmellose sodium;
(d) 14.0 mgs of sodium lauryl sulfate; and
(e) 1.6 mgs of magnesium stearate.

In another aspect provided herein, is a pharmaceutical formulation comprising: a) about 40 mgs to about 200 mgs of 1-((R)-3-(4-amino-3-(4-phenoxyphenyl)-1H-pyrazolo[3,4-d]pyrimidin-1-yl)piperidin-1-yl)prop-2-en-1-one; b) about 40 wt % to about 50 wt % of a diluent; c) about 3 wt % to about 10 wt % of a disintegrating agent; d) about 2 wt % to about 7 wt % of a surfactant; and e) about 0.2 wt % to about 1.0 wt % of a lubricant; wherein the formulation is in a unit dosage form in a blister pack, and said blister pack comprises metal or plastic foil. In some embodiments, is a pharmaceutical formulation comprising: a) 140 mgs of 1-((R)-3-(4-amino-3-(4-phenoxyphenyl)-1H-pyrazolo[3,4-d]pyrimidin-1-yl)piperidin-1-yl)prop-2-en-1-one; b) 45.9 wt % of microcrystalline cellulose; c) 7.0 wt % of croscarmellose sodium; d) 4.2 wt % of sodium lauryl sulfate; and e) 0.5 wt % of magnesium stearate wherein the formulation is in a unit dosage form in a blister pack, and said blister pack comprises metal or plastic foil.

In another embodiment is a package comprising one or more discrete blister pockets, wherein each blister pocket comprises a unit dosage form comprising:
a) about 40 mgs to about 200 mgs of 1-((R)-3-(4-amino-3-(4-phenoxyphenyl)-1H-pyrazolo[3,4-d]pyrimidin-1-yl)piperidin-1-yl)prop-2-en-1-one;
b) about 40 wt % to about 50 wt % of a diluent; c) about 3 wt % to about 10 wt % of a disintegrating agent; d) about 2 wt % to about 7 wt % of a surfactant; and
e) about 0.2 wt % to about 1.0 wt % of a lubricant;
wherein each blister pocket comprises metal or plastic foil.

In another aspect provided herein, is a pharmaceutical formulation comprising: a) about 40 mgs to about 200 mgs of crystalline Form A of 1-((R)-3-(4-amino-3-(4-phenoxyphenyl)-1H-pyrazolo[3,4-d]pyrimidin-1-yl)piperidin-1-yl)prop-2-en-1-one; b) about 40 wt % to about 50 wt % of a diluent; c) about 3 wt % to about 10 wt % of a disintegrating agent; d) about 2 wt % to about 7 wt % of a surfactant; and e) about 0.2 wt % to about 1.0 wt % of a lubricant; wherein the formulation is in a unit dosage form in a blister pack, and said blister pack comprises metal or plastic foil. In some embodiments, is a pharmaceutical formulation comprising: a) 140 mgs of 1-((R)-3-(4-amino-3-(4-phenoxyphenyl)-1H-pyrazolo[3,4-d]pyrimidin-1-yl)piperidin-1-yl)prop-2-en-1-one; b) 45.9 wt % of microcrystalline cellulose; c) 7.0 wt % of croscarmellose sodium; d) 4.2 wt % of sodium lauryl sulfate; and e) 0.5 wt % of magnesium stearate wherein the formulation is in a unit dosage form in a blister pack, and said blister pack comprises metal or plastic foil.

In another embodiment is a package comprising one or more discrete blister pockets, wherein each blister pocket comprises a unit dosage form comprising:
a) about 40 mgs to about 200 mgs of crystalline Form A of 1-((R)-3-(4-amino-3-(4-phenoxyphenyl)-1H-pyrazolo[3,4-d]pyrimidin-1-yl)piperidin-1-yl)prop-2-en-1-one;
b) about 40 wt % to about 50 wt % of a diluent; c) about 3 wt % to about 10 wt % of a disintegrating agent; d) about 2 wt % to about 7 wt % of a surfactant; and
e) about 0.2 wt % to about 1.0 wt % of a lubricant;
wherein each blister pocket comprises metal or plastic foil.

In one embodiment, a kit is provided which contains a multiplicity of oral dosage forms, such as tablets or capsules, packaging such as a jar containing the oral dosage forms, and instructions for use to administer the oral dosage forms in accordance with the method described herein. Unit dose packaging such as blister packs provide a useful way of packaging the oral dosage form of the formulations described herein, and in other embodiments embody a kit when combined with instructions for use. In other embodiments, detailed product information are included with the instructions for use in the kit. Blister packaging is particularly useful with solid oral dosage forms and are in further embodiments useful for alternate day dosing schedules for example. In one embodiment, solid unit dosage forms of the formulations described herein included in a blister pack with instructions to administer one or more tablets or capsules on a daily basis so that the dosage of the formulations described herein are sufficiently administered. In another embodiment, solid unit dosage forms are included in a blister pack with instructions to administer one or more tablets or capsules on an alternate day basis so that the dosage per day is sufficiently administered.

In one aspect, provided herein are methods for treating a patient by administering Compound 1. In some embodiments, provided herein is a method of inhibiting the activity of tyrosine kinase(s), such as Btk, or of treating a disease, disorder, or condition, which would benefit from inhibition of tyrosine kinase(s), such as Btk, in a mammal, which includes administering to the mammal a therapeutically effective amount of Compound 1, or pharmaceutically acceptable salt, pharmaceutically active metabolite, pharmaceutically acceptable prodrug, or pharmaceutically acceptable solvate.

In another aspect, provided herein is the use of Compound 1 for inhibiting Bruton's tyrosine kinase (Btk) activity or for the treatment of a disease, disorder, or condition, which would benefit from inhibition of Bruton's tyrosine kinase (Btk) activity.

In some embodiments, crystalline Compound 1 is administered to a human.

In some embodiments, crystalline Compound 1 is orally administered.

In other embodiments, crystalline Compound 1 is used for the formulation of a medicament for the inhibition of tyrosine kinase activity. In some other embodiments, crystalline Compound 1 is used for the formulation of a medicament for the inhibition of Bruton's tyrosine kinase (Btk) activity.

In one aspect, provided herein is a method of treating cancer in a mammal comprising administering to the mammal a pharmaceutical composition described herein comprising Compound 1. In some embodiments, the cancer is a B cell malignancy. In some embodiments, the cancer is a B cell malignancy selected from chronic lymphocytic leukemia (CLL)/small lymphocytic lymphoma (SLL), mantle cell lymphoma (MCL), diffuse large B Cell lymphoma (DLBCL), and multiple myeloma. In some embodiments, the cancer is a lymphoma, leukemia or a solid tumor. In some embodiments, the cancer is diffuse large B cell lymphoma, follicular lymphoma, chronic lymphocytic lymphoma, chronic lymphocytic leukemia, B-cell prolymphocytic leukemia, lymphoplasmacytic lymphoma/ Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, where the subject is suffering from a cancer, an anti-cancer agent is administered to the subject in addition to one of the above-mentioned compounds. In one embodiment, the anti-cancer agent is an inhibitor of mitogen-activated protein kinase signaling In one aspect, provided herein is a method of treating an inflammatory or an autoimmune disease in a mammal comprising administering to the mammal a pharmaceutical composition described herein comprising Compound 1. In some embodiments, the inflammatory disease is asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis. In some embodiments, the autoimmune disease is inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease Sjögren's syndrome, multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behqet's disease, chronic fatigue, dysautonomia, endometriosis, interstitial cystitis, neuromyotonia, scleroderma, or vulvodynia Articles of manufacture including packaging material, Compound 1 within the packaging material, and a label that indicates that Compound 1 is used for inhibiting the activity of tyrosine kinase(s), such as Btk, are provided.

In a further aspect, provided herein is a method of treating an autoimmune disease in a mammal, comprising administering Compound 1 to the mammal.

In a further aspect, provided herein is a method of treating a heteroimmune disease or condition in a mammal, comprising administering Compound 1 to the mammal.

In a further aspect, provided herein is a method of treating an inflammatory disease in a mammal, comprising administering Compound 1 to the mammal.

In a further aspect, provided herein is a method of treating cancer in a mammal, comprising administering Compound 1 to the mammal.

In a further aspect, provided herein is a method of treating a thromboembolic disorder in a mammal, comprising administering Compound 1 to the mammal. Thromboembolic disorders include, but are not limited to, myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In another aspect are methods for modulating, including irreversibly inhibiting the activity of Btk or other tyrosine kinases, wherein the other tyrosine kinases share homology with Btk by having a cysteine residue (including a Cys 481 residue) that can form a covalent bond with Compound 1, in a mammal comprising administering to the mammal at least once an effective amount of Compound 1. In another aspect are methods for modulating, including including irreversibly inhibiting, the activity of Btk in a mammal comprising administering to the mammal at least once an effective amount of Compound 1. In another aspect are methods for treating Btk-dependent or Btk mediated conditions or diseases, comprising administering to the mammal at least once an effective amount of Compound 1.

In another aspect are methods for treating inflammation comprising administering to the mammal at least once an effective amount of Compound 1.

A further aspect are methods for the treatment of cancer comprising administering to the mammal at least once an effective amount of Compound 1. The type of cancer may include, but is not limited to, pancreatic cancer and other solid or hematological tumors.

In another aspect are methods for treating respiratory diseases comprising administering to the mammal at least once an effective amount of Compound 1. In a further embodiment of this aspect, the respiratory disease is asthma. In a further embodiment of this aspect, the respiratory disease includes, but is not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma.

In another aspect are methods for preventing rheumatoid arthritis and/or osteoarthritis comprising administering to the mammal at least once an effective amount of Compound 1.

In another aspect are methods for treating inflammatory responses of the skin comprising administering to the mammal at least once an effective amount of Compound 1. Such inflammatory responses of the skin include, by way of example, dermatitis, contact dermatitis, eczema, urticaria, rosacea, and scarring. In another aspect are methods for reducing psoriatic lesions in the skin, joints, or other tissues or organs, comprising administering to the mammal an effective amount of Compound 1.

In another aspect is the use of Compound 1 in the manufacture of a medicament for treating an inflammatory disease or condition in an animal in which the activity of Btk or other tyrosine kinases, wherein the other tyrosine kinases share homology with Btk by having a cysteine residue (including a Cys 481 residue) that can form a covalent bond with at least one irreversible inhibitor described herein, contributes to the pathology and/or symptoms of the disease or condition. In one embodiment of this aspect, the tyrosine kinase protein is Btk. In another or further embodiment of this aspect, the inflammatory disease or conditions are respiratory, cardiovascular, or proliferative diseases.

In any of the aforementioned aspects are further embodiments in which Compound 1 is (a) systemically administered to the mammal; (b) administered orally to the mammal; (c) intravenously administered to the mammal; (d) administered by inhalation; (e) administered by nasal administration; or (f) administered by injection to the mammal; (g) administered topically (dermal) to the mammal; (h) administered by ophthalmic administration; or (i) administered rectally to the mammal.

In any of the aforementioned aspects are further embodiments comprising single administration of Compound 1, including further embodiments in which Compound 1 is administered (i) once; (ii) multiple times over the span of one day; (iii) continually; or (iv) continuously.

In any of the aforementioned aspects are further embodiments comprising multiple administrations of Compound 1, including further embodiments in which (i) Compound 1 is administered in a single dose; (ii) the time between multiple administrations is every 6 hours; (iii) Compound 1 is administered to the mammal every 8 hours. In further or alternative embodiments, the method comprises a drug holiday, wherein the administration of Compound 1 is temporarily suspended or the dose of Compound 1 being administered is temporarily reduced; at the end of the drug holiday, dosing of Compound 1 is resumed. The length of the drug holiday can vary from 2 days to 1 year.

In some embodiments, in any of the embodiments disclosed herein (including methods, uses, formulations, combination therapy, etc.), Compound 1, or a pharmaceutically acceptable salt or solvate thereof, is: optically pure (i.e. greater than 99% chiral purity by HPLC). In some embodiments, in any of the embodiments disclosed herein (including methods, uses, formulations, combination therapy, etc.), Compound 1, or a pharmaceutically acceptable salt or solvate thereof, is replaced with: a) Compound 1, or a pharmaceutically acceptable salt or solvate thereof, of lower chiral purity; b) 1-((S)-3-(4-amino-3-(4-phenoxyphenyl)-1H-pyrazolo[3,4-d]pyrimidin-1-yl)piperidin-1-yl)prop-2-en-1-one, or a pharmaceutically acceptable salt or solvate thereof of any optical purity; or c) racemic 1-(3-(4-amino-3-(4-phenoxyphenyl)-1H-pyrazolo[3,4-d]pyrimidin-1-yl)piperidin-1-yl)prop-2-en-1-one, or a pharmaceutically acceptable salt or solvate thereof.

In any of the embodiments disclosed herein (including methods, uses, formulations, combination therapy, etc.), amorphous Compound 1 is used. In any of the embodiments disclosed herein (including methods, uses, formulations, combination therapy, etc.), crystalline Compound 1 is used. In any of the embodiments disclosed herein (including methods, uses, formulations, combination therapy, etc.), crystalline Compound 1 (Form A) is used. In any of the embodiments disclosed herein (including methods, uses, formulations, combination therapy, etc.), crystalline Compound 1 (Form B) is used. In any of the embodiments disclosed herein (including methods, uses, formulations, combination therapy, etc.), crystalline Compound 1 (Form C) is used. In any of the embodiments disclosed herein (including methods, uses, formulations, combination therapy, etc.), crystalline Compound 1 (Form D) is used. In any of the embodiments disclosed herein (including methods, uses, formulations, combination therapy, etc.), crystalline Compound 1 (Form E) is used. In any of the embodiments disclosed herein (including methods, uses, formulations, combination therapy, etc.), crystalline Compound 1 (Form F) is used.

In some embodiments, in any of the embodiments disclosed herein (including methods, uses, formulations, combination therapy, etc.), Compound 1, or a pharmaceutically acceptable salt thereof, is replaced with an active metabolite of Compound 1. In some embodiments, the active metabolite is in a crystalline form. In some embodiments, the active metabolite is in an amorphous phase. In further embodiments the metabolite is isolated. In some embodiments, in any of the embodiments disclosed herein (including methods, uses, formulations, combination therapy, etc.), Compound 1, or a pharmaceutically acceptable salt thereof, is replaced with a prodrug of Compound 1, or a deuterated analog of Compound 1, or a pharmaceutically acceptable salt thereof.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description. The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

INCORPORATION BY REFERENCE

All publications and patent applications mentioned in this specification are herein incorporated by reference to the extent applicable and relevant.

DETAILED DESCRIPTION OF THE INVENTION

Figure 1:
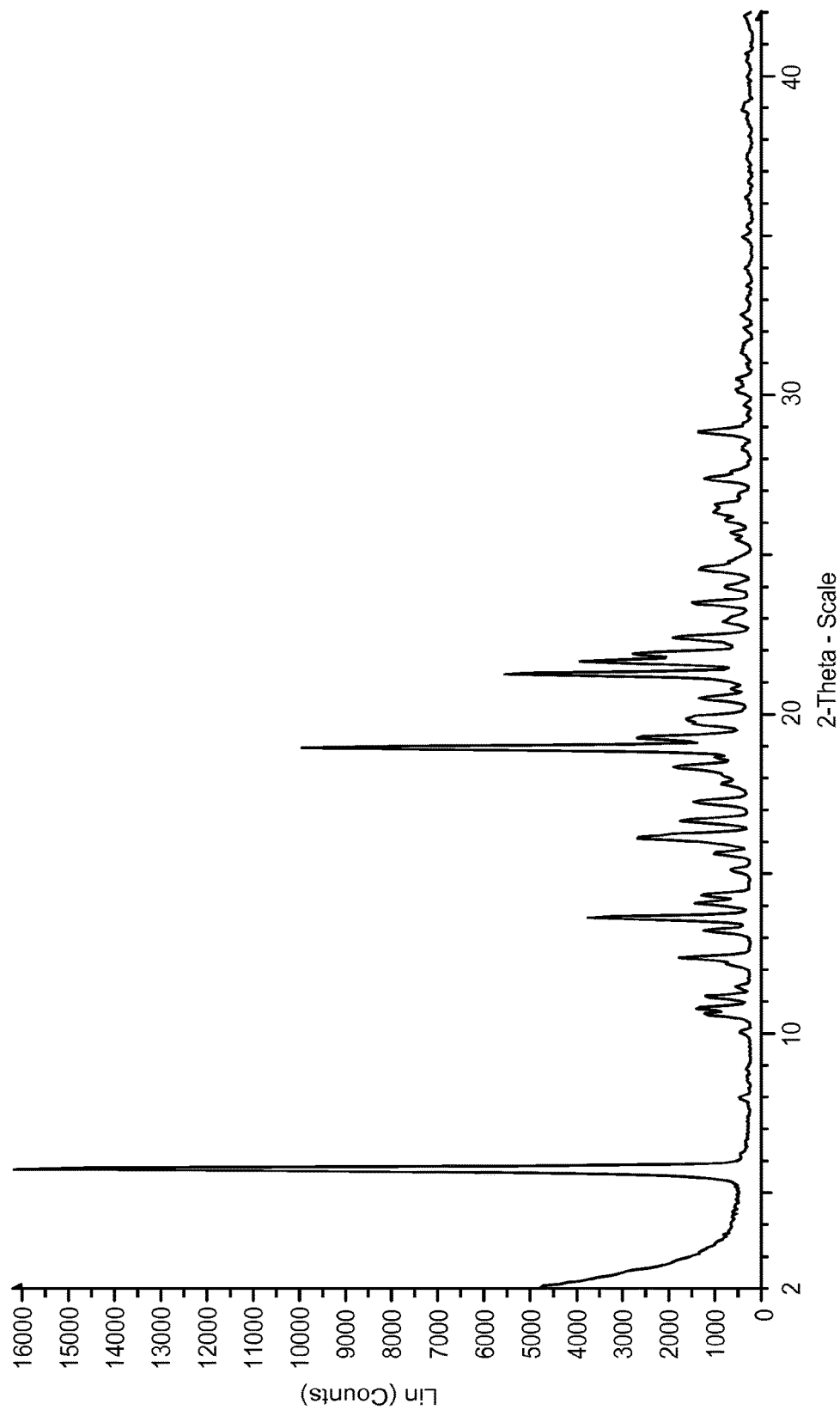
FIG. 1. Illustrates an X-Ray powder diffraction (XRPD) pattern of Form A.

The diverse roles played by Btk signaling in various hematopoietic cell functions, e.g., B-cell receptor activation, suggests that small molecule Btk inhibitors, such as Compound 1, are useful for reducing the risk of or treating a variety of diseases affected by or affecting many cell types of the hematopoetic lineage including, e.g., autoimmune diseases, heteroimmune conditions or diseases, inflammatory diseases, cancer (e.g., B-cell proliferative disorders), and thromboembolic disorders. Further, irreversible Btk inhibitor compounds, such as Compound 1, can be used to inhibit a small subset of other tyrosine kinases that share homology with Btk by having a cysteine residue (including a Cys 481 residue) that can form a covalent bond with the irreversible inhibitor.

In some embodiments, Compound 1 can be used in the treatment of an autoimmune disease in a mammal, which includes, but is not limited to, rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behqet's disease, chronic fatigue, dysautonomia, endometriosis, interstitial cystitis, neuromyotonia, scleroderma, and vulvodynia.

In some embodiments, Compound 1 can be used in the treatment of a heteroimmune disease or condition in a mammal, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, Compound 1 can be used in the treatment of an inflammatory disease in a mammal, which includes, but is not limited to asthma, inflammatory bowel disease, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

In yet other embodiments, the methods described herein can be used to treat a cancer, e.g., B-cell proliferative disorders, which include, but are not limited to diffuse large B cell lymphoma, follicular lymphoma, chronic lymphocytic lymphoma, chronic lymphocytic leukemia, B-cell prolymphocytic leukemia, lymphoplasmacytic lymphoma/ Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

In further embodiments, the methods described herein can be used to treat thromboembolic disorders, which include, but are not limited to myocardial infarct, angina pectoris (including unstable angina), reocclusions or restenoses after angioplasty or aortocoronary bypass, stroke, transitory ischemia, peripheral arterial occlusive disorders, pulmonary embolisms, and deep venous thromboses.

Hematological Malignancies

Disclosed herein, in certain embodiments, is a method for treating a hematological malignancy in an individual in need thereof, comprising: administering to the individual an amount of Compound 1.

In some embodiments, the hematological malignancy is a non-Hodgkin's lymphoma (NHL). In some embodiments, the hematological malignancy is a chronic lymphocytic leukemia (CLL), small lymphocytic lymphoma (SLL), high risk CLL, or a non-CLL/SLL lymphoma. In some embodiments, the hematological malignancy is follicular lymphoma (FL), diffuse large B-cell lymphoma (DLBCL), mantle cell lymphoma (MCL), Waldenstrom's macroglobulinemia, multiple myeloma (MM), marginal zone lymphoma, Burkitt's lymphoma, non-Burkitt high grade B cell lymphoma, or extranodal marginal zone B cell lymphoma. In some embodiments, the hematological malignancy is acute or chronic myelogenous (or myeloid) leukemia, myelodysplastic syndrome, acute lymphoblastic leukemia, or precursor B-cell acute lymphoblastic leukemia. In some embodiments, the hematological malignancy is chronic lymphocytic leukemia (CLL). In some embodiments, the hematological malignancy is mantle cell lymphoma (MCL). In some embodiments, the hematological malignancy is diffuse large B-cell lymphoma (DLBCL). In some embodiments, the hematological malignancy is diffuse large B-cell lymphoma (DLBCL), ABC subtype. In some embodiments, the hematological malignancy is diffuse large B-cell lymphoma (DLBCL), GCB subtype. In some embodiments, the hematological malignancy is Waldenstrom's macroglobulinemia (WM). In some embodiments, the hematological malignancy is multiple myeloma (MM). In some embodiments, the hematological malignancy is Burkitt's lymphoma. In some embodiments, the hematological malignancy is follicular lymphoma (FL). In some embodiments, the hematological malignancy is transformed follicular lymphoma. In some embodiments, the hematological malignancy is marginal zone lymphoma.

In some embodiments, the hematological malignancy is relapsed or refractory non-Hodgkin's lymphoma (NHL). In some embodiments, the hematological malignancy is relapsed or refractory diffuse large B-cell lymphoma (DLBCL), relapsed or refractory mantle cell lymphoma (MCL), relapsed or refractory follicular lymphoma (FL), relapsed or refractory CLL, relapsed or refractory SLL, relapsed or refractory multiple myeloma, relapsed or refractory Waldenstrom's macroglobulinemia, relapsed or refractory multiple myeloma (MM), relapsed or refractory marginal zone lymphoma, relapsed or refractory Burkitt's lymphoma, relapsed or refractory non-Burkitt high grade B cell lymphoma, relapsed or refractory extranodal marginal zone B cell lymphoma. In some embodiments, the hematological malignancy is a relapsed or refractory acute or chronic myelogenous (or myeloid) leukemia, relapsed or refractory myelodysplastic syndrome, relapsed or refractory acute lymphoblastic leukemia, or relapsed or refractory precursor B-cell acute lymphoblastic leukemia. In some embodiments, the hematological malignancy is relapsed or refractory chronic lymphocytic leukemia (CLL). In some embodiments, the hematological malignancy is relapsed or refractory mantle cell lymphoma (MCL). In some embodiments, the hematological malignancy is relapsed or refractory diffuse large B-cell lymphoma (DLBCL). In some embodiments, the hematological malignancy is relapsed or refractory diffuse large B-cell lymphoma (DLBCL), ABC subtype. In some embodiments, the hematological malignancy is relapsed or refractory diffuse large B-cell lymphoma (DLBCL), GCB subtype. In some embodiments, the hematological malignancy is relapsed or refractory Waldenstrom's macroglobulinemia (WM). In some embodiments, the hematological malignancy is relapsed or refractory multiple myeloma (MM). In some embodiments, the hematological malignancy is relapsed or refractory Burkitt's lymphoma. In some embodiments, the hematological malignancy is relapsed or refractory follicular lymphoma (FL).

In some embodiments, the hematological malignancy is a hematological malignancy that is classified as high-risk. In some embodiments, the hematological malignancy is high risk CLL or high risk SLL.

B-cell lymphoproliferative disorders (BCLDs) are neoplasms of the blood and encompass, inter alia, non-Hodgkin lymphoma, multiple myeloma, and leukemia. BCLDs can originate either in the lymphatic tissues (as in the case of lymphoma) or in the bone marrow (as in the case of leukemia and myeloma), and they all are involved with the uncontrolled growth of lymphocytes or white blood cells. There are many subtypes of BCLD, e.g., chronic lymphocytic leukemia (CLL) and non-Hodgkin lymphoma (NHL). The disease course and treatment of BCLD is dependent on the BCLD subtype; however, even within each subtype the clinical presentation, morphologic appearance, and response to therapy is heterogeneous.

Malignant lymphomas are neoplastic transformations of cells that reside predominantly within lymphoid tissues. Two groups of malignant lymphomas are Hodgkin's lymphoma and non-Hodgkin's lymphoma (NHL). Both types of lymphomas infiltrate reticuloendothelial tissues. However, they differ in the neoplastic cell of origin, site of disease, presence of systemic symptoms, and response to treatment (Freedman et al., "Non-Hodgkin's Lymphomas" Chapter 134, Cancer Medicine, (an approved publication of the American Cancer Society, B.C. Decker Inc., Hamilton, Ontario, 2003).

Non-Hodgkin's Lymphomas

Disclosed herein, in certain embodiments, is a method for treating a non-Hodgkin's lymphoma in an individual in need thereof, comprising: administering to the individual an amount of Compound 1.

Further disclosed herein, in certain embodiments, is a method for treating relapsed or refractory non-Hodgkin's lymphoma in an individual in need thereof, comprising: administering to the individual a therapeutically-effective amount of Compound 1. In some embodiments, the non-Hodgkin's lymphoma is relapsed or refractory diffuse large B-cell lymphoma (DLBCL), relapsed or refractory mantle cell lymphoma, relapsed or refractory follicular lymphoma, or relapsed or refractory CLL.

Non-Hodgkin lymphomas (NHL) are a diverse group of malignancies that are predominately of B-cell origin. NHL may develop in any organs associated with lymphatic system such as spleen, lymph nodes or tonsils and can occur at any age. NHL is often marked by enlarged lymph nodes, fever, and weight loss. NHL is classified as either B-cell or T-cell NHL. Lymphomas related to lymphoproliferative disorders following bone marrow or stem cell transplantation are usually B-cell NHL. In the Working Formulation classification scheme, NHL has been divided into low-, intermediate-, and high-grade categories by virtue of their natural histories (see "The Non-Hodgkin's Lymphoma Pathologic Classification Project," Cancer 49(1982):2112-2135). The low-grade lymphomas are indolent, with a median survival of 5 to 10 years (Horning and Rosenberg (1984) N. Engl. J. Med. 311:1471-1475). Although chemotherapy can induce remissions in the majority of indolent lymphomas, cures are rare and most patients eventually relapse, requiring further therapy. The intermediate- and high-grade lymphomas are more aggressive tumors, but they have a greater chance for cure with chemotherapy. However, a significant proportion of these patients will relapse and require further treatment.

A non-limiting list of the B-cell NHL includes Burkitt's lymphoma (e.g., Endemic Burkitt's Lymphoma and Sporadic Burkitt's Lymphoma), Cutaneous B-Cell Lymphoma, Cutaneous Marginal Zone Lymphoma (MZL), Diffuse Large Cell Lymphoma (DLBCL), Diffuse Mixed Small and Large Cell Lympoma, Diffuse Small Cleaved Cell, Diffuse Small Lymphocytic Lymphoma, Extranodal Marginal Zone B-cell lymphoma, follicular lymphoma, Follicular Small Cleaved Cell (Grade 1), Follicular Mixed Small Cleaved and Large Cell (Grade 2), Follicular Large Cell (Grade 3), Intravascular Large B-Cell Lymphoma, Intravascular Lymphomatosis, Large Cell Immunoblastic Lymphoma, Large Cell Lymphoma (LCL), Lymphoblastic Lymphoma, MALT Lymphoma, Mantle Cell Lymphoma (MCL), immunoblastic large cell lymphoma, precursor B-lymphoblastic lymphoma, mantle cell lymphoma, chronic lymphocytic leukemia (CLL)/small lymphocytic lymphoma (SLL), extranodal marginal zone B-cell lymphoma-mucosa-associated lymphoid tissue (MALT) lymphoma, Mediastinal Large B-Cell Lymphoma, nodal marginal zone B-cell lymphoma, splenic marginal zone B-cell lymphoma, primary mediastinal B-cell lymphoma, lymphoplasmocytic lymphoma, hairy cell leukemia, Waldenstrom's Macroglobulinemia, and primary central nervous system (CNS) lymphoma. Additional non-Hodgkin's lymphomas are contemplated within the scope of the present invention and apparent to those of ordinary skill in the art.

DLBCL

Disclosed herein, in certain embodiments, is a method for treating a DLCBL in an individual in need thereof, comprising: administering to the individual an amount of Compound 1. Further disclosed herein, in certain embodiments, is a method for treating relapsed or refractory DLCBL in an individual in need thereof, comprising: administering to the individual a therapeutically-effective amount of Compound 1.

As used herein, the term "Diffuse large B-cell lymphoma (DLBCL)" refers to a neoplasm of the germinal center B lymphocytes with a diffuse growth pattern and a high-intermediate proliferation index. DLBCLs represent approximately 30% of all lymphomas and may present with several morphological variants including the centroblastic, immunoblastic, T-cell/histiocyte rich, anaplastic and plasmoblastic subtypes. Genetic tests have shown that there are different subtypes of DLBCL. These subtypes seem to have different outlooks (prognoses) and responses to treatment. DLBCL can affect any age group but occurs mostly in older people (the average age is mid-60s).

Disclosed herein, in certain embodiments, is a method for treating diffuse large B-cell lymphoma, activated B cell-like subtype (ABC-DLBCL), in an individual in need thereof, comprising: administering to the individual an irreversible Btk inhibitor in an amount from 300 mg/day up to, and including, 1000 mg/day. The ABC subtype of diffuse large B-cell lymphoma (ABC-DLBCL) is thought to arise from post germinal center B cells that are arrested during plasmatic differentiation. The ABC subtype of DLBCL (ABC-DLBCL) accounts for approximately 30% total DLBCL diagnoses. It is considered the least curable of the DLBCL molecular subtypes and, as such, patients diagnosed with the ABC-DLBCL typically display significantly reduced survival rates compared with individuals with other types of DLCBL. ABC-DLBCL is most commonly associated with chromosomal translocations deregulating the germinal center master regulator BCL6 and with mutations inactivating the PRDM1 gene, which encodes a transcriptional repressor required for plasma cell differentiation.

A particularly relevant signaling pathway in the pathogenesis of ABC-DLBCL is the one mediated by the nuclear factor (NF)-κB transcription complex. The NF-κB family comprises 5 members (p50, p52, p65, c-rel and RelB) that form homo- and heterodimers and function as transcriptional factors to mediate a variety of proliferation, apoptosis, inflammatory and immune responses and are critical for normal B-cell development and survival. NF-κB is widely used by eukaryotic cells as a regulator of genes that control cell proliferation and cell survival. As such, many different types of human tumors have misregulated NF-κB: that is, NF-κB is constitutively active. Active NF-κB turns on the expression of genes that keep the cell proliferating and protect the cell from conditions that would otherwise cause it to die via apoptosis.

The dependence of ABC DLBCLs on NF-kB depends on a signaling pathway upstream of IkB kinase comprised of CARD11, BCL10 and MALT1 (the CBM complex). Interference with the CBM pathway extinguishes NF-kB signaling in ABC DLBCL cells and induces apoptosis. The molecular basis for constitutive activity of the NF-kB pathway is a subject of current investigation but some somatic alterations to the genome of ABC DLBCLs clearly invoke this pathway. For example, somatic mutations of the coiled-coil domain of CARD11 in DLBCL render this signaling scaffold protein able to spontaneously nucleate protein-protein interaction with MALT1 and BCL10, causing IKK activity and NF-kB activation. Constitutive activity of the B cell receptor signaling pathway has been implicated in the activation of NF-kB in ABC DLBCLs with wild type CARD11, and this is associated with mutations within the cytoplasmic tails of the B cell receptor subunits CD79A and CD79B. Oncogenic activating mutations in the signaling adapter MYD88 activate NF-kB and synergize with B cell receptor signaling in sustaining the survival of ABC DLBCL cells. In addition, inactivating mutations in a negative regulator of the NF-kB pathway, A20, occur almost exclusively in ABC DLBCL.

Indeed, genetic alterations affecting multiple components of the NF-κB signaling pathway have been recently identified in more than 50% of ABC-DLBCL patients, where these lesions promote constitutive NF-κB activation, thereby contributing to lymphoma growth. These include mutations of CARD11 (~10% of the cases), a lymphocyte-specific cytoplasmic scaffolding protein that—together with MALT1 and BCL10—forms the BCR signalosome, which relays signals from antigen receptors to the downstream mediators of NF-κB activation. An even larger fraction of cases (~30%) carry biallelic genetic lesions inactivating the negative NF-κB regulator A20. Further, high levels of expression of NF-κB target genes have been observed in ABC-DLBCL tumor samples. See, e.g., U. Klein et al., (2008), *Nature Reviews Immunology* 8:22-23; R. E. Davis et al., (2001), *Journal of Experimental Medicine* 194:1861-1874; G. Lentz et al., (2008), *Science* 319:1676-1679; M. Compagno et al., (2009), *Nature* 459:712-721; and L. Srinivasan et al., (2009), *Cell* 139:573-586).

DLBCL cells of the ABC subtype, such as OCI-Ly10, have chronic active BCR signalling and are very sensitive to the Btk inhibitor described herein. The irreversible Btk inhibitor described herein potently and irreversibly inhibits the growth of OCI-Ly10 ($EC_{50}$ continuous exposure=10 nM, $EC_{50}$ 1 hour pulse=50 nM). In addition, induction of apoptosis, as shown by capsase activation, Annexin-V flow cytometry and increase in sub-G0 fraction is observed in OCILy10. Both sensitive and resistant cells express Btk at similar levels, and the active site of Btk is fully occupied by the inhibitor in both as shown using a fluorescently labeled affinity probe. OCI-Ly10 cells are shown to have chronically active BCR signalling to NF-kB which is dose dependently inhibited by the Btk inhibitors described herein. The activity of Btk inhibitors in the cell lines studied herein are also characterized by comparing signal transduction profiles (Btk, PLCγ, ERK, NF-kB, AKT), cytokine secretion profiles and mRNA expression profiles, both with and without BCR stimulation, and observed significant differences in these profiles that lead to clinical biomarkers that identify the most sensitive patient populations to Btk inhibitor treatment. See U.S. Pat. No. 7,711,492 and Staudt et al., Nature, Vol. 463, Jan. 7, 2010, pp. 88-92, the contents of which are incorporated by reference in their entirety.

Follicular Lymphoma

Disclosed herein, in certain embodiments, is a method for treating a follicular lymphoma in an individual in need thereof, comprising: administering to the individual an amount of Compound 1. Further disclosed herein, in certain embodiments, is a method for treating relapsed or refractory follicular lymphoma in an individual in need thereof, comprising: administering to the individual a therapeutically-effective amount of Compound 1.

As used herein, the term "follicular lymphoma" refers to any of several types of non-Hodgkin's lymphoma in which the lymphomatous cells are clustered into nodules or follicles. The term follicular is used because the cells tend to grow in a circular, or nodular, pattern in lymph nodes. The average age for people with this lymphoma is about 60.

CLL/SLL

Disclosed herein, in certain embodiments, is a method for treating a CLL or SLL in an individual in need thereof, comprising: administering to the individual an amount of Compound 1. Further disclosed herein, in certain embodiments, is a method for treating relapsed or refractory CLL or SLL in an individual in need thereof, comprising: administering to the individual a therapeutically-effective amount of Compound 1.

Chronic lymphocytic leukemia and small lymphocytic lymphoma (CLL/SLL) are commonly thought as the same disease with slightly different manifestations. Where the cancerous cells gather determines whether it is called CLL or SLL. When the cancer cells are primarily found in the lymph nodes, lima bean shaped structures of the lymphatic system (a system primarily of tiny vessels found in the body), it is called SLL. SLL accounts for about 5% to 10% of all lymphomas. When most of the cancer cells are in the bloodstream and the bone marrow, it is called CLL.

Both CLL and SLL are slow-growing diseases, although CLL, which is much more common, tends to grow slower. CLL and SLL are treated the same way. They are usually not considered curable with standard treatments, but depending on the stage and growth rate of the disease, most patients live longer than 10 years. Occasionally over time, these slow-growing lymphomas may transform into a more aggressive type of lymphoma.

Chronic lymphoid leukemia (CLL) is the most common type of leukemia. It is estimated that 100,760 people in the United States are living with or are in remission from CLL. Most (>75%) people newly diagnosed with CLL are over the age of 50. Currently CLL treatment focuses on controlling the disease and its symptoms rather than on an outright cure. CLL is treated by chemotherapy, radiation therapy, biological therapy, or bone marrow transplantation. Symptoms are sometimes treated surgically (splenectomy removal of enlarged spleen) or by radiation therapy ("de-bulking" swollen lymph nodes). Though CLL progresses slowly in most cases, it is considered generally incurable. Certain CLLs are classified as high-risk. As used herein, "high risk CLL" means CLL characterized by at least one of the following 1) 17p13-; 2) 11q22-; 3) unmutated IgVH together with ZAP-70+ and/or CD38+; or 4) trisomy 12.

CLL treatment is typically administered when the patient's clinical symptoms or blood counts indicate that the disease has progressed to a point where it may affect the patient's quality of life.

Small lymphocytic leukemia (SLL) is very similar to CLL described supra, and is also a cancer of B-cells. In SLL the abnormal lymphocytes mainly affect the lymph nodes. However, in CLL the abnormal cells mainly affect the blood and the bone marrow. The spleen may be affected in both conditions. SLL accounts for about 1 in 25 of all cases of non-Hodgkin lymphoma. It can occur at any time from young adulthood to old age, but is rare under the age of 50. SLL is considered an indolent lymphoma. This means that the disease progresses very slowly, and patients tend to live many years after diagnosis. However, most patients are diagnosed with advanced disease, and although SLL responds well to a variety of chemotherapy drugs, it is generally considered to be incurable. Although some cancers tend to occur more often in one gender or the other, cases and deaths due to SLL are evenly split between men and women. The average age at the time of diagnosis is 60 years.

Although SLL is indolent, it is persistently progressive. The usual pattern of this disease is one of high response rates to radiation therapy and/or chemotherapy, with a period of disease remission. This is followed months or years later by an inevitable relapse. Re-treatment leads to a response again, but again the disease will relapse. This means that although the short-term prognosis of SLL is quite good, over time, many patients develop fatal complications of recurrent disease. Considering the age of the individuals typically diagnosed with CLL and SLL, there is a need in the art for a simple and effective treatment of the disease with minimum side-effects that do not impede on the patient's quality of life. The instant invention fulfills this long standing need in the art.

Mantle Cell Lymphoma

Disclosed herein, in certain embodiments, is a method for treating a Mantle cell lymphoma in an individual in need thereof, comprising: administering to the individual an amount of Compound 1. Further disclosed herein, in certain embodiments, is a method for treating relapsed or refractory Mantle cell lymphoma in an individual in need thereof, comprising: administering to the individual a therapeutically-effective amount of Compound 1.

As used herein, the term, "Mantle cell lymphoma" refers to a subtype of B-cell lymphoma, due to CD5 positive antigen-naive pregerminal center B-cell within the mantle zone that surrounds normal germinal center follicles. MCL cells generally over-express cyclin D1 due to a t(11:14) chromosomal translocation in the DNA. More specifically, the translocation is at t(11;14)(q13;q32). Only about 5% of lymphomas are of this type. The cells are small to medium in size. Men are affected most often. The average age of patients is in the early 60s. The lymphoma is usually widespread when it is diagnosed, involving lymph nodes, bone marrow, and, very often, the spleen. Mantle cell lymphoma is not a very fast growing lymphoma, but is difficult to treat.

Marginal Zone B-Cell Lymphoma

Disclosed herein, in certain embodiments, is a method for treating a marginal zone B-cell lymphoma in an individual in need thereof, comprising: administering to the individual an amount of Compound 1. Further disclosed herein, in certain embodiments, is a method for treating relapsed or refractory marginal zone B-cell lymphoma in an individual in need thereof, comprising: administering to the individual a therapeutically-effective amount of Compound 1.

As used herein, the term "marginal zone B-cell lymphoma" refers to a group of related B-cell neoplasms that involve the lymphoid tissues in the marginal zone, the patchy area outside the follicular mantle zone. Marginal zone lymphomas account for about 5% to 10% of lymphomas. The cells in these lymphomas look small under the microscope. There are 3 main types of marginal zone lymphomas including extranodal marginal zone B-cell lymphomas, nodal marginal zone B-cell lymphoma, and splenic marginal zone lymphoma.

MALT

Disclosed herein, in certain embodiments, is a method for treating a MALT in an individual in need thereof, comprising: administering to the individual an amount of Compound 1. Further disclosed herein, in certain embodiments, is a method for treating relapsed or refractory MALT in an individual in need thereof, comprising: administering to the individual a therapeutically-effective amount of Compound 1.

The term "mucosa-associated lymphoid tissue (MALT) lymphoma", as used herein, refers to extranodal manifestations of marginal-zone lymphomas. Most MALT lymphoma are a low grade, although a minority either manifest initially as intermediate-grade non-Hodgkin lymphoma (NHL) or evolve from the low-grade form. Most of the MALT lymphoma occur in the stomach, and roughly 70% of gastric MALT lymphoma are associated with *Helicobacter pylori* infection. Several cytogenetic abnormalities have been identified, the most common being trisomy 3 or t(11;18). Many of these other MALT lymphoma have also been linked to infections with bacteria or viruses. The average age of patients with MALT lymphoma is about 60.

Nodal Marginal Zone B-Cell Lymphoma

Disclosed herein, in certain embodiments, is a method for treating a nodal marginal zone B-cell lymphoma in an individual in need thereof, comprising: administering to the individual an amount of Compound 1. Further disclosed herein, in certain embodiments, is a method for treating relapsed or refractory nodal marginal zone B-cell lymphoma in an individual in need thereof, comprising: administering to the individual a therapeutically-effective amount of Compound 1.

The term "nodal marginal zone B-cell lymphoma" refers to an indolent B-cell lymphoma that is found mostly in the lymph nodes. The disease is rare and only accounts for 1% of all Non-Hodgkin's Lymphomas (NHL). It is most commonly diagnosed in older patients, with women more susceptible than men. The disease is classified as a marginal zone lymphoma because the mutation occurs in the marginal zone of the B-cells. Due to its confinement in the lymph nodes, this disease is also classified as nodal.

Splenic Marginal Zone B-Cell Lymphoma

Disclosed herein, in certain embodiments, is a method for treating a splenic marginal zone B-cell lymphoma in an individual in need thereof, comprising: administering to the individual an amount of Compound 1. Further disclosed herein, in certain embodiments, is a method for treating relapsed or refractory splenic marginal zone B-cell lymphoma in an individual in need thereof, comprising: administering to the individual a therapeutically-effective amount of Compound 1.

The term "splenic marginal zone B-cell lymphoma" refers to specific low-grade small B-cell lymphoma that is incorporated in the World Health Organization classification. Characteristic features are splenomegaly, moderate lymphocytosis with villous morphology, intrasinusoidal pattern of involvement of various organs, especially bone marrow, and relative indolent course. Tumor progression with increase of blastic forms and aggressive behavior are observed in a minority of patients. Molecular and cytogenetic studies have shown heterogeneous results probably because of the lack of standardized diagnostic criteria.

Burkitt Lymphoma

Disclosed herein, in certain embodiments, is a method for treating a Burkitt lymphoma in an individual in need thereof, comprising: administering to the individual an amount of Compound 1. Further disclosed herein, in certain embodiments, is a method for treating relapsed or refractory Burkitt lymphoma in an individual in need thereof, comprising: administering to the individual a therapeutically-effective amount of Compound 1.

The term "Burkitt lymphoma" refers to a type of Non-Hodgkin Lymphoma (NHL) that commonly affects children. It is a highly aggressive type of B-cell lymphoma that often starts and involves body parts other than lymph nodes. In spite of its fast-growing nature, Burkitt's lymphoma is often curable with modern intensive therapies. There are two broad types of Burkitt's lymphoma—the sporadic and the endemic varieties:

Endemic Burkitt's lymphoma: The disease involves children much more than adults, and is related to Epstein Barr Virus (EBV) infection in 95% cases. It occurs primarily is equatorial Africa, where about half of all childhood cancers are Burkitt's lymphoma. It characteristically has a high chance of involving the jawbone, a rather distinctive feature that is rare in sporadic Burkitt's. It also commonly involves the abdomen.

Sporadic Burkitt's lymphoma: The type of Burkitt's lymphoma that affects the rest of the world, including Europe and the Americas is the sporadic type. Here too, it's mainly a disease in children. The link between Epstein Barr Virus (EBV) is not as strong as with the endemic variety, though direct evidence of EBV infection is present in one out of five patients. More than the involvement of lymph nodes, it is the abdomen that is notably affected in more than 90% of the children. Bone marrow involvement is more common than in the sporadic variety.

Waldenstrom Macroglobulinemia

Disclosed herein, in certain embodiments, is a method for treating a Waldenstrom macroglobulinemia in an individual in need thereof, comprising: administering to the individual an amount of Compound 1. Further disclosed herein, in certain embodiments, is a method for treating relapsed or refractory Waldenstrom macroglobulinemia in an individual in need thereof, comprising: administering to the individual a therapeutically-effective amount of Compound 1.

The term "Waldenstrom macroglobulinemia", also known as lymphoplasmacytic lymphoma, is cancer involving a subtype of white blood cells called lymphocytes. It is characterized by an uncontrolled clonal proliferation of terminally differentiated B lymphocytes. It is also characterized by the lymphoma cells making an antibody called immunoglobulin M (IgM). The IgM antibodies circulate in the blood in large amounts, and cause the liquid part of the blood to thicken, like syrup. This can lead to decreased blood flow to many organs, which can cause problems with vision (because of poor circulation in blood vessels in the back of the eyes) and neurological problems (such as headache, dizziness, and confusion) caused by poor blood flow within the brain. Other symptoms can include feeling tired and weak, and a tendency to bleed easily. The underlying etiology is not fully understood but a number of risk factors have been identified, including the locus 6p21.3 on chromosome 6. There is a 2- to 3-fold risk increase of developing WM in people with a personal history of autoimmune diseases with autoantibodies and particularly elevated risks associated with hepatitis, human immunodeficiency virus, and rickettsiosis.

Multiple Myeloma

Disclosed herein, in certain embodiments, is a method for treating a myeloma in an individual in need thereof, comprising: administering to the individual an amount of Compound 1. Further disclosed herein, in certain embodiments, is a method for treating relapsed or refractory myeloma in an individual in need thereof, comprising: administering to the individual a therapeutically-effective amount of Compound 1.

Multiple myeloma, also known as MM, myeloma, plasma cell myeloma, or as Kahler's disease (after Otto Kahler) is a cancer of the white blood cells known as plasma cells. A type of B cell, plasma cells are a crucial part of the immune system responsible for the production of antibodies in humans and other vertebrates. They are produced in the bone marrow and are transported through the lymphatic system.

Leukemia

Disclosed herein, in certain embodiments, is a method for treating a leukemia in an individual in need thereof, comprising: administering to the individual an amount of Compound 1. Further disclosed herein, in certain embodiments, is a method for treating relapsed or refractory leukemia in an individual in need thereof, comprising: administering to the individual a therapeutically-effective amount of Compound 1.

Leukemia is a cancer of the blood or bone marrow characterized by an abnormal increase of blood cells, usually leukocytes (white blood cells). Leukemia is a broad term covering a spectrum of diseases. The first division is between its acute and chronic forms: (i) acute leukemia is characterized by the rapid increase of immature blood cells. This crowding makes the bone marrow unable to produce healthy blood cells. Immediate treatment is required in acute leukemia due to the rapid progression and accumulation of the malignant cells, which then spill over into the bloodstream and spread to other organs of the body. Acute forms of leukemia are the most common forms of leukemia in children; (ii) chronic leukemia is distinguished by the excessive build up of relatively mature, but still abnormal, white blood cells. Typically taking months or years to progress, the cells are produced at a much higher rate than normal cells, resulting in many abnormal white blood cells in the blood. Chronic leukemia mostly occurs in older people, but can theoretically occur in any age group. Additionally, the diseases are subdivided according to which kind of blood cell is affected. This split divides leukemias into lymphoblastic or lymphocytic leukemias and myeloid or myelogenous leukemias: (i) lymphoblastic or lymphocytic leukemias, the cancerous change takes place in a type of marrow cell that normally goes on to form lymphocytes, which are infection-fighting immune system cells; (ii) myeloid or myelogenous leukemias, the cancerous change takes place in a type of marrow cell that normally goes on to form red blood cells, some other types of white cells, and platelets.

Within these main categories, there are several subcategories including, but not limited to, Acute lymphoblastic leukemia (ALL), precursor B-cell acute lymphoblastic leukemia (precursor B-ALL; also called precursor B-lymphoblastic leukemia), Acute myelogenous leukemia (AML), Chronic myelogenous leukemia (CML), and Hairy cell leukemia (HCL). Accordingly, disclosed herein, in certain embodiments, is a method for treating Acute lymphoblastic leukemia (ALL), precursor B-cell acute lymphoblastic leukemia (precursor B-ALL; also called precursor B-lymphoblastic leukemia), Acute myelogenous leukemia (AML), Chronic myelogenous leukemia (CML), or Hairy cell leukemia (HCL) in an individual in need thereof, comprising: administering to the individual an amount of Compound 1. In some embodiments, the leukemia is a relapsed or refractory leukemia. In some embodiments, the leukemia is a relapsed or refractory Acute lymphoblastic leukemia (ALL), relapsed or refractory precursor B-cell acute lymphoblastic leukemia (precursor B-ALL; also called precursor B-lymphoblastic leukemia), relapsed or refractory Acute myelogenous leukemia (AML), relapsed or refractory Chronic myelogenous leukemia (CML), or relapsed or refractory Hairy cell leukemia (HCL).

Symptoms, diagnostic tests, and prognostic tests for each of the above-mentioned conditions are known. See, e.g., *Harrison's Principles of Internal Medicine©*," 16th ed., 2004, The McGraw-Hill Companies, Inc. Dey et al. (2006), Cytojournal 3(24), and the "Revised European American Lymphoma" (REAL) classification system (see, e.g., the website maintained by the National Cancer Institute).

A number of animal models of are useful for establishing a range of therapeutically effective doses of irreversible Btk inhibitor compounds, such as Compound 1, for treating any of the foregoing diseases.

The therapeutic efficacy of Compound 1 for any one of the foregoing diseases can be optimized during a course of treatment. For example, a subject being treated can undergo a diagnostic evaluation to correlate the relief of disease symptoms or pathologies to inhibition of in vivo Btk activity achieved by administering a given dose of Compound 1. Cellular assays known in the art can be used to determine in vivo activity of Btk in the presence or absence of an irreversible Btk inhibitor. For example, since activated Btk is phosphorylated at tyrosine 223 (Y223) and tyrosine 551 (Y551), phospho-specific immunocytochemical staining of P-Y223 or P-Y551-positive cells can be used to detect or quantify activation of Bkt in a population of cells (e.g., by FACS analysis of stained vs unstained cells). See, e.g., Nisitani et al. (1999), *Proc. Natl. Acad. Sci, USA* 96:2221-2226. Thus, the amount of the Btk inhibitor inhibitor compound that is administered to a subject can be increased or decreased as needed so as to maintain a level of Btk inhibition optimal for treating the subject's disease state.

Compound 1 can irreversibly inhibit Btk and may be used to treat mammals suffering from Bruton's tyrosine kinase-dependent or Bruton's tyrosine kinase mediated conditions or diseases, including, but not limited to, cancer, autoimmune and other inflammatory diseases. Compound 1 has shown efficacy is a wide variety of diseases and conditions that are described herein.

In some embodiments, Compound 1 is used for the manufacture of a medicament for treating any of the foregoing conditions (e.g., autoimmune diseases, inflammatory diseases, allergy disorders, B-cell proliferative disorders, or thromboembolic disorders).

Compound 1, and Pharmaceutically Acceptable Salts Thereof

The Btk inhibitor compound described herein (i.e. Compound 1) is selective for Btk and kinases having a cysteine residue in an amino acid sequence position of the tyrosine kinase that is homologous to the amino acid sequence position of cysteine 481 in Btk. The Btk inhibitor compound can form a covalent bond with Cys 481 of Btk (e.g., via a Michael reaction).

"Compound 1" or "1-((R)-3-(4-amino-3-(4-phenoxyphenyl)-1H-pyrazolo[3,4-d]pyrimidin-1-yl)piperidin-1-yl)prop-2-en-1-one" or "1-{(3R)-3-[4-amino-3-(4-phenoxyphenyl)-1H-pyrazolo[3,4-d]pyrimidin-1-yl]piperidin-1-yl}prop-2-en-1-one" or "2-Propen-1-one, 1-[(3R)-3-[4-amino-3-(4-phenoxyphenyl)-1H-pyrazolo[3,4-d]pyrimidin-1-yl]-1-piperidinyl-" or ibrutinib or any other suitable name refers to the compound with the following structure:

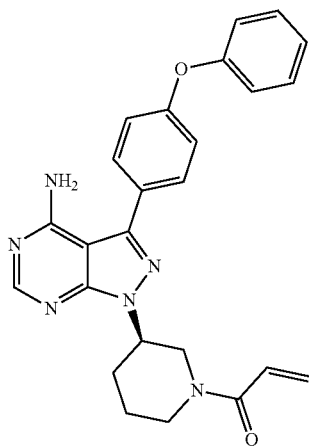 [SMILES: C=CC(=O)N1CCC[C@@H](n2nc(-c3ccc(Oc4ccccc4)cc3)c3c(N)ncnc32)C1]

A wide variety of pharmaceutically acceptable salts is formed from Compound 1 and includes:
  acid addition salts formed by reacting Compound 1 with an organic acid, which includes aliphatic mono- and dicarboxylic acids, phenyl-substituted alkanoic acids, hydroxyl alkanoic acids, alkanedioic acids, aromatic acids, aliphatic and aromatic sulfonic acids, amino acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonica acid, p-toluenesulfonic acid, salicylic acid, and the like;
  acid addition salts formed by reacting Compound 1 with an inorganic acid, which includes hydrochloric acid, hydrobromic acid, sulfuric acid, nitric acid, phosphoric acid, hydroiodic acid, hydrofluoric acid, phosphorous acid, and the like.

The term "pharmaceutically acceptable salts" in reference to Compound 1 refers to a salt of Compound 1, which does not cause significant irritation to a mammal to which it is administered and does not substantially abrogate the biological activity and properties of the compound.

It should be understood that a reference to a pharmaceutically acceptable salt includes the solvent addition forms (solvates). Solvates contain either stoichiometric or non-stoichiometric amounts of a solvent, and are formed during the process of product formation or isolation with pharmaceutically acceptable solvents such as water, ethanol, methanol, methyl tert-butyl ether (MTBE), diisopropyl ether (DIPE), ethyl acetate, isopropyl acetate, isopropyl alcohol, methyl isobutyl ketone (MIBK), methyl ethyl ketone (MEK), acetone, nitromethane, tetrahydrofuran (THF), dichloromethane (DCM), dioxane, heptanes, toluene, anisole, acetonitrile, and the like. In one aspect, solvates are formed using, but not limited to, Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C (R3), (November 2005). Hydrates are formed when the solvent is water, or alcoholates are formed when the solvent is alcohol. In some embodiments, solvates of Compound 1, or pharmaceutically acceptable salts thereof, are conveniently prepared or formed during the processes described herein. In some embodiments, solvates of Compound 1 are anhydrous. In some embodiments, Compound 1, or pharmaceutically acceptable salts thereof, exist in unsolvated form. In some embodiments, Compound 1, or pharmaceutically acceptable salts thereof, exist in unsolvated form and are anhydrous.

In yet other embodiments, Compound 1, or a pharmaceutically acceptable salt thereof, is prepared in various forms, including but not limited to, amorphous phase, crystalline forms, milled forms and nano-particulate forms. In some embodiments, Compound 1, or a pharmaceutically acceptable salt thereof, is amorphous. In some embodiments, Compound 1, or a pharmaceutically acceptable salt thereof, is amorphous and anhydrous. In some embodiments, Compound 1, or a pharmaceutically acceptable salt thereof, is crystalline. In some embodiments, Compound 1, or a pharmaceutically acceptable salt thereof, is crystalline and anhydrous.

In some embodiments, Compound 1 is prepared as outlined in U.S. Pat. No. 7,514,444.

Amorphous Compound 1

In some embodiments, Compound 1 is amorphous and anhydrous. In some embodiments, Compound 1 is amorphous. In some embodiments, amorphous Compound 1 has an X-Ray Powder Diffraction (XRPD) pattern showing a lack of crystallinity.

Compound 1, Form A

In some embodiments, Compound 1 is crystalline. In some embodiments, Compound 1 is crystalline Form A. Crystalline Form A of Compound 1 is characterized as having at least one of the following properties:
  (a) an X-Ray powder diffraction (XRPD) pattern substantially the same as shown in FIG. 1;
  (b) an X-ray powder diffraction (XRPD) pattern with characteristic peaks at 5.7±0.1° 2-Theta, 13.6±0.10 2-Theta, 16.1±0.10 2-Theta, 18.9±0.10 2-Theta, 21.3±0.10 2-Theta, and 21.6±0.1° 2-Theta;
  (c) substantially the same X-ray powder diffraction (XRPD) pattern post storage at 40° C. and 75% RH for at least a week;
  (d) substantially the same X-ray powder diffraction (XRPD) pattern post storage at 25° C. and 97% RH for at least a week;
  (e) Infrared (IR) spectrum substantially similar to the one set forth in FIG. 2;
  (f) Infrared (IR) spectrum weak peaks at about 1584 cm$^{-1}$, about 1240 cm$^{-1}$, about 1147 cm$^{-1}$, about 1134 cm$^{-1}$, about 1099 cm$^{-1}$, and about 1067 cm$^{-1}$;
  (g) a DSC thermogram substantially similar to the one set forth in FIG. 3;
  (h) a thermo-gravimetric analysis (TGA) thermogram substantially similar to the one set forth in FIG. 4;
  (i) a DSC thermogram with an endotherm having an onset at about 154° C. and a peak at about 157° C. and an exotherm at about 159° C.;
  (j) non-hygroscopicity;
  (k) an observed aqueous solubility of about 0.013 mg/mL at about pH 8;
  or
  (l) combinations thereof.

In some embodiments, Form A of Compound 1 is characterized as having at least two of the properties selected from (a) to (k). In some embodiments, Form A of Compound 1 is characterized as having at least three of the properties selected from (a) to (k). In some embodiments, Form A of Compound 1 is characterized as having at least four of the properties selected from (a) to (k). In some embodiments, Form A of Compound 1 is characterized as having at least five of the properties selected from (a) to (k). In some embodiments, Form A of Compound 1 is characterized as having at least six of the properties selected from (a) to (k). In some embodiments, Form A of Compound 1 is characterized as having at least seven of the properties selected from (a) to (k). In some embodiments, Form A of Compound 1 is characterized as having at least eight of the properties selected from (a) to (k). In some embodiments, Form A of Compound 1 is characterized as having at least nine of the properties selected from (a) to (k). In some embodiments, Form A of Compound 1 is characterized as having at least ten of the properties selected from (a) to (k). In some embodiments, Form A of Compound 1 is characterized as having properties (a) to (k).

In some embodiments, Form A has an X-Ray powder diffraction (XRPD) pattern substantially the same as shown in FIG. 1. In some embodiments, Form A has an X-ray powder diffraction (XRPD) pattern with characteristic peaks at 5.7±0.10 2-Theta, 13.6±0.1° 2-Theta, 16.1±0.10 2-Theta, 18.9±0.10 2-Theta, 21.3±0.10 2-Theta, and 21.6±0.10 2-Theta. In some embodiments, Form A has substantially the same X-ray powder diffraction (XRPD) pattern post storage at 40° C. and 75% RH for at least a week. In some embodiments, Form A has substantially the same X-ray powder diffraction (XRPD) pattern post storage at 25° C. and 97% RH for at least a week.

Figure 2:
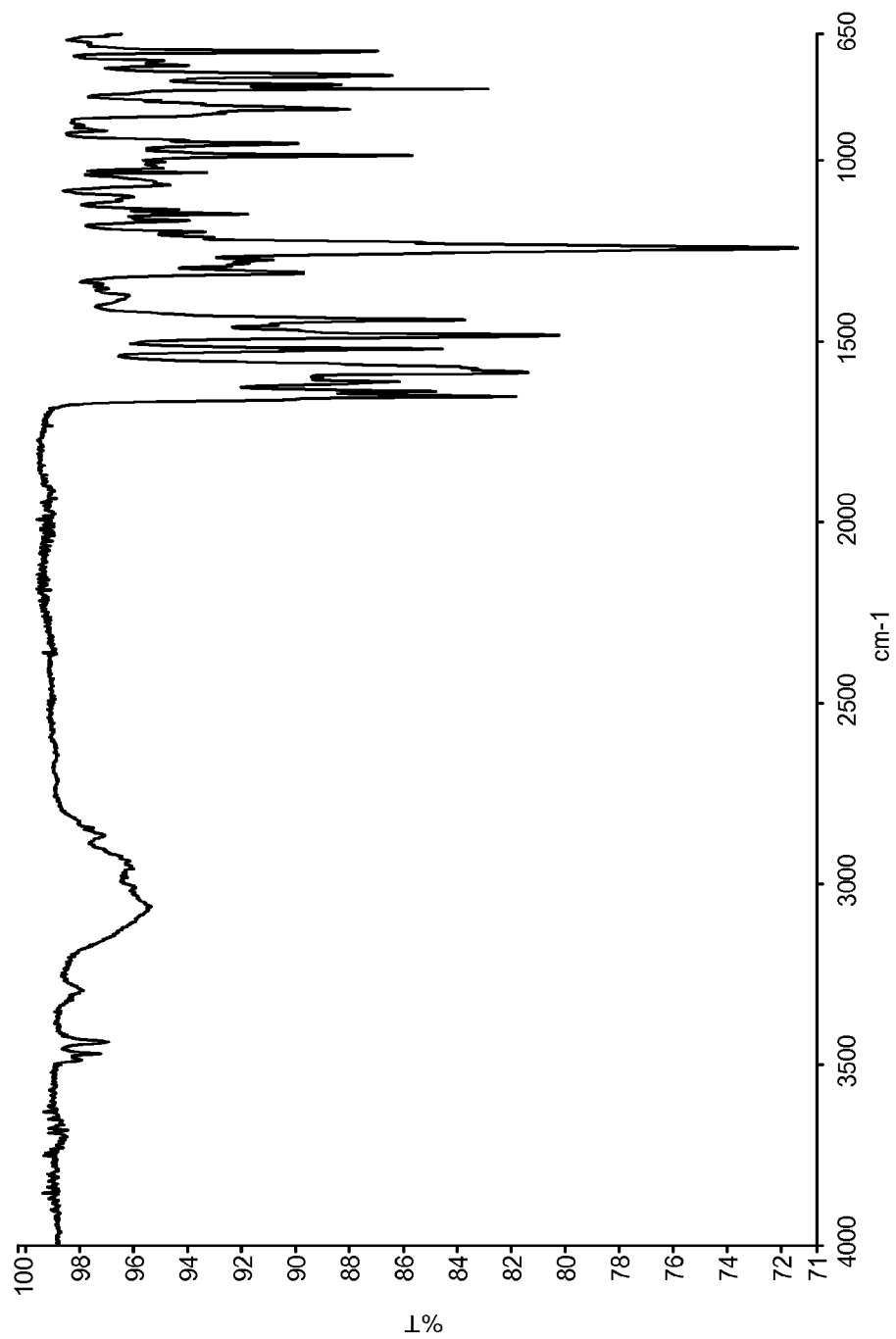
FIG. 2. Illustrates an an Infrared (IR) spectrum of Form A.

In some embodiments, Form A has an Infrared (IR) spectrum substantially similar to the one set forth in FIG. 2. In some embodiments, Form A has an Infrared (IR) spectrum weak peaks at about 1584 $cm^{-1}$, about 1240 $cm^{-1}$, about 1147 $cm^{-1}$, about 1134 $cm^{-1}$, about 1099 $cm^{-1}$, and about 1067 $cm^{-1}$.

Figure 3:
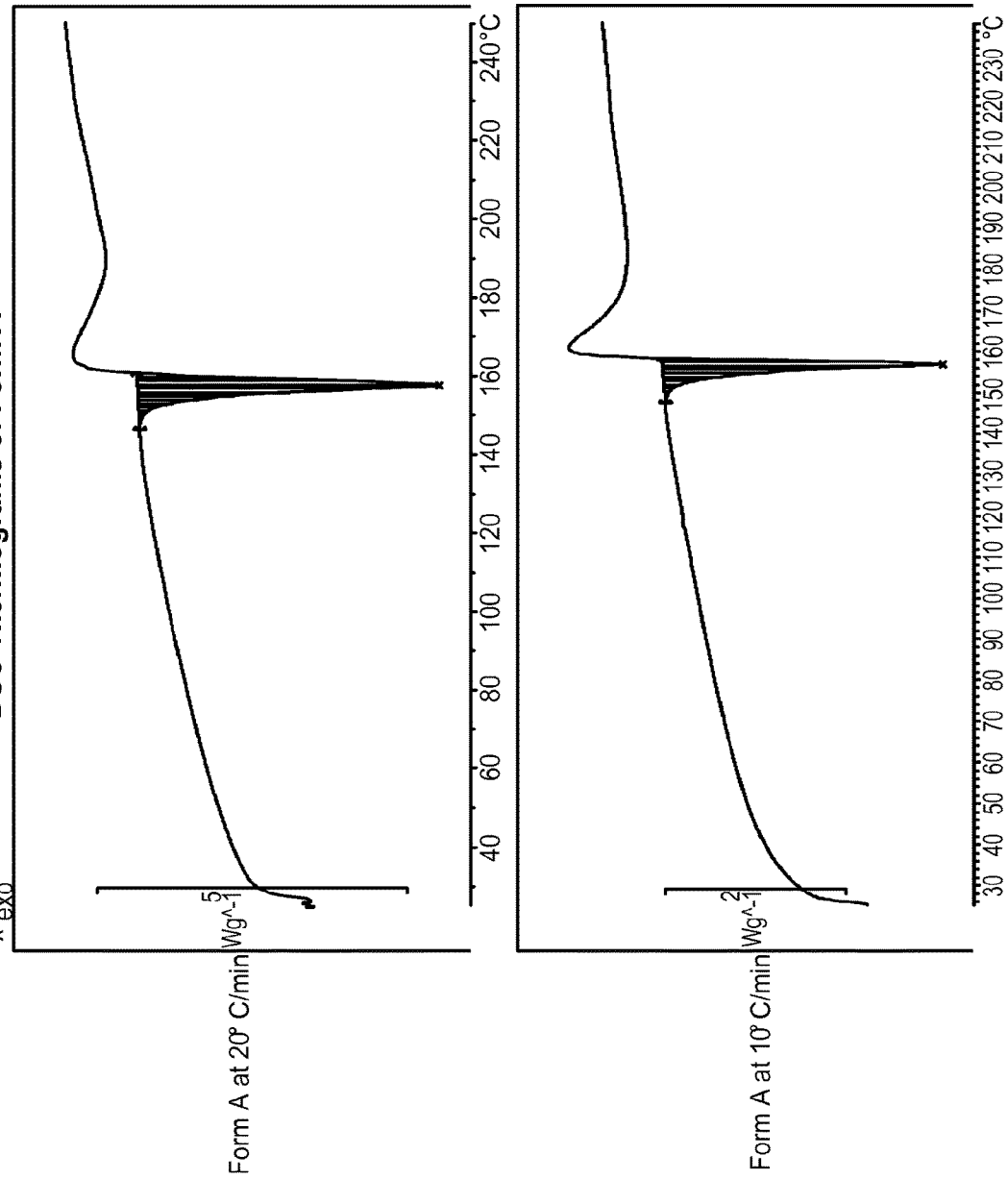
FIG. 3. Illustrates DSC thermograms of Form A.

In some embodiments, Form A has a DSC thermogram substantially similar to the one set forth in FIG. 3. In some embodiments, Form A has a thermo-gravimetric analysis (TGA) thermogram substantially similar to the one set forth in FIG. 4. In some embodiments, Form A has a DSC thermogram with an endotherm having an onset at about 154° C. and a peak at about 157° C. and an exotherm at about 159° C.

In some embodiments, Form A has non-hygroscopicity.

In some embodiments, Form A has an observed aqueous solubility of about 0.013 mg/mL at about pH 8.

In some embodiments, Form A was obtained from ethyl acetate, isopropyl acetate, tetrahydrofuran, methyl isobutyl ketone (MIBK), methyl ethyl ketone (MEK), nitromethane, methanol, ethanol, acetonitrile, dioxane, methyl tert-butyl ether (MTBE), anisole, acetone, heptanes, a methanol/water mixture or an acetone/heptane mixture. In some embodiments, Form A was obtained from ethyl acetate, isopropyl acetate, tetrahydrofuran, methyl isobutyl ketone (MIBK), methyl ethyl ketone (MEK), nitromethane, methanol, ethanol, acetonitrile, dioxane, methyl tert-butyl ether (MTBE), anisole, acetone, heptanes, or an acetone/heptane mixture.

In some embodiments, Form A is unsolvated. In some embodiments, Form A is anhydrous.

Compound 1, Form B

Figure 5:
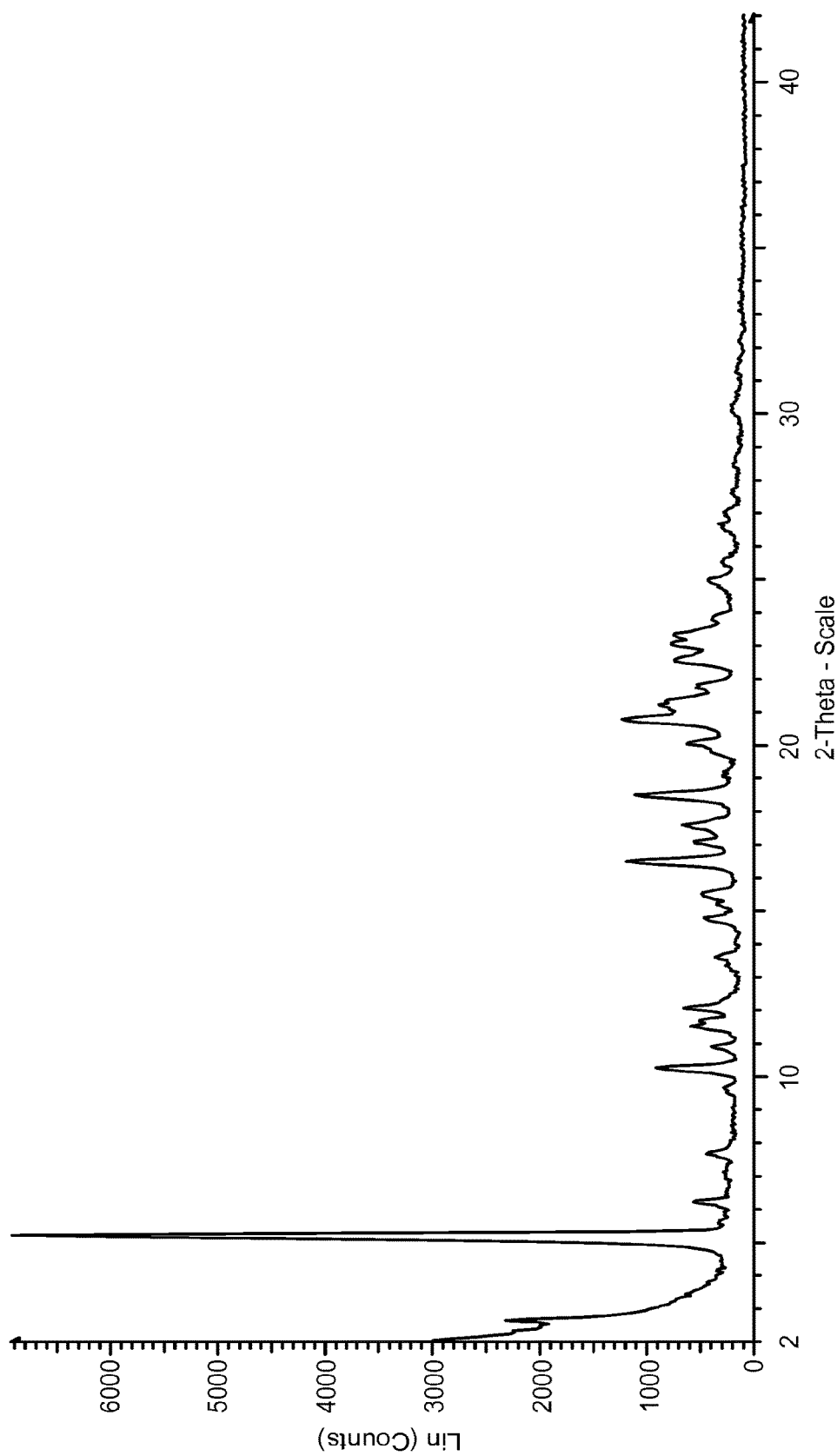
FIG. 5. Illustrates an X-Ray powder diffraction (XRPD) pattern of Form B.
Figure 6:
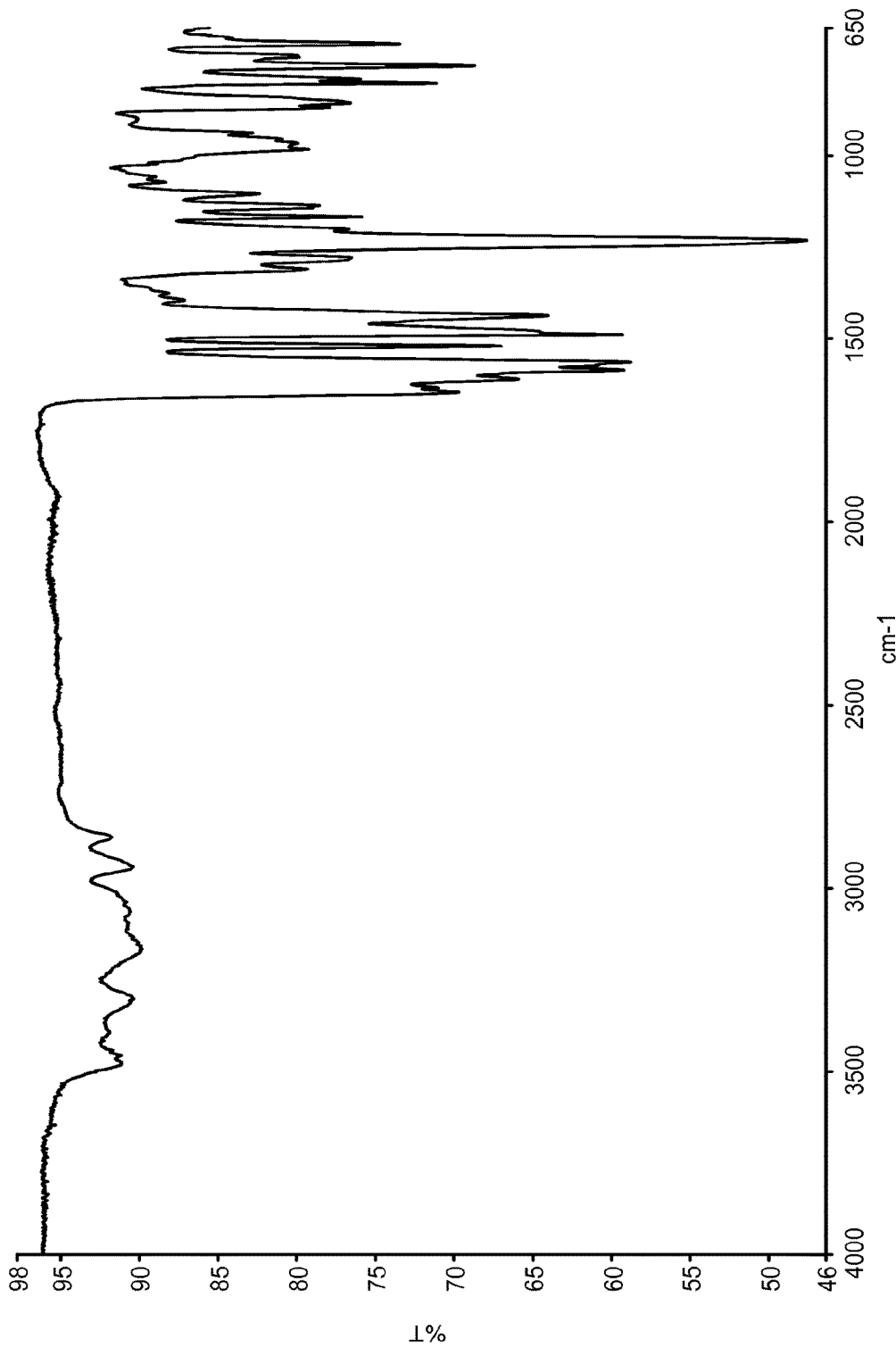
FIG. 6. Illustrates an an Infrared (IR) spectrum of Form B.
Figure 7:
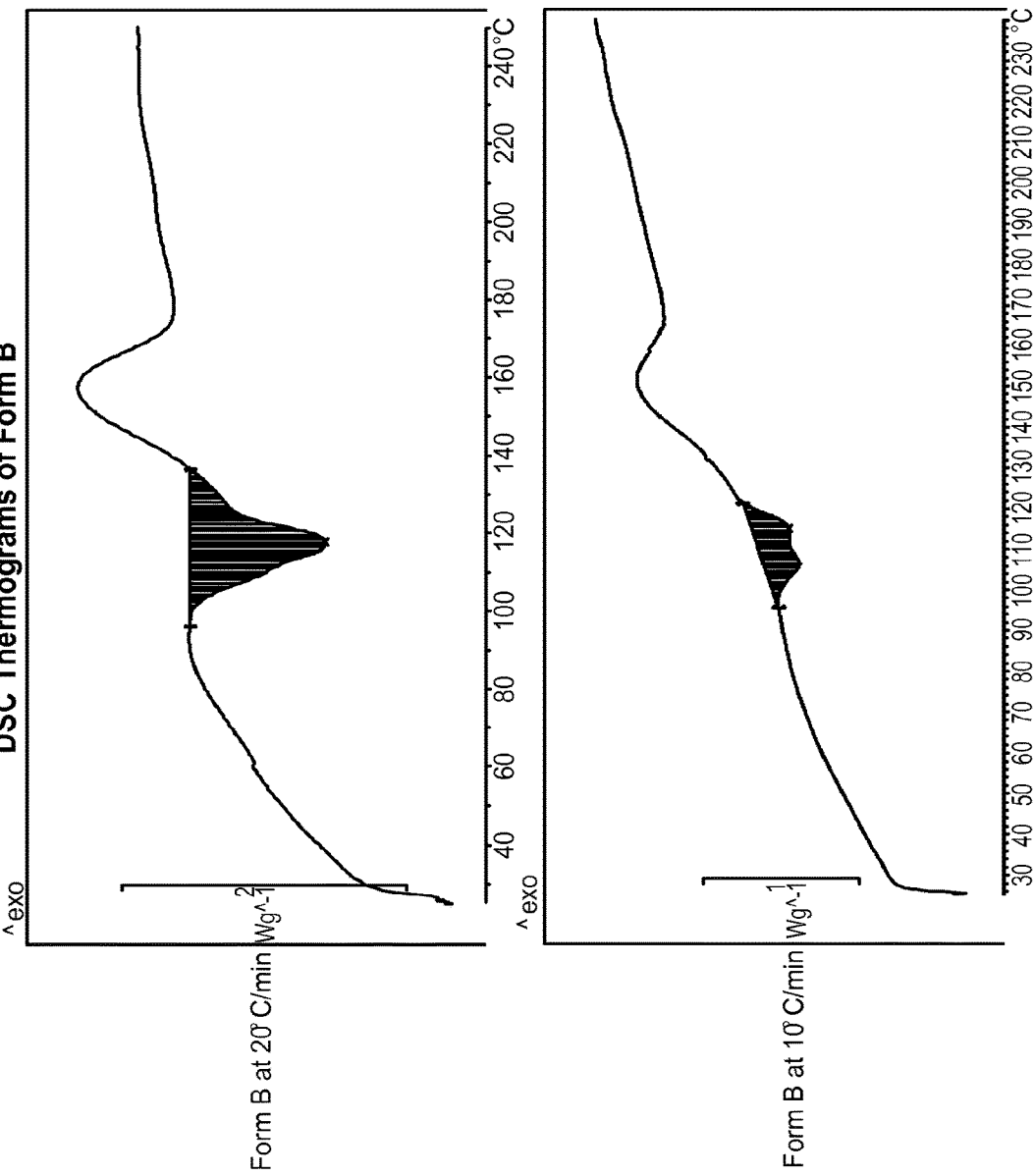
FIG. 7. Illustrates DSC thermograms of Form B.
Figure 8:
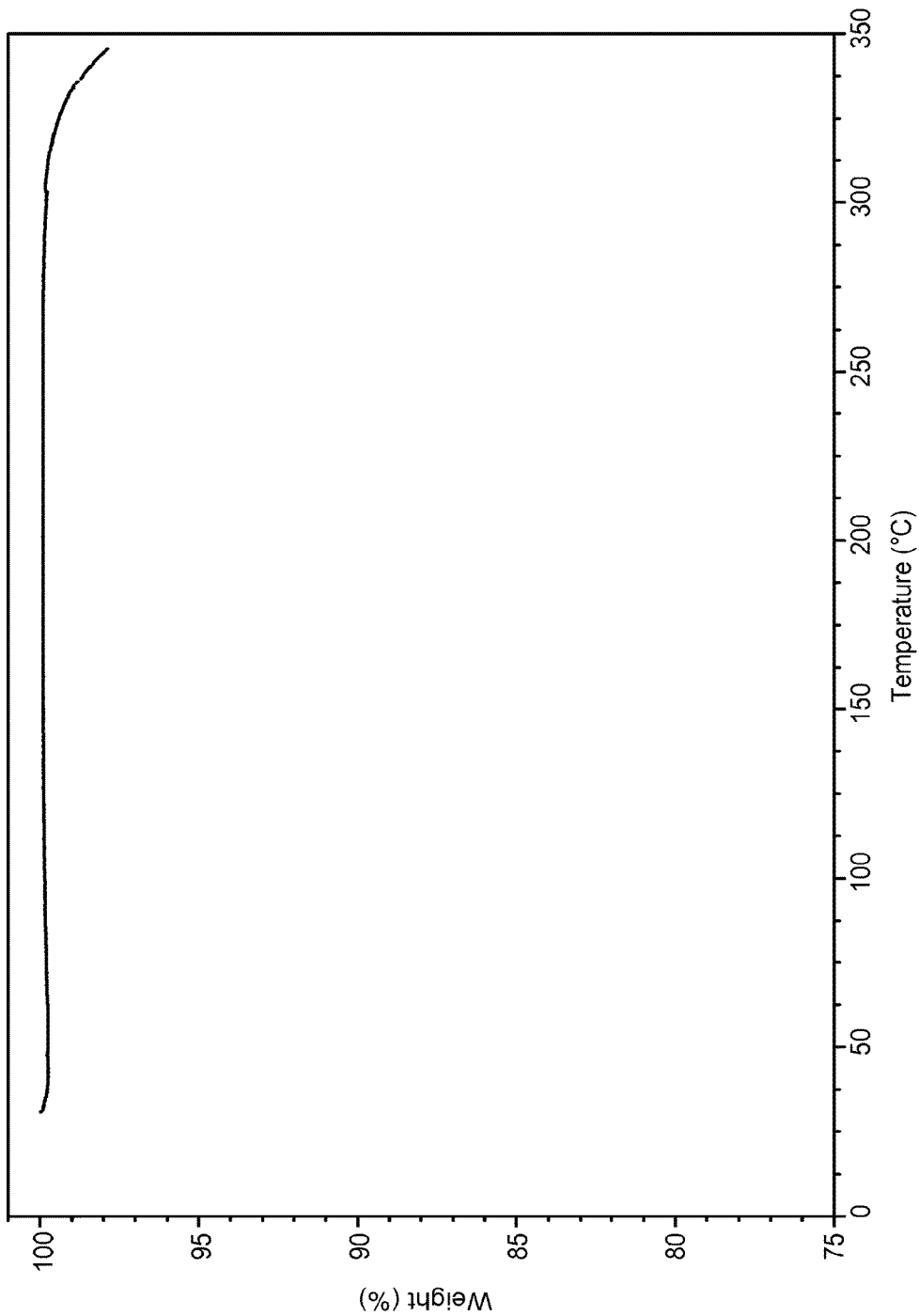
FIG. 8. Illustrates a thermo-gravimetric analysis (TGA) thermogram of Form B.

In some embodiments, Compound 1 is crystalline. In some embodiments, Compound 1 is crystalline Form B. Crystalline Form B of Compound 1 is characterized as having at least one of the following properties:

(a) an X-Ray powder diffraction (XRPD) pattern substantially the same as shown in FIG. 5;

(b) an X-ray powder diffraction (XRPD) pattern with characteristic peaks at 5.2±0.1° 2-Theta, 10.2±0.10 2-Theta, 16.5±0.10 2-Theta, 18.5±0.10 2-Theta, and 20.8±0.10 2-Theta;

(c) substantially the same X-ray powder diffraction (XRPD) pattern post storage at 40° C. and 75% RH for at least a week;

(d) substantially the same X-ray powder diffraction (XRPD) pattern post storage at 25° C. and 97% RH for at least a week;

(e) Infrared (IR) spectrum substantially similar to the one set forth in FIG. 6;

(f) Infrared (IR) spectrum weak peaks at about about 1586 $cm^{-1}$, about 1573 $cm^{-1}$, about 1562 $cm^{-1}$, about 1229 $cm^{-1}$, about 1141 $cm^{-1}$, about 1103 $cm^{-1}$, about 1056 $cm^{-1}$, and about 1033 $cm^{-1}$;

(g) a DSC thermogram substantially similar to the one set forth in FIG. 7;

(h) a thermo-gravimetric analysis (TGA) thermogram substantially similar to the one set forth in FIG. 8;

(i) a DSC thermogram with an endotherm having an onset at about 99-106° C. and a peak at about 115-118° C.;

(j) an observed aqueous solubility of about 0.0096 mg/mL at a pH of about 7.42;

or (k) combinations thereof.

In some embodiments, Form B of Compound 1 is characterized as having at least two of the properties selected from (a) to (j). In some embodiments, Form B of Compound 1 is characterized as having at least three of the properties selected from (a) to (j). In some embodiments, Form B of Compound 1 is characterized as having at least four of the properties selected from (a) to (j). In some embodiments, Form B of Compound 1 is characterized as having at least five of the properties selected from (a) to (j). In some embodiments, Form B of Compound 1 is characterized as having at least six of the properties selected from (a) to (j). In some embodiments, Form B of Compound 1 is characterized as having at least seven of the properties selected from (a) to (j). In some embodiments, Form B of Compound 1 is characterized as having at least eight of the properties selected from (a) to (j). In some embodiments, Form B of Compound 1 is characterized as having at least nine of the properties selected from (a) to (j). In some embodiments, Form B of Compound 1 is characterized as having properties (a) to (j).

In some embodiments, Form B has an X-Ray powder diffraction (XRPD) pattern substantially the same as shown in FIG. 5. In some embodiments, Form B has an X-ray powder diffraction (XRPD) pattern with characteristic peaks at 5.2±0.1° 2-Theta, 10.2±0.1° 2-Theta, 16.5±0.10 2-Theta, 18.5±0.10 2-Theta, and 20.8±0.10 2-Theta. In some embodiments, Form B has substantially the same X-ray powder diffraction (XRPD) pattern post storage at 40° C. and 75% RH for at least a week. In some embodiments, Form B has substantially the same X-ray powder diffraction (XRPD) pattern post storage at 25° C. and 97% RH for at least a week.

In some embodiments, Form B has an Infrared (IR) spectrum substantially similar to the one set forth in FIG. 6. In some embodiments, Form B has an Infrared (IR) spectrum weak peaks at about about 1586 $cm^{-1}$, about 1573 cm⁻¹, about 1562 cm⁻¹, about 1229 cm⁻¹, about 1141 cm⁻¹, about 1103 cm⁻¹, about 1056 cm⁻¹, and about 1033 cm⁻¹.

In some embodiments, Form B has a DSC thermogram substantially similar to the one set forth in FIG. 7. In some embodiments, Form B has a thermo-gravimetric analysis (TGA) thermogram substantially similar to the one set forth in FIG. 8. In some embodiments, Form B has a DSC thermogram with an endotherm having an onset at about 99-106° C. and a peak at about 115-118° C.

In some embodiments, Form B has an observed aqueous solubility of about 0.0096 mg/mL at a pH of about 7.42.

In some embodiments, Form B was obtained from a mixture of methanol and water.

In some embodiments, Form B is unsolvated. In some embodiments, Form B is anhydrous.

Compound 1, Form C

Figure 9:
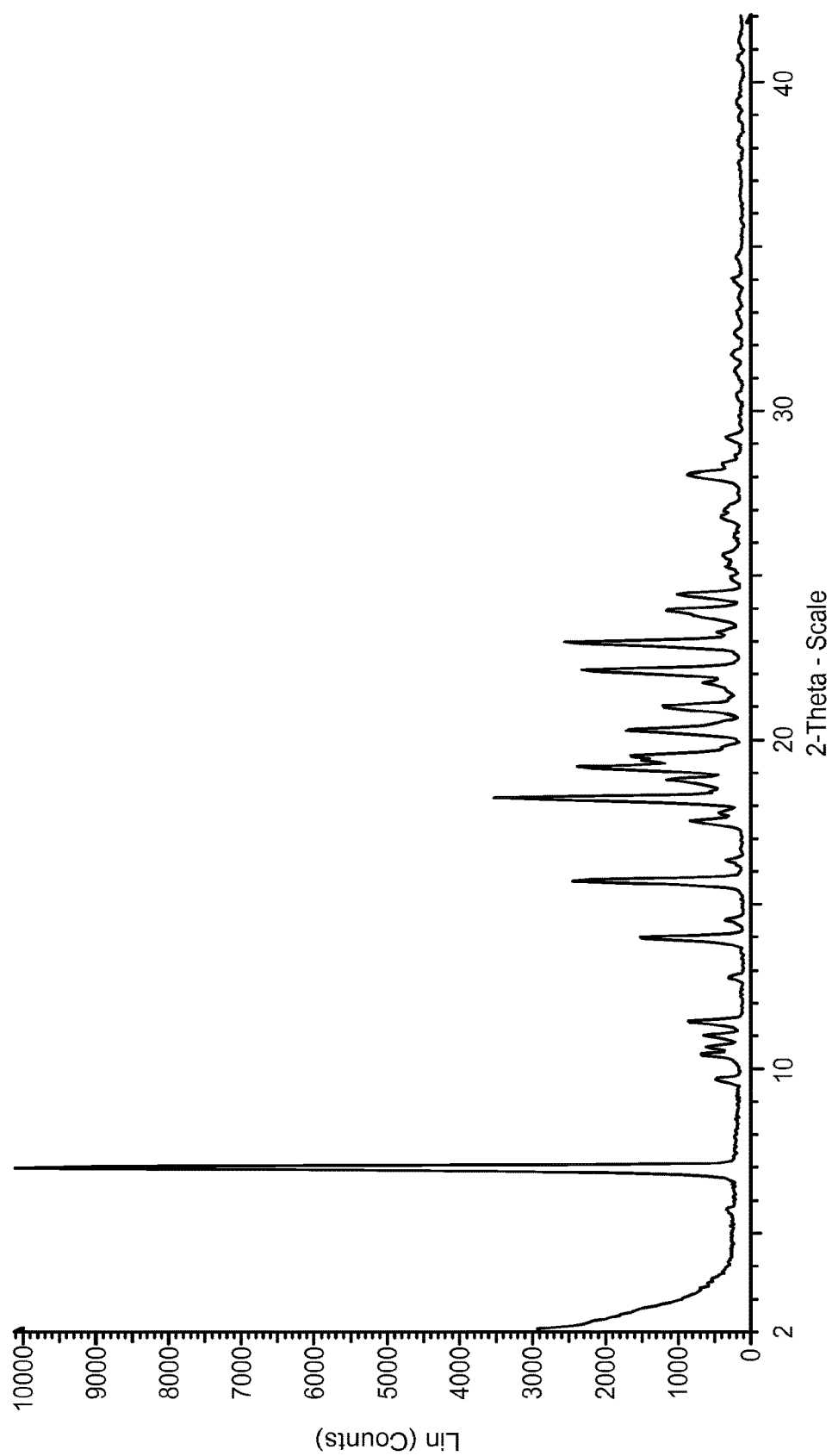
FIG. 9. Illustrates an X-Ray powder diffraction (XRPD) pattern of Form C.

In some embodiments, Compound 1 is crystalline. In some embodiments, Compound 1 is crystalline Form C. Crystalline Form C of Compound 1 is characterized as having at least one of the following properties:
  (a) an X-Ray powder diffraction (XRPD) pattern substantially the same as shown in FIG. 9;
  (b) an X-ray powder diffraction (XRPD) pattern with characteristic peaks at 7.0±0.1° 2-Theta, 14.0±0.10 2-Theta, 15.7±0.10 2-Theta, 18.2±0.10 2-Theta, 19.1±0.10 2-Theta, 19.5±0.1° 2-Theta, 20.3±0.1° 2-Theta, 22.1±0.1° 2-Theta, and 22.9±0.10 2-Theta;
  (c) a DSC thermogram substantially similar to the one set forth in FIG. 10;
  (d) a thermo-gravimetric analysis (TGA) thermogram substantially similar to the one set forth in FIG. 11;
  (e) a DSC thermogram with an endotherm having an onset at about 134-135° C. and a peak at about 137-139° C.;
or
  (f) combinations thereof.

In some embodiments, Form C of Compound 1 is characterized as having at least two of the properties selected from (a) to (e). In some embodiments, Form C of Compound 1 is characterized as having at least three of the properties selected from (a) to (e). In some embodiments, Form C of Compound 1 is characterized as having at least four of the properties selected from (a) to (e). In some embodiments, Form C of Compound 1 is characterized as having properties (a) to (e).

In some embodiments, Form C has an X-Ray powder diffraction (XRPD) pattern substantially the same as shown in FIG. 9. In some embodiments, Form C has an X-ray powder diffraction (XRPD) pattern with characteristic peaks at 7.0±0.1° 2-Theta, 14.0±0.1° 2-Theta, 15.7±0.10 2-Theta, 18.2±0.10 2-Theta, 19.1±0.1° 2-Theta, 19.5±0.1° 2-Theta, 20.3±0.10 2-Theta, 22.1±0.10 2-Theta, and 22.9±0.10 2-Theta.

Figure 10:
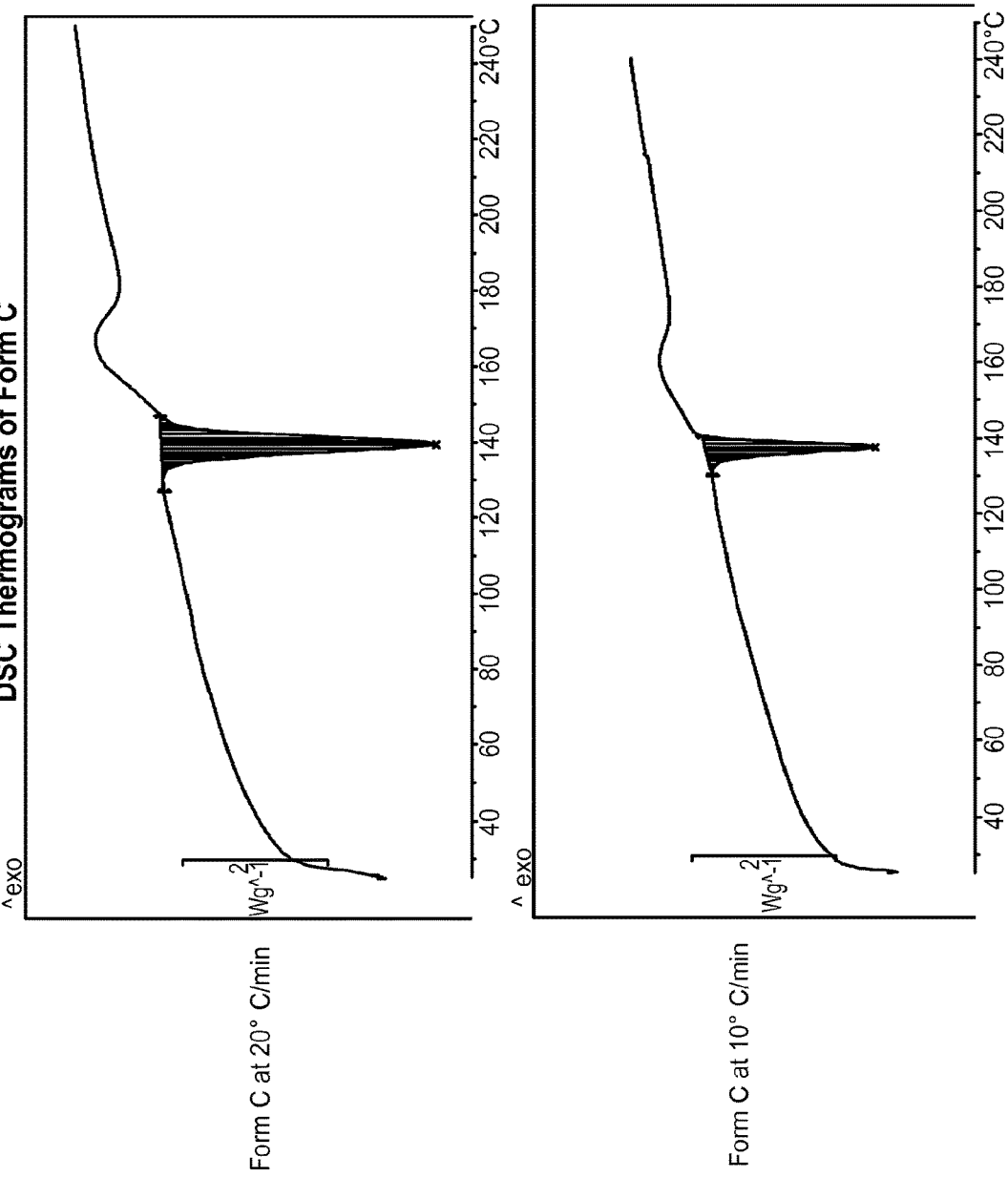
FIG. 10. Illustrates DSC thermograms of Form C.

In some embodiments, Form C has a DSC thermogram substantially similar to the one set forth in FIG. 10. In some embodiments, Form C has a thermo-gravimetric analysis (TGA) thermogram substantially similar to the one set forth in FIG. 11. In some embodiments, Form C has a DSC thermogram with an endotherm having an onset at about 134-135° C. and a peak at about 137-139° C.

In some embodiments, Form C was obtained from a mixture of methanol and water. In some embodiments, Form C was obtained from methanol.

In some embodiments, Form C is unsolvated. In some embodiments, Form C is anhydrous.

Compound 1, Form D

Figure 12:
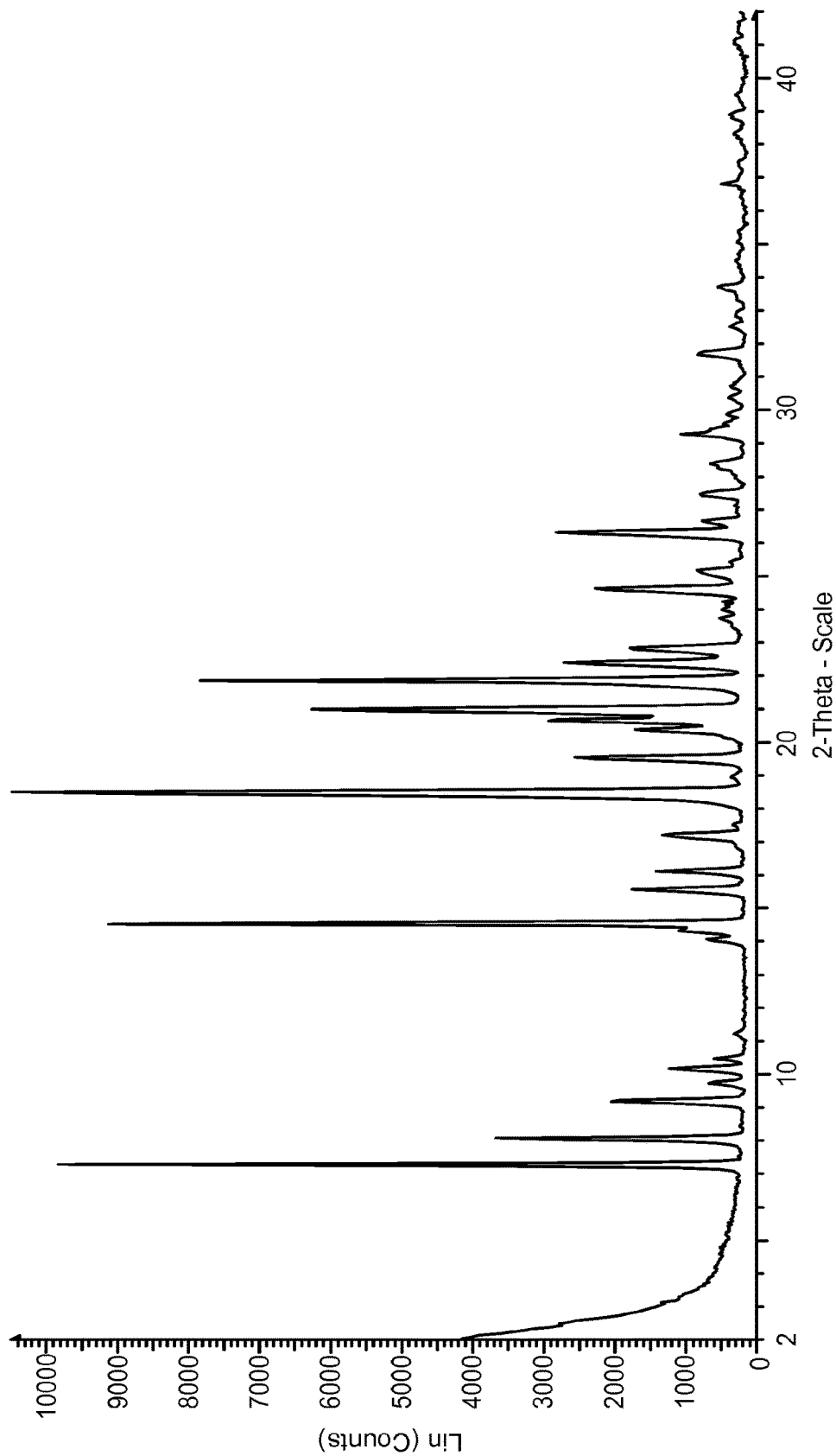
FIG. 12. Illustrates an X-Ray powder diffraction (XRPD) pattern of Form D.

In some embodiments, Compound 1 is crystalline. In some embodiments, Compound 1 is crystalline Form D. Crystalline Form D of Compound 1 is characterized as having at least one of the following properties:
  (a) an X-Ray powder diffraction (XRPD) pattern substantially the same as shown in FIG. 12;
  (b) an X-ray powder diffraction (XRPD) pattern with characteristic peaks at 7.2±0.1° 2-Theta, 8.0±0.10 2-Theta, 9.2±0.10 2-Theta, 14.5±0.10 2-Theta, 18.5±0.10 2-Theta, 19.5±0.10 2-Theta, 20.7±0.10 2-Theta, 21.0±0.10 2-Theta, 21.9±0.10 2-Theta, and 22.4±0.1° 2-Theta;
  (c) a thermo-gravimetric analysis (TGA) thermogram substantially similar to the one set forth in FIG. 13;
or
  (d) combinations thereof.

In some embodiments, Form D of Compound 1 is characterized as having at least two of the properties selected from (a) to (c). In some embodiments, Form D of Compound 1 is characterized as having properties (a), (b), and (c).

In some embodiments, Form D has an X-Ray powder diffraction (XRPD) pattern substantially the same as shown in FIG. 12. In some embodiments, Form D has an X-ray powder diffraction (XRPD) pattern with characteristic peaks at 7.2±0.1° 2-Theta, 8.0±0.1° 2-Theta, 9.2±0.1° 2-Theta, 14.5±0.10 2-Theta, 18.5±0.10 2-Theta, 19.5±0.10 2-Theta, 20.7±0.10 2-Theta, 21.0±0.10 2-Theta, 21.9±0.10 2-Theta, and 22.4±0.10 2-Theta.

Figure 13:
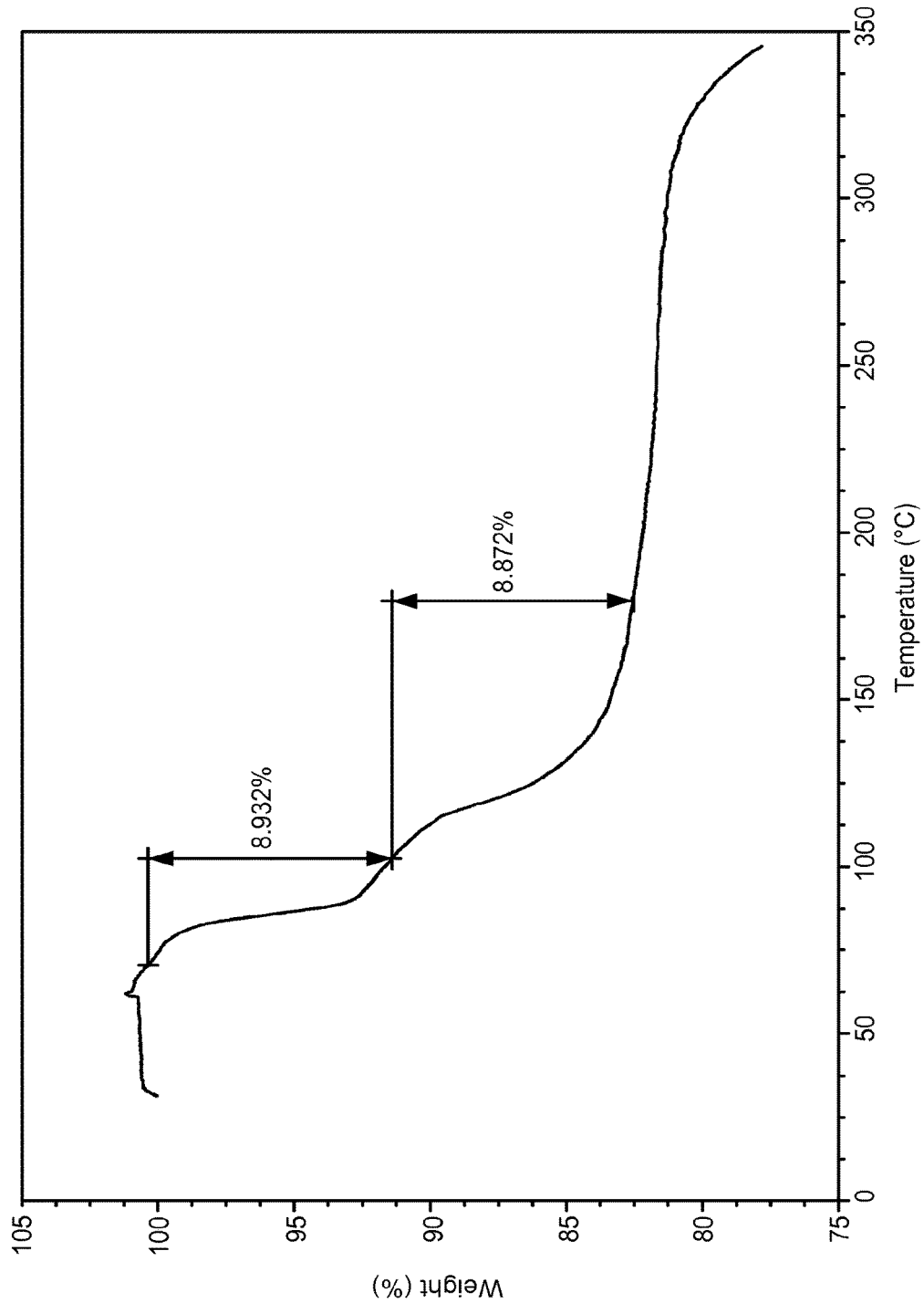
FIG. 13. Illustrates a thermo-gravimetric analysis (TGA) thermogram of Form D.

In some embodiments, Form D has a thermo-gravimetric analysis (TGA) thermogram substantially similar to the one set forth in FIG. 13.

In some embodiments, Form D was obtained from methyl isobutyl ketone (MIBK). In some embodiments, Form D is solvated. In some embodiments, Form D is solvated with methyl isobutyl ketone (MIBK).

Compound 1, Form E

Figure 14:
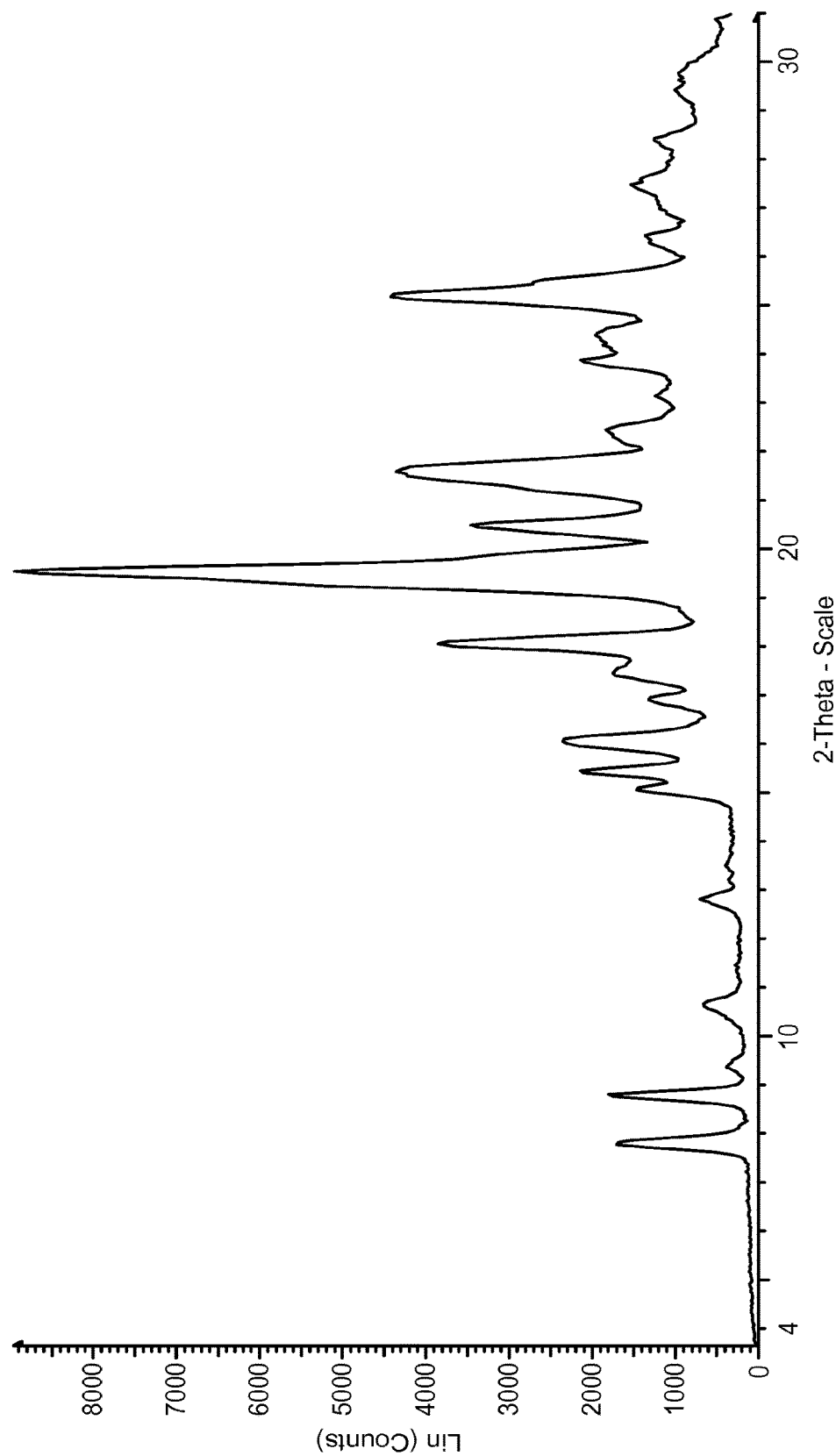
FIG. 14. Illustrates an X-Ray powder diffraction (XRPD) pattern of Form E.

In some embodiments, Compound 1 is crystalline. In some embodiments, Compound 1 is crystalline Form E. Crystalline Form E of Compound 1 is characterized as having at least one of the following properties:
  (a) an X-Ray powder diffraction (XRPD) pattern substantially the same as shown in FIG. 14;
  (b) an X-ray powder diffraction (XRPD) pattern with characteristic peaks at 7.8±0.1° 2-Theta, 8.8±0.1° 2-Theta, 16.1±0.1° 2-Theta, 18.1±0.1° 2-Theta, 19.3±0.1° 2-Theta, 19.5±0.10 2-Theta, 20.5±0.10 2-Theta, 21.6±0.10 2-Theta, and 25.2±0.10 2-Theta;
  (c) a DSC thermogram substantially similar to the one set forth in FIG. 15;
  (d) a thermo-gravimetric analysis (TGA) thermogram substantially similar to the one set forth in FIG. 15;
or
  (e) combinations thereof.

In some embodiments, Form E of Compound 1 is characterized as having at least two of the properties selected from (a) to (d). In some embodiments, Form E of Compound 1 is characterized as having at least three of the properties selected from (a) to (d). In some embodiments, Form E of Compound 1 is characterized as having properties (a) to (d).

In some embodiments, Form E has an X-Ray powder diffraction (XRPD) pattern substantially the same as shown in FIG. 14. In some embodiments, Form E has an X-ray powder diffraction (XRPD) pattern with characteristic peaks at 7.8±0.10 2-Theta, 8.8±0.10 2-Theta, 16.1±0.10 2-Theta, 18.1±0.10 2-Theta, 19.3±0.10 2-Theta, 19.5±0.10 2-Theta, 20.5±0.10 2-Theta, 21.6±0.10 2-Theta, and 25.2±0.10 2-Theta.

Figure 15:
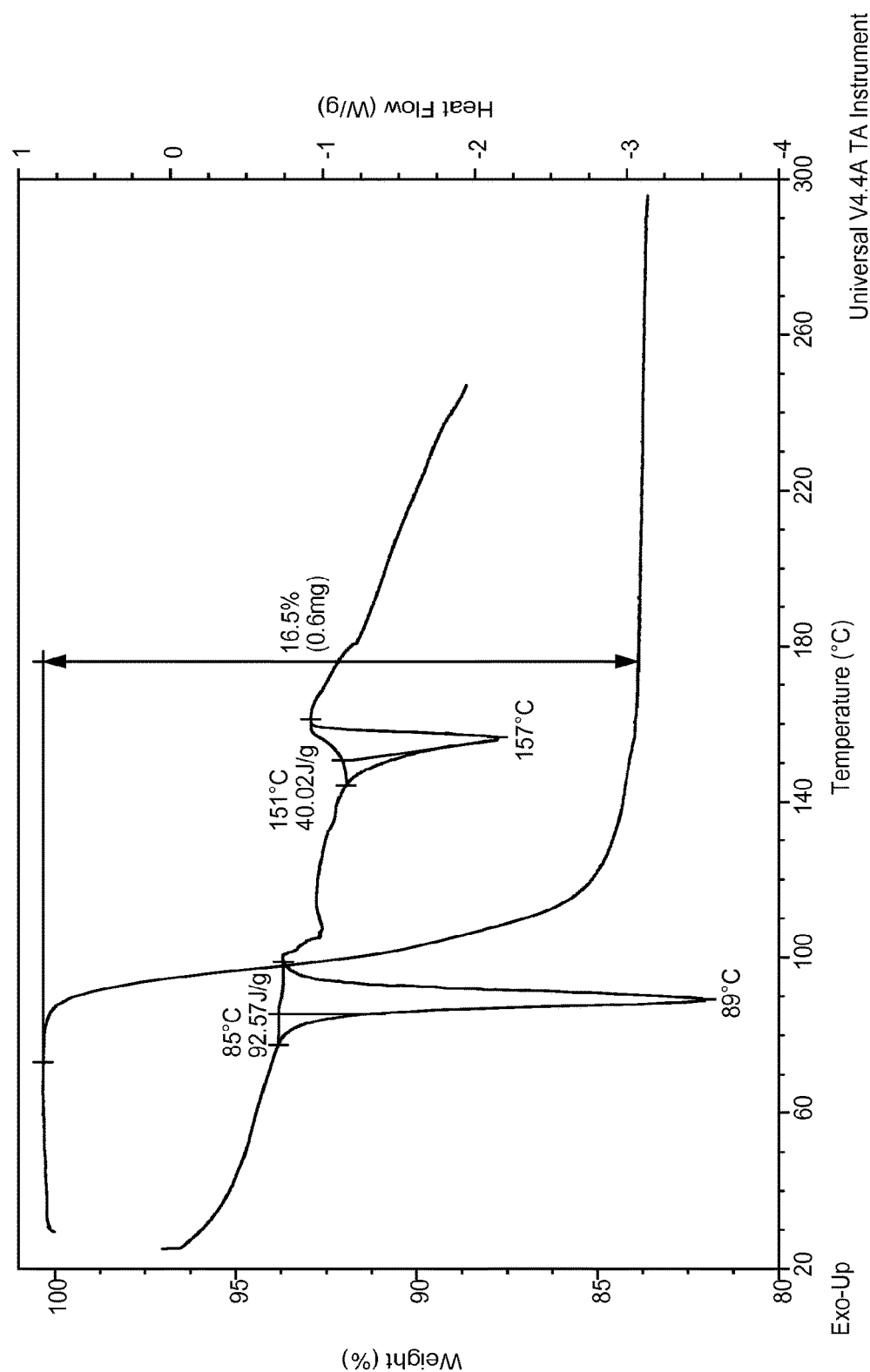
FIG. 15. Illustrates a DSC thermogram and a thermo-gravimetric analysis (TGA) thermogram of Form E.

In some embodiments, Form E has a DSC thermogram substantially similar to the one set forth in FIG. 15. In some embodiments, Form E has a thermo-gravimetric analysis (TGA) thermogram substantially similar to the one set forth in FIG. 15.

In some embodiments, Form E was obtained from toluene.

In some embodiments, Form E is solvated. In some embodiments, Form E is solvated with toluene.

Compound 1, Form F

Figure 16:
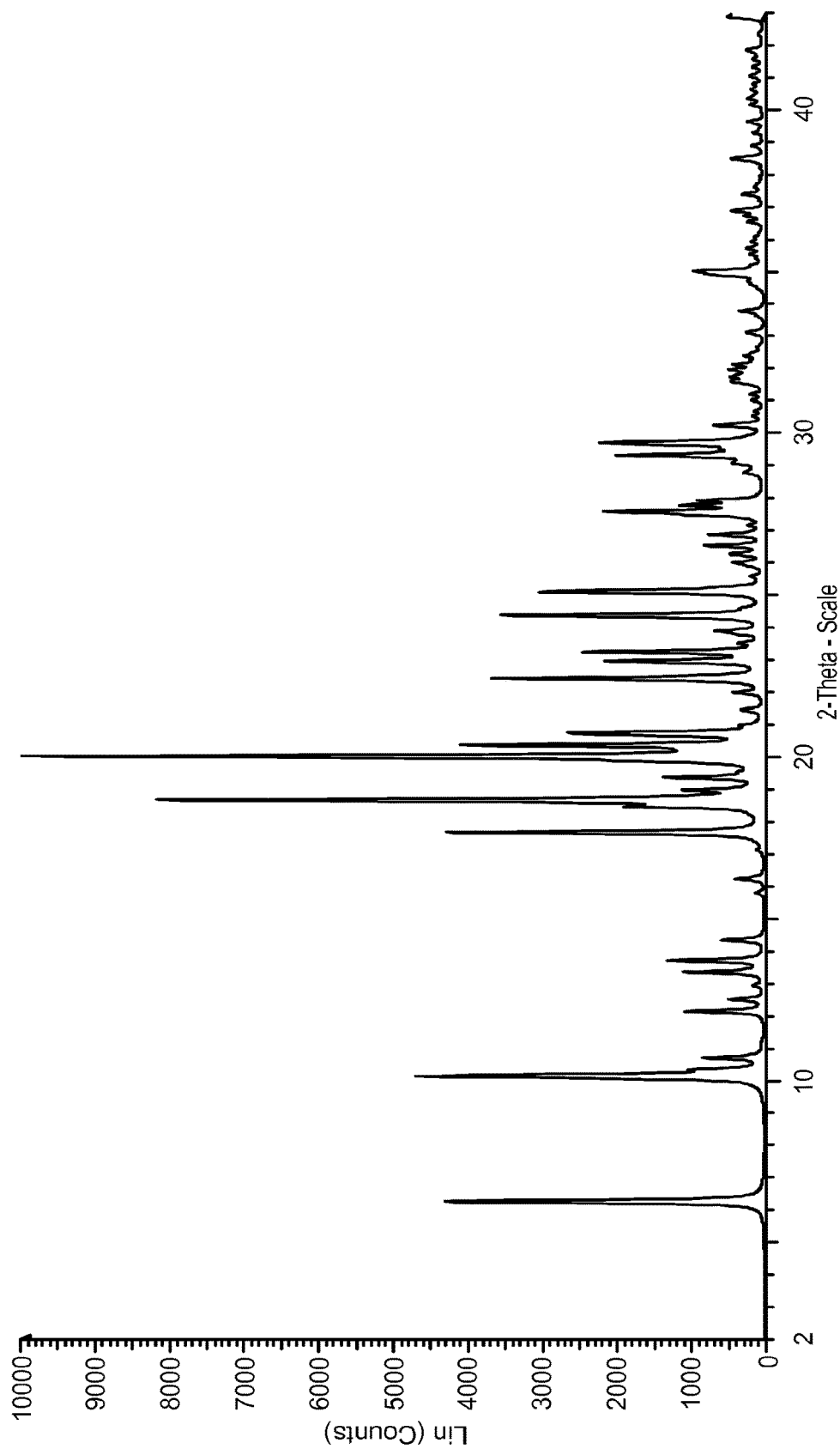
FIG. 16. Illustrates a simulated X-Ray powder diffraction (XRPD) pattern of Form F.

In some embodiments, Compound 1 is crystalline. In some embodiments, Compound 1 is crystalline Form F. Crystalline Form F of Compound 1 is characterized as having at least one of the following properties:

(a) an X-Ray powder diffraction (XRPD) pattern substantially the same as shown in FIG. 16;

(b) an X-ray powder diffraction (XRPD) pattern with characteristic peaks at 6.2±0.10 2-Theta, 10.1±0.1° 2-Theta, 17.6±0.1° 2-Theta, 18.6±0.1° 2-Theta, 20.0±0.1° 2-Theta, 20.4±0.10 2-Theta, 20.7±0.10 2-Theta, 22.4±0.10 2-Theta, 23.0±0.10 2-Theta, 23.2±0.10 2-Theta, 24.4±0.10 2-Theta, 25.1±0.10 2-Theta, 27.6±0.10 2-Theta, 29.3±0.10 2-Theta, and 29.7±0.10 2-Theta;

(c) unit cell parameters substantially equal to the following at 100(2) K:

| Crystal system | | Triclinic | | |
|---|---|---|---|---|
| Space group | P1 | a  9.6332(3) Å | α | 105.762(3)° |
| | | b  9.7536(4) Å | β | 95.132(2)° |
| | | c  15.0592(4) Å | γ | 111.332(3)° |
| V | | 1240.15(7) Å$^3$ | | |
| Z | | 1 | | |
| Density (calculated) | | 1.308 Mg/m$^3$ | | |
| Absorption coefficient | | 0.726 mm$^{-1}$ | | |
| Wavelength | | 1.54178 Å | | |
| F(000) | | 518 | | | or (d) combinations thereof.

In some embodiments, Form F of Compound 1 is characterized as having at least two of the properties selected from (a) to (c). In some embodiments, Form F of Compound 1 is characterized as having properties (a), (a), and (c).

In some embodiments, Form F has an X-Ray powder diffraction (XRPD) pattern substantially the same as shown in FIG. 16. In some embodiments, Form F has an X-ray powder diffraction (XRPD) pattern with characteristic peaks at 6.2±0.1° 2-Theta, 10.1±0.1° 2-Theta, 17.6±0.10 2-Theta, 18.6±0.10 2-Theta, 20.0±0.10 2-Theta, 20.4±0.10 2-Theta, 20.7±0.10 2-Theta, 22.4±0.10 2-Theta, 23.0±0.10 2-Theta, 23.2±0.10 2-Theta, 24.4±0.1° 2-Theta, 25.1±0.10 2-Theta, 27.6±0.1° 2-Theta, 29.3±0.1° 2-Theta, and 29.7±0.10 2-Theta.

In some embodiments, Form F has unit cell parameters substantially equal to the following at 100(2) K:

| Crystal system | | Triclinic | | |
|---|---|---|---|---|
| Space group | P1 | a  9.6332(3) Å | α | 105.762(3)° |
| | | b  9.7536(4) Å | β | 95.132(2)° |
| | | c  15.0592(4) Å | γ | 111.332(3)° |
| V | | 1240.15(7) Å$^3$ | | |
| Z | | 1 | | |
| Density (calculated) | | 1.308 Mg/m$^3$ | | |
| Absorption coefficient | | 0.726 mm$^{-1}$ | | |
| Wavelength | | 1.54178 Å | | |
| F(000) | | 518 | | |

In some embodiments, Form F was obtained from methanol.

In some embodiments, Form F is solvated. In some embodiments, Form F is solvated with methanol.

Preparation of Crystalline Forms

In some embodiments, crystalline forms of 1-((R)-3-(4-amino-3-(4-phenoxyphenyl)-1H-pyrazolo[3,4-d]pyrimidin-1-yl)piperidin-1-yl)prop-2-en-1-one are prepared as outlined in the Examples. It is noted that solvents, temperatures and other reaction conditions presented herein may vary.

Suitable Solvents

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

Residual solvents in active pharmaceutical ingredients (APIs) originate from the manufacture of API. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising Compound 1 comprise an organic solvent(s). In some embodiments, compositions comprising Compound 1 comprise a residual amount of an organic solvent(s). In some embodiments, compositions comprising Compound 1 comprise a residual amount of a Class 3 solvent. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the Class 3 solvent is selected from ethyl acetate, isopropyl acetate, tert-butylmethylether, heptane, isopropanol, and ethanol.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, the term "agonist" refers to a compound, the presence of which results in a biological activity of a protein that is the same as the biological activity resulting from the presence of a naturally occurring ligand for the protein, such as, for example, Btk.

As used herein, the term "partial agonist" refers to a compound the presence of which results in a biological activity of a protein that is of the same type as that resulting from the presence of a naturally occurring ligand for the protein, but of a lower magnitude.

As used herein, the term "antagonist" refers to a compound, the presence of which results in a decrease in the magnitude of a biological activity of a protein. In certain embodiments, the presence of an antagonist results in complete inhibition of a biological activity of a protein, such as, for example, Btk. In certain embodiments, an antagonist is an inhibitor.

As used herein, "amelioration" of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of Compound 1 dosed that is delivered into the general circulation of the animal or human being studied. The total exposure ($AUC_{(0-\infty)}$) of a drug when administered intravenously is usually defined as 100% bioavailable (F %). "Oral bioavailability" refers to the extent to which Compound 1 is absorbed into the general circulation when the pharmaceutical composition is taken orally as compared to intravenous injection.

"Blood plasma concentration" refers to the concentration of Compound 1 in the plasma component of blood of a subject. It is understood that the plasma concentration of Compound 1 may vary significantly between subjects, due to variability with respect to metabolism and/or possible interactions with other therapeutic agents. In accordance with one embodiment disclosed herein, the blood plasma concentration of Compound 1 may vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of Compound 1 may vary from subject to subject.

The term "Bruton's tyrosine kinase," as used herein, refers to Bruton's tyrosine kinase from *Homo sapiens*, as disclosed in, e.g., U.S. Pat. No. 6,326,469 (GenBank Accession No. NP_000052).

The term "Bruton's tyrosine kinase homolog," as used herein, refers to orthologs of Bruton's tyrosine kinase, e.g., the orthologs from mouse (GenBank Acession No. AAB47246), dog (GenBank Acession No. XP_549139.), rat (GenBank Acession No. NP_001007799), chicken (GenBank Acession No. NP_989564), or zebra fish (GenBank Acession No. XP_698117), and fusion proteins of any of the foregoing that exhibit kinase activity towards one or more substrates of Bruton's tyrosine kinase (e.g. a peptide substrate having the amino acid sequence "AVLESEEELYSSARQ").

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of Compound 1, age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

The term "homologous cysteine," as used herein refers to a cysteine residue found with in a sequence position that is homologous to that of cysteine 481 of Bruton's tyrosine kinase, as defined herein. For example, cysteine 482 is the homologous cysteine of the rat ortholog of Bruton's tyrosine kinase; cysteine 479 is the homologous cysteine of the chicken ortholog; and cysteine 481 is the homologous cysteine in the zebra fish ortholog. In another example, the homologous cysteine of TXK, a Tec kinase family member related to Bruton's tyrosine, is Cys 350. Other examples of kinases having homologous cysteines are shown in FIG. 1. See also the sequence alignments of tyrosine kinases (TK) published on the world wide web at kinase.com/human/kinome/phylogeny.html.

The term "identical," as used herein, refers to two or more sequences or subsequences which are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages to describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75-100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75-100 nucleic acids in length, over a region that is about 50 nucleic acids in length, or, where not specified, across the entire sequence of a polynucleotide sequence.

The terms "inhibits", "inhibiting", or "inhibitor" of a kinase, as used herein, refer to inhibition of enzymatic phosphotransferase activity.

The term "irreversible inhibitor," as used herein, refers to a compound that, upon contact with a target protein (e.g., a kinase) causes the formation of a new covalent bond with or within the protein, whereby one or more of the target protein's biological activities (e.g., phosphotransferase activity) is diminished or abolished notwithstanding the subsequent presence or absence of the irreversible inhibitor.

The term "irreversible Btk inhibitor," as used herein, refers to an inhibitor of Btk that can form a covalent bond with an amino acid residue of Btk. In one embodiment, the irreversible inhibitor of Btk can form a covalent bond with a Cys residue of Btk; in particular embodiments, the irreversible inhibitor can form a covalent bond with a Cys 481 residue (or a homolog thereof) of Btk or a cysteine residue in the homologous corresponding position of another tyrosine kinase.

The term "isolated," as used herein, refers to separating and removing a component of interest from components not of interest. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production. Also, by way of example, a gene is isolated when separated from open reading frames which flank the gene and encode a protein other than the gene of interest.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "prophylactically effective amount," as used herein, refers that amount of a composition applied to a patient which will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The term "subject" as used herein, refers to an animal which is the object of treatment, observation or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

As used herein, the term "target protein" refers to a molecule or a portion of a protein capable of being bound by a selective binding compound. In certain embodiments, a target protein is Btk.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, the $IC_{50}$ refers to an amount, concentration or dosage of a particular test compound that achieves a 50% inhibition of a maximal response, such as inhibition of Btk, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

Pharmaceutical Compositions/Formulations

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

A pharmaceutical composition, as used herein, refers to a mixture of Compound 1 with other chemical components, such as carriers, stabilizers, diluents, dispersing agents, suspending agents, thickening agents, and/or excipients. The pharmaceutical composition facilitates administration of the compound to a mammal. In practicing the methods of treatment or use provided herein, therapeutically effective amounts of Compound 1 are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The term "pharmaceutical combination" as used herein, means a product that results from the mixing or combining of more than one active ingredient and includes both fixed and non-fixed combinations of the active ingredients. The term "fixed combination" means that the active ingredients, e.g. Compound 1 and a co-agent, are both administered to a patient simultaneously in the form of a single entity or dosage. The term "non-fixed combination" means that the active ingredients, e.g. Compound 1 and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

In some embodiments, crystalline Compound 1 is incorporated into pharmaceutical compositions to provide solid oral dosage forms. In other embodiments, crystalline Compound 1 is used to prepare pharmaceutical compositions other than oral solid dosage forms. The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

Dosage Forms

The pharmaceutical compositions described herein can be formulated for administration to a mammal via any conventional means including, but not limited to, oral, parenteral (e.g., intravenous, subcutaneous, or intramuscular), buccal, intranasal, rectal or transdermal administration routes. As used herein, the term "subject" is used to mean an animal, preferably a mammal, including a human or non-human. The terms patient and subject may be used interchangeably.

Moreover, the pharmaceutical compositions described herein, which include Compound 1 can be formulated into any suitable dosage form, including but not limited to, solid oral dosage forms, controlled release formulations, fast melt formulations, effervescent formulations, tablets, powders, pills, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bio-erodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of Compound 1 with one or more pharmaceutical excipients to form a bulk blend composition. When referring to these bulk blend compositions as homogeneous, it is meant that the particles of Compound 1 are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can include Compound 1 and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the formulation of Compound 1. In one embodiment, some or all of the particles of the Compound 1 are coated. In another embodiment, some or all of the particles of the Compound 1 are microencapsulated. In still another embodiment, the particles of the Compound 1 are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethylcellulose (HPMC), hydroxypropylmethylcellulose phthalate, hydroxypropylmethylcellulose acetate stearate (HPMCAS), sucrose, xylitol, lactitol, mannitol, sorbitol, sodium chloride, polyethylene glycol, and the like.

In order to release the Compound 1 from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like. In some embodiments provided herein, the disintegrating agent is selected from the group consisting of natural starch, a pregelatinized starch, a sodium starch, methylcrystalline cellulose, methylcellulose, croscarmellose, croscarmellose sodium, cross-linked sodium carboxymethylcellulose, cross-linked carboxymethylcellulose, cross-linked croscarmellose, cross-linked starch such as sodium starch glycolate, cross-linked polymer such as crospovidone, cross-linked polyvinylpyrrolidone, sodium alginate, a clay, or a gum. In some embodiments provided herein, the disintegrating agent is croscarmellose sodium.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like. In some embodiments provided herein, the lubricant is selected from the group consisting of stearic acid, calcium hydroxide, talc, corn starch, sodium stearyl fumerate, stearic acid, sodium stearates, magnesium stearate, zinc stearate, and waxes. In some embodiments provided herein, the lubricant is magnesium stearate.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like. In some embodiments provided herein, the diluent is selected from the group consisting of lactose, sucrose, dextrose, dextrates, maltodextrin, mannitol, xylitol, sorbitol, cyclodextrins, calcium phosphate, calcium sulfate, starches, modified starches, microcrystalline cellulose, microcellulose, and talc. In some embodiments provided herein, the diluent is microcrystalline cellulose.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. In some embodiments provided herein, the surfactant is selected from the group consisting of sodium lauryl sulfate, sorbitan monooleate, polyoxyethylene sorbitan monooleate, polysorbates, polaxomers, bile salts, glyceryl monostearate, copolymers of ethylene oxide and propylene oxide. In some embodiments provided herein, the surfactant is sodium lauryl sulfate.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of Compound 1 from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of Compound 1 inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of Compound 1 and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with Compound 1 which sufficiently isolate the Compound 1 from other non-compatible excipients. Materials compatible with Compound 1 are those that delay the release of the compounds of Compound 1 in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated Compound 1 may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In one embodiment, the particles of Compound 1 are microencapsulated prior to being formulated into one of the above forms. In still another embodiment, some or most of the particles are coated prior to being further formulated by using standard coating procedures, such as those described in *Remington's Pharmaceutical Sciences,* 20th Edition (2000).

In other embodiments, the solid dosage formulations of the Compound 1 are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with Compound 1 may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In other embodiments, the polymers and compatible mixtures thereof, and some of their properties, include, but are not limited to:

Shellac, also called purified lac, a refined product obtained from the resinous secretion of an insect. This coating dissolves in media of pH>7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles<1 µm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions; Poly Vinyl Acetate Phthalate (PVAP). PVAP dissolves in pH>5, and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include Compound 1 are delivered using a pulsatile dosage form. A pulsatile dosage form is capable of providing one or more immediate release pulses at predetermined time points after a controlled lag time or at specific sites. Many other types of controlled release systems known to those of ordinary skill in the art and are suitable for use with the formulations described herein. Examples of such delivery systems include, e.g., polymer-based systems, such as polylactic and polyglycolic acid, plyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms*, 2 Ed., Vol. 1, pp. 209-214 (1990); Singh et al., *Encyclopedia of Pharmaceutical Technology*, $2^{nd}$ Ed., pp. 751-753 (2002); U.S. Pat. Nos. 4,327,725, 4,624,848, 4,968, 509, 5,461,140, 5,456,923, 5,516,527, 5,622,721, 5,686,105, 5,700,410, 5,977,175, 6,465,014 and 6,932,983, each of which is specifically incorporated by reference.

In some embodiments, pharmaceutical formulations are provided that include particles of Compound 1 at least one dispersing agent or suspending agent for oral administration to a subject. The formulations may be a powder and/or granules for suspension, and upon admixture with water, a substantially uniform suspension is obtained.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Dosing and Treatment Regimens

In some embodiments, the amount of Compound 1 that is administered to a mammal is from 300 mg/day up to, and including, 1000 mg/day. In some embodiments, the amount of Compound 1 that is administered to a mammal is from 420 mg/day up to, and including, 840 mg/day. In some embodiments, the amount of Compound 1 that is administered to a mammal is about 420 mg/day, about 560 mg/day, or about 840 mg/day. In some embodiments, the amount of Compound 1 that is administered to a mammal is about 420 mg/day. In some embodiments, the amount of Compound 1 that is administered to a mammal is about 560 mg/day. In some embodiments, the $AUC_{0-24}$ of Compound 1 is between about 150 and about 3500 ng*h/mL. In some embodiments, the $AUC_{0-24}$ of Compound 1 is between about 500 and about 1100 ng*h/mL. In some embodiments, Compound 1 is administered orally. In some embodiments, Compound 1 is administered once per day, twice per day, or three times per day. In some embodiments, Compound 1 is administered daily. In some embodiments, Compound 1 is administered once daily. In some embodiments, Compound 1 is administered every other day. In some embodiments, the Compound 1 is a maintenance therapy.

Compound 1 can be used in the preparation of medicaments for the inhibition of Btk or a homolog thereof, or for the treatment of diseases or conditions that would benefit, at least in part, from inhibition of Btk or a homolog thereof, including a subject diagnosed with a hematological malignancy. In addition, a method for treating any of the diseases or conditions described herein in a subject in need of such treatment, involves administration of pharmaceutical compositions containing Compound 1, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

The compositions containing Compound 1 can be administered for prophylactic, therapeutic, or maintenance treatment. In some embodiments, compositions containing Compound 1 are administered for therapeutic applications (e.g., administered to a subject diagnosed with a hematological malignancy). In some embodiments, compositions containing Compound 1 are administered for therapeutic applications (e.g., administered to a subject susceptible to or otherwise at risk of developing a hematological malignancy). In some embodiments, compositions containing Compound 1 are administered to a patient who is in remission as a maintenance therapy.

Amounts of Compound 1 will depend on the use (e.g., therapeutic, prophylactic, or maintenance). Amounts of Compound 1 will depend on severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial). In some embodiments, the amount of Compound 1 is from 300 mg/day up to, and including, 1000 mg/day. In some embodiments, the amount of Compound 1 is from 420 mg/day up to, and including, 840 mg/day. In some embodiments, the amount of Compound 1 is from 400 mg/day up to, and including, 860 mg/day. In some embodiments, the amount of Compound 1 is about 360 mg/day. In some embodiments, the amount of Compound 1 is about 420 mg/day. In some embodiments, the amount of Compound 1 is about 560 mg/day. In some embodiments, the amount of Compound 1 is about 840 mg/day. In some embodiments, the amount of Compound 1 is from 2 mg/kg/day up to, and including, 13 mg/kg/day. In some embodiments, the amount of Compound 1 is from 2.5 mg/kg/day up to, and including, 8 mg/kg/day. In some embodiments, the amount of Compound 1 is from 2.5 mg/kg/day up to, and including, 6 mg/kg/day. In some embodiments, the amount of Compound 1 is from 2.5 mg/kg/day up to, and including, 4 mg/kg/day. In some embodiments, the amount of Compound 1 is about 2.5 mg/kg/day. In some embodiments, the amount of Compound 1 is about 8 mg/kg/day.

In some embodiments, pharmaceutical compositions described herein include about 140 mg of Compound 1. In some embodiments, a capsule formulation is prepared that includes about 140 mg of Compound 1. In some embodiments, 2, 3, 4, or 5 of the capsule formulations are administered daily. In some embodiments, 3 or 4 of the capsules are administered daily. In some embodiments, 3 of the 140 mg capsules are administered once daily. In some embodiments, 4 of the 140 mg capsules are administered once daily. In some embodiments, the capsules are administered once daily. In other embodiments, the capsules are administered multiple times a day.

In some embodiments, Compound 1 is administered daily. In some embodiments, Compound 1 is administered every other day.

In some embodiments, Compound 1 is administered once per day. In some embodiments, Compound 1 is administered twice per day. In some embodiments, Compound 1 is administered three times per day. In some embodiments, Compound 1 is administered four times per day.

In some embodiments, Compound 1 is administered until disease progression, unacceptable toxicity, or individual choice. In some embodiments, Compound 1 is administered daily until disease progression, unacceptable toxicity, or individual choice. In some embodiments, Compound 1 is administered every other day until disease progression, unacceptable toxicity, or individual choice.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, the severity of the disease, the identity (e.g., weight) of the subject or host in need of treatment, but can nevertheless be routinely determined in a manner known in the art according to the particular circumstances surrounding the case, including, e.g., the specific agent being administered, the route of administration, and the subject or host being treated. In general, however, doses employed for adult human treatment will typically be in the range of 0.02-5000 mg per day, or from about 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative. In some embodiments, each unit dosage form comprises 140 mg of Compound 1. In some embodiments, an individual is administered 1 unit dosage form per day. In some embodiments, an individual is administered 2 unit dosage forms per day. In some embodiments, an individual is administered 3 unit dosage forms per day. In some embodiments, an individual is administered 4 unit dosage forms per day.

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Therapy

In certain instances, it is appropriate to administer Compound 1 in combination with another therapeutic agent.

In one embodiment, the compositions and methods described herein are also used in conjunction with other therapeutic reagents that are selected for their particular usefulness against the condition that is being treated. In general, the compositions described herein and, in embodiments where combinational therapy is employed, other agents do not have to be administered in the same pharmaceutical composition, and are, because of different physical and chemical characteristics, administered by different routes. In one embodiment, the initial administration is made according to established protocols, and then, based upon the observed effects, the dosage, modes of administration and times of administration, further modified.

In various embodiments, the compounds are administered concurrently (e.g., simultaneously, essentially simultaneously or within the same treatment protocol) or sequentially, depending upon the nature of the disease, the condition of the patient, and the actual choice of compounds used. In certain embodiments, the determination of the order of administration, and the number of repetitions of administration of each therapeutic agent during a treatment protocol, is based upon evaluation of the disease being treated and the condition of the patient.

For combination therapies described herein, dosages of the co-administered compounds vary depending on the type of co-drug employed, on the specific drug employed, on the disease or condition being treated and so forth.

The individual compounds of such combinations are administered either sequentially or simultaneously in separate or combined pharmaceutical formulations. In one embodiment, the individual compounds will be administered simultaneously in a combined pharmaceutical formulation. Appropriate doses of known therapeutic agents will be appreciated by those skilled in the art.

The combinations referred to herein are conveniently presented for use in the form of a pharmaceutical compositions together with a pharmaceutically acceptable diluent(s) or carrier(s).

Disclosed herein, in certain embodiments, is a method for treating a cancer in an individual in need thereof, comprising: administering to the individual an amount of Compound 1. In some embodiments, the method further comprises administering a second cancer treatment regimen.

In some embodiments, administering a Btk inhibitor before a second cancer treatment regimen reduces immune-mediated reactions to the second cancer treatment regimen. In some embodiments, administering Compound 1 before ofatumumab reduces immune-mediated reactions to ofatumumab.

In some embodiments, the second cancer treatment regimen comprises a chemotherapeutic agent, a steroid, an immunotherapeutic agent, a targeted therapy, or a combination thereof. In some embodiments, the second cancer treatment regimen comprises a B cell receptor pathway inhibitor. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, or a combination thereof. In some embodiments, the second cancer treatment regimen comprises an antibody, B cell receptor signaling inhibitor, a PI3K inhibitor, an IAP inhibitor, an mTOR inhibitor, a radioimmunotherapeutic, a DNA damaging agent, a proteosome inhibitor, a Cyp3A4 inhibitor, a histone deacetylase inhibitor, a protein kinase inhibitor, a hedgehog inhibitor, an Hsp90 inhibitor, a telomerase inhibitor, a Jak1/2 inhibitor, a protease inhibitor, a PKC inhibitor, a PARP inhibitor, or a combination thereof.

In some embodiments, the second cancer treatment regimen comprises chlorambucil, ifosphamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof.

In some embodiments, the second cancer treatment regimen comprises cyclophosphamide, hydroxydaunorubicin, vincristine, and prednisone, and optionally, rituximab.

In some embodiments, the second cancer treatment regimen comprises bendamustine, and rituximab.

In some embodiments, the second cancer treatment regimen comprises fludarabine, cyclophosphamide, and rituximab.

In some embodiments, the second cancer treatment regimen comprises cyclophosphamide, vincristine, and prednisone, and optionally, rituximab.

In some embodiments, the second cancer treatment regimen comprises etoposide, doxorubicin, vinristine, cyclophosphamide, prednisolone, and optionally, rituximab.

In some embodiments, the second cancer treatment regimen comprises dexamethasone and lenalidomide.

In some embodiments, the second cancer treatment comprises a proteasome inhibitor. In some embodiments, the second treatment comprises bortezomib. In some embodiments, the second cancer treatment comprises an epoxyketone. In some embodiments, the second cancer treatment comprises epoxomicin. In some embodiments, the second cancer treatment comprises a tetrapeptide epoxyketone In some embodiments, the second cancer treatment comprises carfilzomib. In some embodiments, the second cancer treatment comprises disulfram, epigallocatechin-3-gallate, salinosporamide A, ONX 0912m CEP-18770, MLN9708, or MG132.

In some embodiments, the second cancer treatment comprises a Cyp3A4 inhibitor. In some embodiments, the second cancer treatment comprises indinavir, nelfinavir, ritonavir, clarithromycin, itraconazole, ketoconazole, nefazodone. In some embodiments, the second cancer treatment comprises ketoconazole.

In some embodiments, the second cancer treatment comprises a Janus Kinase (JAK) inhibitor. In some embodiments, the second treatment comprises Lestaurtinib, Tofacitinib, Ruxolitinib, CYT387, Baricitinib or Pacritinib.

In some embodiments, the second cancer treatment comprises a histone deacetylase inhibitor (HDAC inhibitor, HDI). In some embodiments, the second cancer treatment comprises a hydroxamic acid (or hydroxamate), such as trichostatin A, vorinostat (SAHA), belinostat (PXD101), LAQ824, and panobinostat (LBH589), a cyclic tetrapeptide, such as trapoxin B, a depsipeptide, a benzamide, such as entinostat (MS-275), CI994, and mocetinostat (MGCD0103), an electrophilic ketone, or an aliphatic acid compound, such as phenylbutyrate and valproic acid, Additional cancer treatment regimens include Nitrogen Mustards such as for example, bendamustine, chlorambucil, chlormethine, cyclophosphamide, ifosfamide, melphalan, prednimustine, trofosfamide; Alkyl Sulfonates like busulfan, mannosulfan, treosulfan; Ethylene Imines like carboquone, thiotepa, triaziquone; Nitrosoureas like carmustine, fotemustine, lomustine, nimustine, ranimustine, semustine, streptozocin; Epoxides such as for example, etoglucid; Other Alkylating Agents such as for example dacarbazine, mitobronitol, pipobroman, temozolomide; Folic Acid Analogues such as for example methotrexate, permetrexed, pralatrexate, raltitrexed; Purine Analogs such as for example cladribine, clofarabine, fludarabine, mercaptopurine, nelarabine, tioguanine; Pyrimidine Analogs such as for example azacitidine, capecitabine, carmofur, cytarabine, decitabine, fluorouracil, gemcitabine, tegafur; Vinca Alkaloids such as for example vinblastine, vincristine, vindesine, vinflunine, vinorelbine; Podophyllotoxin Derivatives such as for example etoposide, teniposide; Colchicine derivatives such as for example demecolcine; Taxanes such as for example docetaxel, paclitaxel, paclitaxel poliglumex; Other Plant Alkaloids and Natural Products such as for example trabectedin; Actinomycines such as for example dactinomycin; Antracyclines such as for example aclarubicin, daunorubicin, doxorubicin, epirubicin, idarubicin, mitoxantrone, pirarubicin, valrubicin, zorubincin; Other Cytotoxic Antibiotics such as for example bleomycin, ixabepilone, mitomycin, plicamycin; Platinum Compounds such as for example carboplatin, cisplatin, oxaliplatin, satraplatin; Methylhydrazines such as for example procarbazine; Sensitizers such as for example aminolevulinic acid, efaproxiral, methyl aminolevulinate, porfimer sodium, temoporfin; Protein Kinase Inhibitors such as for example dasatinib, erlotinib, everolimus, gefitinib, imatinib, lapatinib, nilotinib, pazonanib, sorafenib, sunitinib, temsirolimus; Other Antineoplastic Agents such as for example alitretinoin, altretamine, amzacrine, anagrelide, arsenic trioxide, asparaginase, bexarotene, bortezomib, celecoxib, denileukin diftitox, estramustine, hydroxycarbamide, irinotecan, lonidamine, masoprocol, miltefosein, mitoguazone, mitotane, oblimersen, pegaspargase, pentostatin, romidepsin, sitimagene ceradenovec, tiazofurine, topotecan, tretinoin, vorinostat; Estrogens such as for example diethylstilbenol, ethinylestradiol, fosfestrol, polyestradiol phosphate; Progestogens such as for example gestonorone, medroxyprogesterone, megestrol; Gonadotropin Releasing Hormone Analogs such as for example buserelin, goserelin, leuprorelin, triptorelin; Anti-Estrogens such as for example fulvestrant, tamoxifen, toremifene; Anti-Androgens such as for example bicalutamide, flutamide, nilutamide, Enzyme Inhibitors, aminoglutethimide, anastrozole, exemestane, formestane, letrozole, vorozole; Other Hormone Antagonists such as for example abarelix, degarelix; Immunostimulants such as for example histamine dihydrochloride, mifamurtide, pidotimod, plerixafor, roquinimex, thymopentin; Immunosuppressants such as for example everolimus, gusperimus, leflunomide, mycophenolic acid, sirolimus; Calcineurin Inhibitors such as for example ciclosporin, tacrolimus; Other Immunosuppressants such as for example azathioprine, lenalidomide, methotrexate, thalidomide; and Radiopharmaceuticals such as for example, iobenguane.

Additional cancer treatment regimens include interferons, interleukins, Tumor Necrosis Factors, Growth Factors, or the like.

Additional cancer treatment regimens include Immunostimulants such as for example ancestim, filgrastim, lenograstim, molgramostim, pegfilgrastim, sargramostim; Interferons such as for example interferon alfa natural, interferon alfa-2a, interferon alfa-2b, interferon alfacon-1, interferon alfa-n1, interferon beta natural, interferon beta-1a, interferon beta-1b, interferon gamma, peginterferon alfa-2a, peginterferon alfa-2b; Interleukins such as for example aldesleukin, oprelvekin; Other Immunostimulants such as for example BCG vaccine, glatiramer acetate, histamine dihydrochloride, immunocyanin, lentinan, melanoma vaccine, mifamurtide, pegademase, pidotimod, plerixafor, poly I:C, poly ICLC, roquinimex, tasonermin, thymopentin; Immunosuppressants such as for example abatacept, abetimus, alefacept, antilymphocyte immunoglobulin (horse), antithymocyte immunoglobulin (rabbit), eculizumab, efalizumab, everolimus, gusperimus, leflunomide, muromab-CD3, mycophenolic acid, natalizumab, sirolimus; TNF alpha Inhibitors such as for example adalimumab, afelimomab, certolizumab pegol, etanercept, golimumab, infliximab; Interleukin Inhibitors such as for example anakinra, basiliximab, canakinumab, daclizumab, mepolizumab, rilonacept, tocilizumab, ustekinumab; Calcineurin Inhibitors such as for example ciclosporin, tacrolimus; Other Immunosuppressants such as for example azathioprine, lenalidomide, methotrexate, thalidomide.

Additional cancer treatment regimens include Adalimumab, Alemtuzumab, Basiliximab, Bevacizumab, Cetuximab, Certolizumab pegol, Daclizumab, Eculizumab, Efalizumab, Gemtuzumab, Ibritumomab tiuxetan, Infliximab, Muromonab-CD3, Natalizumab, Panitumumab, Ranibizumab, Rituximab, Tositumomab, Trastuzumab, or the like, or a combination thereof.

Additional cancer treatment regimens include Monoclonal Antibodies such as for example alemtuzumab, bevacizumab, catumaxomab, cetuximab, edrecolomab, gemtuzumab, ofatumumab, panitumumab, rituximab, trastuzumab, Immunosuppressants, eculizumab, efalizumab, muromab-CD3, natalizumab; TNF alpha Inhibitors such as for example adalimumab, afelimomab, certolizumab pegol, golimumab, infliximab, Interleukin Inhibitors, basiliximab, canakinumab, daclizumab, mepolizumab, tocilizumab, ustekinumab, Radiopharmaceuticals, ibritumomab tiuxetan, tositumomab; Others Monoclonal Antibodies such as for example abagovomab, adecatumumab, alemtuzumab, anti-CD30 monoclonal antibody Xmab2513, anti-MET monoclonal antibody MetMab, apolizumab, apomab, arcitumomab, basiliximab, bispecific antibody 2B1, blinatumomab, brentuximab vedotin, capromab pendetide, cixutumumab, claudiximab, conatumumab, dacetuzumab, denosumab, eculizumab, epratuzumab, epratuzumab, ertumaxomab, etaracizumab, figitumumab, fresolimumab, galiximab, ganitumab, gemtuzumab ozogamicin, glembatumumab, ibritumomab, inotuzumab ozogamicin, ipilimumab, lexatumumab, lintuzumab, lintuzumab, lucatumumab, mapatumumab, matuzumab, milatuzumab, monoclonal antibody CC49, necitumumab, nimotuzumab, ofatumumab, oregovomab, pertuzumab, ramacurimab, ranibizumab, siplizumab, sonepcizumab, tanezumab, tositumomab, trastuzumab, tremelimumab, tucotuzumab celmoleukin, veltuzumab, visilizumab, volociximab, zalutumumab.

Additional cancer treatment regimens include agents that affect the tumor micro-environment such as cellular signaling network (e.g. phosphatidylinositol 3-kinase (PI3K) signaling pathway, signaling from the B-cell receptor and the IgE receptor). In some embodiments, the second agent is a PI3K signaling inhibitor or a syc kinase inhibitor. In one embodiment, the syk inhibitor is R788. In another embodiment is a PKCγ inhibitor such as by way of example only, enzastaurin.

Examples of agents that affect the tumor micro-environment include PI3K signaling inhibitor, syc kinase inhibitor, Protein Kinase Inhibitors such as for example dasatinib, erlotinib, everolimus, gefitinib, imatinib, lapatinib, nilotinib, pazonanib, sorafenib, sunitinib, temsirolimus; Other Angiogenesis Inhibitors such as for example GT-111, JI-101, R1530; Other Kinase Inhibitors such as for example AC220, AC480, ACE-041, AMG 900, AP24534, Arry-614, AT7519, AT9283, AV-951, axitinib, AZD1152, AZD7762, AZD8055, AZD8931, bafetinib, BAY 73-4506, BGJ398, BGT226, BI 811283, BI6727, BIBF 1120, BIBW 2992, BMS-690154, BMS-777607, BMS-863233, BSK-461364, CAL-101, CEP-11981, CYC116, DCC-2036, dinaciclib, dovitinib lactate, E7050, EMD 1214063, ENMD-2076, fostamatinib disodium, GSK2256098, GSK690693, INCB18424, INNO-406, JNJ-26483327, JX-594, KX2-391, linifanib, LY2603618, MGCD265, MK-0457, MK1496, MLN8054, MLN8237, MP470, NMS-1116354, NMS-1286937, ON 01919.Na, OSI-027, OSI-930, Btk inhibitor, PF-00562271, PF-02341066, PF-03814735, PF-04217903, PF-04554878, PF-04691502, PF-3758309, PHA-739358, PLC3397, progenipoietin, R547, R763, ramucirumab, regorafenib, RO5185426, SAR103168, SCH 727965, SGI-1176, SGX523, SNS-314, TAK-593, TAK-901, TKI258, TLN-232, TTP607, XL147, XL228, XL281RO5126766, XL418, XL765.

Further examples of anti-cancer agents for use in combination with a Btk inhibitor compound include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a Btk inhibitor compound include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a Btk inhibitor compound include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-such as for example growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a Btk inhibitor compound include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of alkylating agents that can be employed in combination a Btk inhibitor compound include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of anti-cancer agents which act by arresting cells in the G2-M phases due to stabilized microtubules and which can be used in combination with a Btk inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCI), AC-7700 (Ajinomoto, also known as AVE-8062, AVE-8062A, CS-39-L-Ser.HCI, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, lnanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Where the individual is suffering from or at risk of suffering from an autoimmune disease, an inflammatory disease, or an allergy disease, Compound 1 can be used in with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, allergy vaccines, antihistamines, antileukotrienes, beta-agonists, theophylline, or anticholinergics.

Kits/Articles of Manufacture

For use in the therapeutic methods of use described herein, kits and articles of manufacture are also described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Packaging materials for use in packaging pharmaceutical products include, e.g., U.S. Pat. No. 5,323, 907. Examples of pharmaceutical packaging materials include, but are not limited to, blister packs, bottles, tubes, bags, containers, bottles, and any packaging material suitable for a selected formulation and intended mode of administration and treatment.

In some embodiments, the compounds or compositions described herein, are presented in a package or dispenser device which may contain one or more unit dosage forms containing the active ingredient. The compound or composition described herein is packaged alone, or packaged with another compound or another ingredient or additive. In some embodiments, the package contains one or more containers filled with one or more of the ingredients of the pharmaceutical compositions. In some embodiments, the package comprises metal or plastic foil, such as a blister pack. In some embodiments, the package or dispenser device is accompanied by instructions for administration, such as instructions for administering the compounds or compositions for treating a neoplastic disease. In some embodiments, the package or dispenser is accompanied with a notice associated with the container in form prescribed by a governmental agency regulating the manufacture, use, or sale of pharmaceuticals, which notice is reflective of approval by the agency of the form of the drug for human or veterinary administration. In some embodiments, such notice, for example, is the labeling approved by the U.S. Food and Drug Administration for prescription drugs, or the approved product insert. In some embodiments, compositions include a compound described herein formulated in a compatible pharmaceutical carrier are prepared, placed in an appropriate container, and labeled for treatment of an indicated condition.

For example, the container(s) include Compound 1, optionally in a composition or in combination with another agent as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

EXAMPLES

The following ingredients, formulations, processes and procedures for practicing the methods disclosed herein correspond to that described above.

Example 1: Preparation of Crystalline Forms of 1-((R)-3-(4-amino-3-(4-phenoxyphenyl)-1H-pyrazolo[3,4-d]pyrimidin-1-yl)piperidin-1-yl)prop-2-en-1-one (Compound 1)

Form A—Route 1:

Amorphous Compound 1 (ca. 15 mg) was measured into a vial. Ten volumes (150 μl) of solvent [methyl tert-butyl ether (MTBE), diisopropyl ether (DIPE), ethyl acetate, isopropyl acetate, isopropyl alcohol, methyl isobutyl ketone (MIBK), methyl ethyl ketone (MEK), acetone, methanol, nitromethane, 10% aqueous acetone, or 10% aqueous isopropyl alcohol] were added to the vial. The vial was sealed and placed in a shaker at 50° C. for one hour. If a slurry was obtained, an additional thirty volumes (total of 600 μl) of solvent was added, then the slurry was returned to 50° C. for another hour. If the sample remained as a slurry at this point, no further solvent was added. The solution/slurry was stirred at 50° C. for one hour, then cooled to 0° C. at 0.1° C./min, then held at 0° C. overnight. If a slurry was obtained, the solids were filtered under vacuum to provide Compound 1, Form A; the solution was returned to ambient temperature for slow evaporation through a pin-hole to furnish Compound 1, Form A.

Form A—Route 2:

Amorphous Compound 1 (20 mg) was added to a vial, followed by solvent [heptanes (10 volumes), dioxane (1 volume), toluene (10 volumes), MTBE (10 volumes), DIPE (10 volumes), anisole (1 volume), ethyl acetate (10 volumes), isopropyl acetate (10 volumes), tetrahydrofuran (1 volume), DCM (1 volume), MIBK (10 volumes), MEK (10 volumes), acetone (10 volumes), methanol (10 volumes), ethanol (10 volumes), acetonitrile (10 volumes), nitromethane (1 volume), water (10 volumes), or 10% aqueous isopropyl alcohol (1 volume)]. The sealed vial was placed in a maturation chamber (cycling between 50° C. and ambient for four hours each) for five days before the solids were filtered under vacuum to provide Compound 1, Form A.

In some embodiments, amorphous Compound 1 is prepared by dissolving Compound 1, Form A (ca. 500 mg) in 10 ml dichloromethane (DCM). The solvent was removed by rotary evaporation, occurring rapidly enough to prevent crystallization to provide amorphous Compound 1.

Form A—Route 3:

In a clean round bottom flask, 12.0 grams of Compound 1 were dissolved in 120 ml of methanol by heating to 45° C. with magnetic stirring. To the warm solution of dissolved Compound 1 was added 72 ml of water over 45 min, maintaining the internal temperature at 45° C. The solution slowly became a slurry and was stirred for 3 hours at the elevated temperature. A sample of the slurry was drawn, filtered and dried. The slurry was allowed to cool to room temperature and stirred for at least 16 hours. Another sample of the slurry was drawn, filtered and dried. The solids were filtered, washed with 50 ml of a 3:2 mixture of methanol:water, and dried on the filter for 40 hours. Yield 9.6 grams of Form A (melting points: 1st sample ~152° C., $2^{nd}$ sample ~154° C., main lot ~154° C.).

Form A was also attained in an analogous manner using aqueous acetone, ethanol, and n-propanol.

Form B—Route 1:

Compound 1, Form A (ca. 100 mg) was weighed into a vessel and dissolved in methanol (2 ml). The solution was heated to 50° C. to ensure full dissolution, then cooled to 5° C. Water was added to the solution at 5° C. (200 μl at a time until sample became cloudy, totaling 1000 μl). Seeds of Compound 1, Form C were added immediately upon appearance of cloudiness. The slurry was stirred at 5° C. for one day. An aliquot was removed by pipette for analysis by XRPD, keeping the bulk of the sample in the same conditions. The XRPD analysis highlighted the low crystallinity of the material, so the sample was held at 5° C. for an additional three days. After this time, re-analysis of an aliquot of the sample showed the material to have converted to Compound 1, Form B. The sample was isolated by filtration under vacuum to provide Compound 1, Form B.

Form B—Route 2:

Compound 1, Form A (ca. 500 mg) was weighed into a vessel and dissolved in methanol (4 ml) at 50° C. The solution was cooled to 25° C., remaining in solution. Water was added (500 μl of water added at a time, 2 ml in total) until the solution became cloudy. The slurry was stirred for ten minutes. An aliquot was removed by pipette to assess the material by XRPD while the sample stirred at 25° C. for an hour; however, the material was of very low crystallinity. After the hour stirring at 25° C., the sample was placed at 5° C. for three days. After this time, another aliquot was removed by pipette for XRPD analysis. The remainder of the slurry was filtered under vacuum and dried at 25° C. under vacuum overnight to provide Compound 1, Form B.

Form C:

In a clean round bottom flask, 2.0 grams of Compound 1 were suspended in 25 ml of methanol and heated to 50° C. The warm solution of dissolved Compound 1 was filtered into a clean round bottom flask. The polished solution was allowed to cool to room temperature with magnetic stirring. The solution slowly became a slurry and was stirred for over 14 hours. The solids were filtered, washed with 5 mL of methanol, and dried on the filter for 20 hours, then at 50° C. in a vacuum-oven for 8 hours. Yield 1.4 grams of Form C (melting point=~132° C.).

Form D:

A dry mixture (ca. 5 mg of each component) was prepared using two of Form A, Form B, or Form C of Compound 1. A slurry made from amorphous Compound 1 in MIBK was filtered to obtain a saturated solution. Ten volumes (100 μl) of the saturated solution were added to the dry mixture to prepare a new slurry. The slurry was stored at 5° C. for three days before filtration under vacuum to provide Compound 1, Form D.

Form E:

Amorphous compound 1 (20 mg) was added to a vial, followed by seeds of Compound 1, Form C (ca. 5 mg). Ten volumes of toluene (200 μl) were added to the vial to prepare a slurry. The vial was sealed and matured (cycling between 50° C. and ambient temperature for four hours each) for one day. An aliquot was removed by pipette for analysis by XRPD, TGA, and DSC; data were consistent with Compound 1, Form E. However, this compound was found to have converted to Compound 1, Form A after standing at ambient temperature overnight and drying at 40° C. in vacuo for one day.

Form F:

In a clean 20 ml scintillation vial, 200 mgs of Compound 1 and 50 mgs of activated charcoal were suspended in 4 ml of methanol and heated to 50° C. The resulting mixture was stirred at 50° C. for 2.5 hours. The warm solution of dissolved Compound 1 was filtered though a syringe filter into a new, clean 20 ml vial, removing the charcoal. The polished solution was allowed to cool to room temperature. Without stirring, the solution was aged for over a week when some crystals were observed to have formed. After 6 more weeks the bottom of the vial was covered with large crystals. The crystals were maintained under the supersaturated methanol solution for analysis.

Example 2: X-Ray Powder Diffraction (XRPD)

X-Ray powder diffraction patterns were collected on a Bruker AXS C2 GADDS or Bruker AXS D8 diffractometer.

Bruker AXS C2 GADDS

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Gobel multilayer mirror coupled with a pinhole collimator of 0.3 mm. A weekly performance check is carried out using a certified standard NIST 1976 Corundum (flat plate). The beam divergence, i.e. the effective size of the X-ray beam on the sample, was approximately 4 mm. A θ-θ continuous scan mode was employed with a sample-detector distance of 20 cm which gives an effective 2θ range of 3.2°-29.7°. Typically the sample would be exposed to the X-ray beam for 120 seconds. The software used for data collection was GADDS for WNT 4.1.16 and the data were analysed and presented using Diffrac Plus EVA v11.0.0.2 or v13.0.0.2.

Ambient Conditions

Samples run under ambient conditions were prepared as flat plate specimens using powder as received without grinding. Approximately 1-2 mg of the sample was lightly pressed on a glass slide to obtain a flat surface.

Non-Ambient Conditions

Samples run under non-ambient conditions were mounted on a silicon wafer with heatconducting compound. The sample was then heated to the appropriate temperature at 10° C./min (unless otherwise stated) and subsequently held isothermally for 1 minute before data collection was initiated.

Bruker AXS D8 Advance

X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.5.0 and the data were analysed and presented using Diffrac Plus EVA v11.0.0.2 or v13.0.0.2. Samples were run under ambient conditions as flat plate specimens using powder as received. The sample was gently packed into a cavity cut into polished, zero-background (510) silicon wafer. The sample was rotated in its own plane during analysis. The details of the data collection are:

Angular range: 2 to 42° 2θ
Step size: 0.05° 2θ
Collection time: 0.5 s/step
XRPD on Form A The X-Ray powder diffraction for Form A is displayed in FIG. 1. Characteristic peaks include 5.7±0.10 2-Theta, 13.6±0.1° 2-Theta, 16.1±0.1° 2-Theta, 18.9±0.1° 2-Theta, 21.3±0.1 2-Theta, and 21.6±0.1° 2-Theta.

Crystallinity was unaffected after one week storage at 40° C./75% RH or after one week storage at 25° C./97% RH.

XRPD on Form B

The X-Ray powder diffraction for Form B is displayed in FIG. 5. Characteristic peaks include 5.2±0.10 2-Theta, 10.2±0.10 2-Theta, 16.5±0.10 2-Theta, 18.5±0.10 2-Theta, and 20.8±0.1° 2-Theta.

Crystallinity was unaffected after one week storage at 40° C./75% RH or after one week storage at 25° C./97% RH.

XRPD on Form C

The X-Ray powder diffraction for Form C is displayed in FIG. 9. Characteristic peaks include 7.0±0.1° 2-Theta, 14.0±0.1° 2-Theta, 15.7±0.1° 2-Theta, 18.2±0.1° 2-Theta, 19.1±0.1 2-Theta, 19.5±0.10 2-Theta, 20.3±0.10 2-Theta, 22.1±0.10 2-Theta, and 22.9±0.10 2-Theta.

Crystallinity was unaffected after one week storage at 40° C./75% RH or after one week storage at 25° C./97% RH.

XRPD on Form D

The X-Ray powder diffraction for Form D is displayed in FIG. 12. Characteristic peaks include 7.2±0.1° 2-Theta, 8.0±0.1° 2-Theta, 9.2±0.1° 2-Theta, 14.50.1° 2-Theta, 18.50.1° 2-Theta, 19.5±0.10 2-Theta, 20.7±0.10 2-Theta, 21.0±0.10 2-Theta, 21.9±0.10 2-Theta, and 22.4±0.10 2-Theta.

XRPD on Form E

The X-Ray powder diffraction for Form E is displayed in FIG. 14. Characteristic peaks include 7.8±0.1° 2-Theta, 8.8±0.1° 2-Theta, 16.1±0.1° 2-Theta, 18.1±0.1° 2-Theta, 19.3±0.1° 2-Theta, 19.5±0.10 2-Theta, 20.5±0.10 2-Theta, 21.6±0.10 2-Theta, and 25.2±0.10 2-Theta.

XRPD on Form F

A simulated XRPD pattern was generated for Form F. The XRPD simulated pattern was generated from the single crystal data obtained from Example 3 (cif file) using Mercury CSD v3.1 (C. F. Macrae et al. *J. Appl. Cryst.* (2006), 39-3, 453-457) (XRPD pattern settings: CuKα 1.54056; Start/End 2/43 2θ°; PWHW (2θ°) 0.1). The data was then saved as a raw file. To generate the 2θ°/Intensity (%) peak table the raw file was treated using Diffrac Plus EVA v. 15,0,0,0.

The X-Ray powder diffraction simulated pattern for Form F is displayed in FIG. 16. Characteristic peaks include 6.2±0.10 2-Theta, 10.1±0.10 2-Theta, 17.6±0.10 2-Theta, 18.6±0.10 2-Theta, 20.0±0.10° 2-Theta, 20.4±0.10° 2-Theta, 20.7±0.10° 2-Theta, 22.4±0.10° 2-Theta, 23.0±0.10° 2-Theta, 23.2±0.10° 2-Theta, 24.4±0.10° 2-Theta, 25.1±0.10° 2-Theta, 27.6±0.10° 2-Theta, 29.3±0.10 2-Theta, and 29.7±0.1° 2-Theta.

Example 3: Single Crystal X-Ray Diffraction

Single crystal X-ray diffraction data was collected and processed as follows:
Diffractometer SuperNova, Dual, Cu at zero, Atlas
Radiation source SuperNova (Cu) X-ray Source, CuKα
Data collection method omega scans
Theta range for data collection 9.11 to 74.49°
Index ranges −11≤h≤12, −12≤k≤12, −18≤l≤18
Reflections collected 22842
Independent reflections 9278 [R(int)=0.0407]
Coverage of independent reflections 99.4%
Variation in check reflections N/A
Absorption correction Semi-empirical from equivalents
Max. and min. transmission 1.00000 and 0.73583
Structure solution technique direct
Structure solution program SHELXS-97 (Sheldrick, 1990)
Refinement technique Full-matrix least-squares on $F^2$
Refinement program SHELXL-97 (Sheldrick, 1997)
Function minimized $\Sigma w(F_o^2-F_c^2)^2$
Data/restraints/parameters 9278/3/660
Goodness-of-fit on $F^2$ 1.004
$\Delta/\sigma_{max}$ 0.000
Final R indices
  9185 data; I>2σ(I) R1=0.0414, wR2=0.1144
  all data R1=0.0417, wR2=0.1149
Weighting scheme calc w=1/[σ² $(F_o^2)$+(0.0810P)²+0.2800P] where P=$(F_o^2+2F_c^2)$/3
Absolute structure parameter −0.01(13)
Extinction coefficient 0.0013(3)
Largest diff. peak and hole 0.320 and −0.285 eÅ⁻³

Form F was characterized by unit cell unit cell parameters approximately equal to the following at a temperature of approximately 100(2) K:

| Molecular formula | | | $C_{53}H_{60}N_{12}O_7$ | | |
|---|---|---|---|---|---|
| Molecular weight | | | 977.13 | | |
| Crystal system | | | Triclinic | | |
| Space group | P1 | a | 9.6332(3) Å | α | 105.762(3)° |
| | | b | 9.7536(4) Å | β | 95.132(2)° |
| | | c | 15.0592(4) Å | γ | 111.332(3)° |
| V | | | 1240.15(7) Å³ | | |
| Z | | | 1 | | |
| Density (calculated) | | | 1.308 Mg/m³ | | |
| Absorption coefficient | | | 0.726 mm⁻¹ | | |
| Wavelength | | | 1.54178 Å | | |
| F(000) | | | 518 | | |
| T | | | 100(2) K | | |

Example 4: Fourier Transform-Infra-Red (FTIR)

Data were collected on a Perkin-Elmer Spectrum One fitted with a universal Attenuated Total Reflectance (ATR) sampling accessory. The data were collected and analysed using Spectrum v5.0.1 software.

The infrared spectrum for Form A is displayed in FIG. 2. Characteristic peaks observed in the infrared spectrum for Form A include peaks at: 1584 cm⁻¹, 1240 cm⁻¹, 1147 cm⁻¹, 1134 cm⁻¹, 1099 cm⁻¹, 1067 cm⁻¹, 985 cm⁻¹, and 953 cm⁻¹.

The infrared spectrum for Form B is displayed in FIG. 6. Characteristic peaks observed in the infrared spectrum for Form B include peaks at: 1586 cm$^{-1}$, 1573 cm$^{-1}$, 1562 cm$^{-1}$, 1229 cm$^{-1}$, 1166 cm$^{-1}$, 1141 cm$^{-1}$, 1103 cm$^{-1}$, 1056 cm$^{-1}$, 1033 cm$^{-1}$, and 982 cm$^{-1}$.

Example 5: Differential Scanning Calorimetry (DSC) and Thermo-Gravimetric Analysis (TGA)

DSC data were collected on a TA Instruments Q2000 equipped with a 50 position autosampler. The calibration for thermal capacity was carried out using sapphire and the calibration for energy and temperature was carried out using certified indium. Typically 0.5-3 mg of each sample, in a pin-holed aluminium pan, was heated at 10° C./min from 25° C. to 300° C. A purge of dry nitrogen at 50 ml/min was maintained over the sample, unless otherwise stated. Modulated temperature DSC was carried out using an underlying heating rate of 2° C./min and temperature modulation parameters of ±0.318° C. (amplitude) every 60 seconds (period). The instrument control software was Advantage for Q Series v2.8.0.392 and Thermal Advantage v4.8.3 and the data were analysed using Universal Analysis v4.4A.

TGA data were collected on a TA Instruments Q500 TGA, equipped with a 16 position autosampler. The instrument was temperature calibrated using certified Alumel and Nickel. Typically 3-10 mg of each sample was loaded onto a pre-tared aluminium DSC pan and heated at 10° C./min from ambient temperature to 350° C. A nitrogen purge at 60 ml/min was maintained over the sample, unless otherwise stated. The instrument control software was Advantage for Q Series v2.8.0.392 and Thermal Advantage v4.8.3 and the data were analysed using Universal Analysis v4.4A.

Form A

Figure 4:
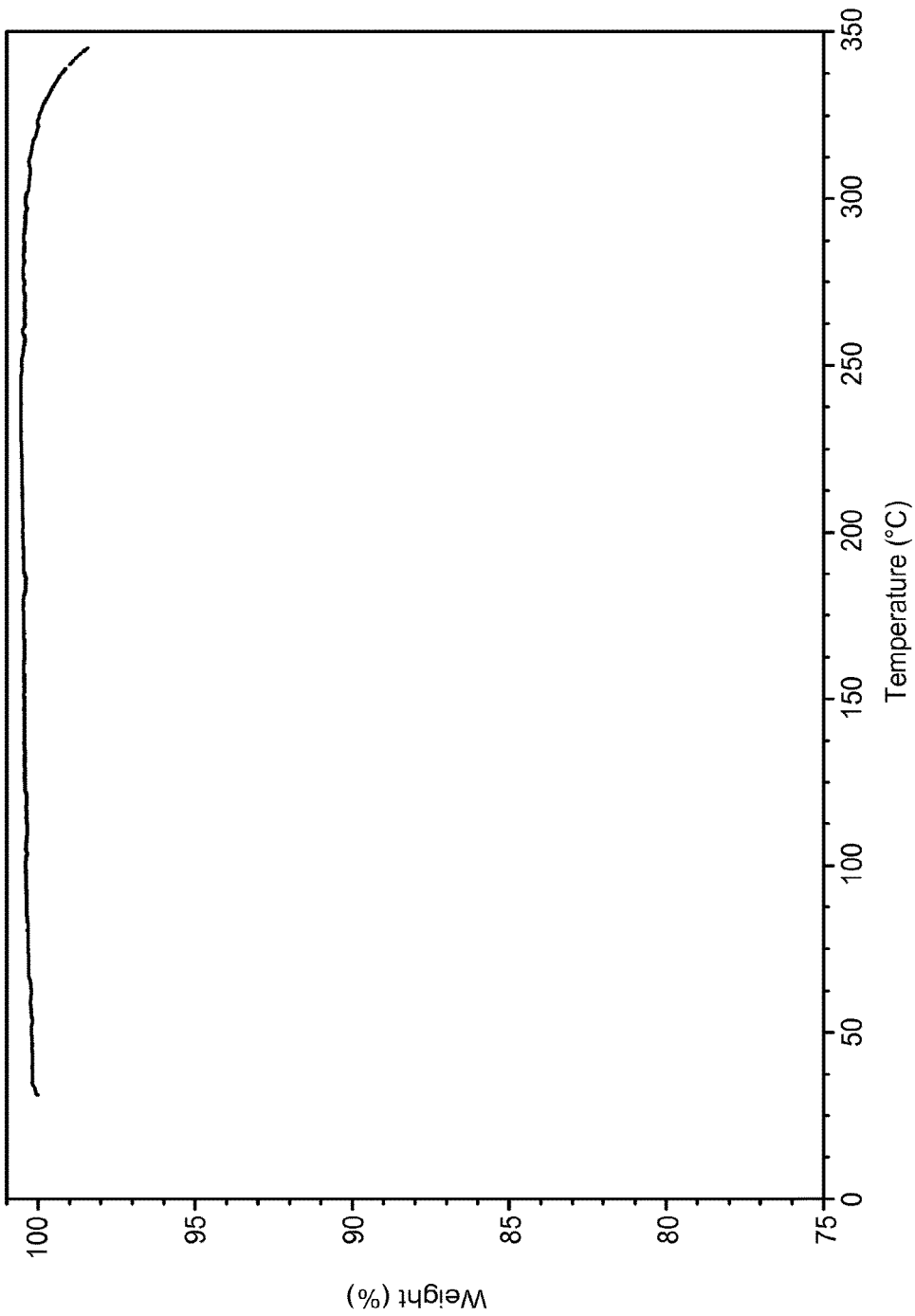
FIG. 4. Illustrates a thermo-gravimetric analysis (TGA) thermogram of Form A.

DSC and TGA thermograms for Form A are displayed in FIG. 3 and FIG. 4 respectively.

No weight loss was observed. Material is anhydrous.

In the DSC (rate of heating: 10° C./min or 20° C./min) an endotherm was observed having an onset at about 154° C. and a peak at about 157° C. An exothermic peak was observed at 159° C.

Form B

DSC and TGA thermograms for Form B are displayed in FIG. 7 and FIG. 8 respectively.

No weight loss was observed. Material is anhydrous.

In the DSC (rate of heating: 10° C./min or 20° C./min) an endotherm was observed having an onset at about 99-106° C. and a peak at about 115-118° C.

Form C

Figure 11:
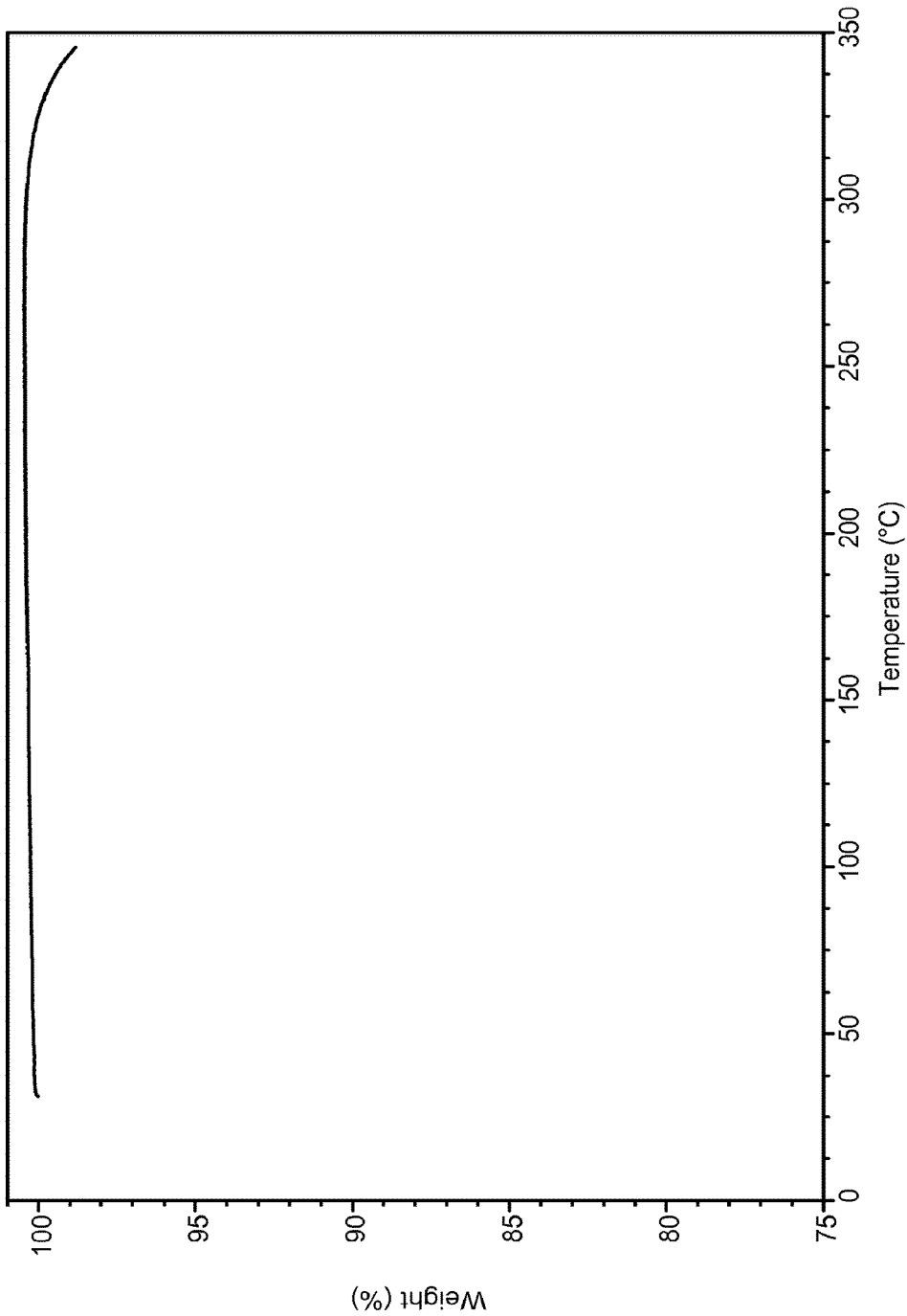
FIG. 11. Illustrates a thermo-gravimetric analysis (TGA) thermogram of Form C.

DSC and TGA thermograms for Form C are displayed in FIG. 10 and FIG. 11 respectively.

No weight loss was observed. Material is anhydrous.

In the DSC (rate of heating: 10° C./min or 20° C./min) an endotherm was observed having an onset at about 134-135° C. and a peak at about 137-139° C.

Form D

A TGA thermogram for Form D is displayed in FIG. 13.

Total weight loss of 16.6-17.8%, equivalent to about one mole of MIBK, was observed by TGA either as 1 step or as 2 steps.

Form E

DSC and TGA thermograms for Form E are displayed in FIG. 15.

A weight loss of 16.5% w/w was observed in TGA associated with 2 endothermic events in DSC recorded at 85° C. (onset) and 151° C. (onset) which could correspond to desolvation phenomena.

Example 6: Gravimetric Vapour Sorption (GVS)

Sorption isotherms were obtained using a SMS DVS Intrinsic moisture sorption analyser, controlled by DVS Intrinsic Control software v1.0.0.30. The sample temperature was maintained at 25° C. by the instrument controls. The humidity was controlled by mixing streams of dry and wet nitrogen, with a total flow rate of 200 ml/min The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg). Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range. Data analysis was undertaken in Microsoft Excel using DVS Analysis Suite v6.0.0.7. The sample was recovered after completion of the isotherm and re-analysed by XRPD.

TABLE 1

| Method Parameters for SMS DVS Intrinsic Experiments | |
| --- | --- |
| Parameters | Values |
| Adsorption - Scan 1 | 40-90 |
| Desorption/Adsorption - Scan 2 | 90-0, 0-40 |
| Intervals (% RH) | 10 |
| Number of Scans | 2 |
| Flow rate (ml/min) | 200 |
| Temperature (° C.) | 25 |
| Stability (° C./min) | 0.2 |
| Sorption Time (hours) | 6 hour time out |

Form A

The mass change was <0.3% w/w between 0-90% RH. The material is not hygroscopic. No significant changes were observed in the XRPD after GVS analysis.

Form B

The mass change was 2.3% w/w between 0-90% RH. No hysteresis was observed. No significant changes were observed in the XRPD after GVS analysis.

Example 7: Thermodynamic Aqueous Solubility

Aqueous solubility was determined by suspending sufficient compound in water to give a maximum final concentration of ≥10 mg/ml of the parent free-form of the compound. The suspension was equilibrated at 25° C. for 24 hours then the pH was measured. The suspension was then filtered through a glass fibre C filter. The filtrate was then diluted by an appropriate factor e.g. 101. Quantitation was by HPLC with reference to a standard solution of approximately 0.25 mg/ml in DMSO. Different volumes of the standard, diluted and undiluted sample solutions were injected. The solubility was calculated using the peak areas determined by integration of the peak found at the same retention time as the principal peak in the standard injection.

TABLE 2

| HPLC Method Parameters for Solubility Measurements | |
| --- | --- |
| Type of method: | Reverse phase with gradient elution |
| Column: | Phenomenex Luna, C18 (2) |
| | 5 μm 50 × 4.6 mm |
| Column Temperature (° C.): | 25 |
| Standard Injections (μl): | 1, 2, 3, 5, 7, 10 |
| Test Injections (μl): | 1, 2, 3, 10, 20, 50 |

TABLE 2-continued

| | |
|---|---|
| Detection: Wavelength, Bandwidth (nm) | 260, 80 |
| Flow Rate (ml/min): | 2 |
| Phase A: | 0.1% TFA in water |
| Phase B: | 0.085% TFA in acetonitrile |

| Timetable: | Time (mm) | % Phase A | % Phase B |
|---|---|---|---|
| | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

Analysis was performed on an Agilent HP1100 series system equipped with a diode array detector and using ChemStation software vB.02.01-SR1.

The solubility of Form A in aqueous solution at different pH is presented in Table 3.

TABLE 3

Form A Solubility in Aqueous Solution at Different pH

| pH | Conc. Found (mg/mL) |
|---|---|
| 1.2 | 1.3 |
| 1.64 | 1.07 |
| 1.95 | 0.82 |
| 3 | 0.10 |
| 4 | 0.022 |
| 5 | 0.017 |
| 6 | 0.015 |
| 8 | 0.013 |
| 9 | 0.020 |
| 10 | 0.010 |

The thermodynamic aqueous solubility of Form B at pH of 7.42 was determined to be 0.0096 mg/ml.

Example 8: Chemical Purity Determination

HPLC analysis performed on an Agilent HP1100/1200 system equipped with a diode array detector and using Chemstation software using the method detailed below:

TABLE 4

Method Parameters

| | |
|---|---|
| Type of method: | Reverse phase with gradient elution |
| Test sample make-up: | ~0.1 mg/ml in 60:40 v/v H₂O:ACN |
| Column: | Gemini-NX C18, 4.6 × 150 mm, 3 µm |
| Column temperature (° C.): | 40 |
| Injection (µl): | 100 |
| Detection Wavelength, Bandwidth (nm) | 260, scan from 210 to 500 nm |
| Flow Rate (ml/min): | 1.5 |
| Phase A: | 0.1% TFA in water |
| Phase B: | 0.1% TFA in acetonitrile |

| Timetable: | Time (min) | % Phase A | % Phase B |
|---|---|---|---|
| | 0 | 75 | 25 |
| | 10 | 70 | 30 |
| | 30 | 65 | 35 |
| | 45 | 35 | 65 |
| | 46 | 10 | 90 |
| | 50 | 10 | 90 |
| | 51 | 75 | 25 |

TABLE 4-continued

| | | | |
|---|---|---|---|
| | 60 | 75 | 25 |
| Retention time: | ~20 min | | |
| Needle wash: | methanol:water (8:2) | | |

In some embodiments, Form A is greater than 95% pure by HPLC analysis. In some embodiments, Form A is greater than 96% pure by HPLC analysis. In some embodiments, Form A is greater than 97% pure by HPLC analysis. In some embodiments, Form A is greater than 98% pure by HPLC analysis. In some embodiments, Form A is greater than 99% pure by HPLC analysis. In some embodiments, Form A is 99.8% pure by HPLC analysis.

In some embodiments, Form B is greater than 95% pure by HPLC analysis. In some embodiments, Form B is greater than 96% pure by HPLC analysis. In some embodiments, Form B is greater than 97% pure by HPLC analysis. In some embodiments, Form B is greater than 98% pure by HPLC analysis. In some embodiments, Form B is greater than 99% pure by HPLC analysis. In some embodiments, Form B is 97.8% pure by HPLC analysis. In some embodiments, Form B is 99.8% pure by HPLC analysis.

In some embodiments, Form C is greater than 95% pure by HPLC analysis. In some embodiments, Form C is greater than 96% pure by HPLC analysis. In some embodiments, Form C is greater than 97% pure by HPLC analysis. In some embodiments, Form C is greater than 98% pure by HPLC analysis. In some embodiments, Form C is greater than 99% pure by HPLC analysis. In some embodiments, Form C is 99.4% pure by HPLC analysis.

Example 9: Chiral Purity Determination

Chiral purity of Compound 1 was determined by using a Lux Cellulose-1 chiral column by normal phase HPLC. The mobile phase is composed of 20% isopropyl alcohol and 80% hexanes. The enantiomers of 1-(3-(4-amino-3-(4-phenoxyphenyl)-1H-pyrazolo[3,4-d]pyrimidin-1-yl)piperidin-1-yl)prop-2-en-1-one are detected at 260 nm. In one embodiment, Compound 1 is dissolved in a mixture of Hexanes:IPA=(7:3) to obtain a concentration of approximately 0.2 mg/mL and the chiral purity of the sample is analyzed. The content of the R enantiomer is determined by peak area normalization of the enantiomer peaks and is expressed in weight to weight percent. In some embodiments, a sample of Compound 1 includes less than 5.0%, less than 4.0%, less than 3.0%, less than 2.0%, or less than 1.0%, of the (S)-isomer. In some embodiments, a sample of Compound 1 includes less than 1.0% of the (S)-isomer.

Solid Oral Dosage Forms

In some embodiments, crystalline 1-((R)-3-(4-amino-3-(4-phenoxyphenyl)-1H-pyrazolo[3,4-d]pyrimidin-1-yl)piperidin-1-yl)prop-2-en-1-one is formulated into a solid oral dosage form. In some embodiments, the crystallinity of 1-((R)-3-(4-amino-3-(4-phenoxyphenyl)-1H-pyrazolo[3,4-d]pyrimidin-1-yl)piperidin-1-yl)prop-2-en-1-one is maintained in the solid oral dosage form. In some embodiments, crystalline 1-((R)-3-(4-amino-3-(4-phenoxyphenyl)-1H-pyrazolo[3,4-d]pyrimidin-1-yl)piperidin-1-yl)prop-2-en-1-one is formulated into tablets. In some embodiments, crystalline 1-((R)-3-(4-amino-3-(4-phenoxyphenyl)-1H-pyrazolo[3,4-d]pyrimidin-1-yl)piperidin-1-yl)prop-2-en-1-one is formulated into pills. In some embodiments, crystalline 1-((R)-3-(4-amino-3-(4-phenoxyphenyl)-1H-pyrazolo[3,4-d]pyrimidin-1-yl)piperidin-1-yl)prop-2-en-1- one is formulated into capsules. In some embodiments, crystalline 1-((R)-3-(4-amino-3-(4-phenoxyphenyl)-1H-pyrazolo[3,4-d]pyrimidin-1-yl)piperidin-1-yl)prop-2-en-1-one is placed into capsules without excipients or with excipients. In any of these embodiments, crystalline 1-((R)-3-(4-amino-3-(4-phenoxyphenyl)-1H-pyrazolo[3,4-d]pyrimidin-1-yl)piperidin-1-yl)prop-2-en-1-one is Form A. In any of these embodiments, crystalline 1-((R)-3-(4-amino-3-(4-phenoxyphenyl)-1H-pyrazolo[3,4-d]pyrimidin-1-yl)piperidin-1-yl)prop-2-en-1-one is Form B. In any of these embodiments, crystalline 1-((R)-3-(4-amino-3-(4-phenoxyphenyl)-1H-pyrazolo[3,4-d]pyrimidin-1-yl)piperidin-1-yl)prop-2-en-1-one is Form C. In any of these embodiments, crystalline 1-((R)-3-(4-amino-3-(4-phenoxyphenyl)-1H-pyrazolo[3,4-d]pyrimidin-1-yl)piperidin-1-yl)prop-2-en-1-one is Form D. In any of these embodiments, crystalline 1-((R)-3-(4-amino-3-(4-phenoxyphenyl)-1H-pyrazolo[3,4-d]pyrimidin-1-yl)piperidin-1-yl)prop-2-en-1-one is Form E. In any of these embodiments, crystalline 1-((R)-3-(4-amino-3-(4-phenoxyphenyl)-1H-pyrazolo[3,4-d]pyrimidin-1-yl)piperidin-1-yl)prop-2-en-1-one is Form F. In any of these embodiments, crystalline 1-((R)-3-(4-amino-3-(4-phenoxyphenyl)-1H-pyrazolo[3,4-d]pyrimidin-1-yl)piperidin-1-yl)prop-2-en-1-one is a mixture of two or more crystalline forms selected from the group consisting of Form A, Form B, Form C, Form D, Form E, and Form F.

Example 10: Capsule Formulations

In one embodiment, capsule formulations of Compound 1 for administration to humans is prepared with the following ingredients:

TABLE 5

Capsule Formulations

| Component | 40 mg Capsule | | 140 mg Capsule | | 140 mg Capsule | | 200 mg Capsule | |
|---|---|---|---|---|---|---|---|---|
| | w/w % | mg/capsule | w/w % | mg/capsule | w/w % | mg/capsule | w/w % | mg/capsule |
| crystalline Compound 1 | 29.6 | 40.0 | 60.9 | 140.0 | 42.4 | 140.0 | 74.1 | 200.0 |
| Microcrystalline cellulose NF | 57.4 | 77.5 | 23.0 | 53.0 | 45.9 | 151.4 | 8.5 | 23.0 |
| Croscarmellose sodium NF | 10.0 | 13.5 | 10.0 | 23.0 | 7.0 | 23.0 | 10.0 | 27.0 |
| Sodium lauryl sulfate NF | 3.0 | 4.0 | 6.1 | 14.0 | 4.2 | 14.0 | 7.4 | 20.0 |
| Magnesium stearate NF | NA | NA | NA | NA | 0.5 | 1.6 | NA | NA |

In some embodiments, the manufacturing process includes the following steps: weigh the indicated amount of the components, mix together and add into an appropriate size capsule, and close capsule. In some embodiments, the capsules are stored at room temperature for an extended period of time until they are used.

Example 11: Immediate Release Tablets

In some embodiments, tablets are prepared with the components set forth in Table 10.

TABLE 6

Components of Tablet Formulation

| Ingredient | Range |
|---|---|
| crystalline Compound 1 | 5% to 50% |
| Hypromellose | 2% to 10% |
| Croscarmellose sodium | 0% to 15% |
| Microcrystalline cellulose | 5% to 50% |
| Lactose | 10% to 75% |
| Magnesium stearate | 0.25% to 2.5% |
| Total | Tablet weight range: 300 mg to 1000 mg |

Manufacturing process will typically be granulation (dry, wet or melt) or direct compression.

Example 12: Safety and Tolerability Study of Compound 1 in Chronic Lymphocytic Leukemia Purpose: The purpose of this study is to establish the safety and optimal dose of orally administered Compound 1 (420 mg/day) in patients with B-cell chronic lymphocytic leukemia/small lymphocytic lymphoma/diffuse well-differentiated lymphocytic lymphoma.

Primary Outcome Measures: Safety and tolerability of Compound 1 (frequency, severity, and relatedness of adverse events).

Secondary Outcome Measures: Pharmacokinetic/Pharmacodynamic assessments. Tumor response-overall response rate as defined by recent guidelines on CLL and SLL (B cell lymphoma) and duration of response.

Eligibility: 18 Years and older; both genders are eligible.

Inclusion Criteria: 1. For treatment-naive group only: Men and women≥65 years of age with confirmed diagnosis of CLL/SLL, who require treatment per NCI or International Working Group guidelines 11-14. 2. For relapsed/refractory group only: Men and women≥18 years of age with a confirmed diagnosis of relapsed/refractory CLL/SLL unresponsive to therapy (ie, failed ≥2 previous treatments for CLL/SLL and at least 1 regimen had to have had a purine analog [eg, fludarabine] for subjects with CLL). 3. Body weight≥40 kg. 4. ECOG performance status of ≤2. 5. Agreement to use contraception during the study and for 30 days after the last dose of study drug if sexually active and able to bear children. 6. Willing and able to participate in all required evaluations and procedures in this study protocol including swallowing capsules without difficulty. 7. Ability to understand the purpose and risks of the study and provide signed and dated informed consent and authorization to use protected health information (in accordance with national and local subject privacy regulations).

Exclusion Criteria: 1. A life-threatening illness, medical condition or organ system dysfunction which, in the investigator's opinion, could compromise the subject's safety, interfere with the absorption or metabolism of Compound 1 PO, or put the study outcomes at undue risk. 2. Any immunotherapy, chemotherapy, radiotherapy, or experimental therapy within 4 weeks before first dose of study drug (corticosteroids for disease-related symptoms allowed but require 1-week washout before study drug administration). 3. Central nervous system (CNS) involvement by lymphoma. 4. Major surgery within 4 weeks before first dose of study drug. 5. Creatinine>1.5×institutional upper limit of normal (ULN); total bilirubin>1.5×ULN (unless due to Gilbert's disease); and aspartate aminotransferase (AST) or alanine aminotransferase (ALT)>2.5×ULN unless disease related. 6. Concomitant use of medicines known to cause QT prolongation or torsades de pointes. 7. Significant screening electrocardiogram (ECG) abnormalities including left bundle branch block, 2nd degree AV block type II, 3rd degree block, bradycardia, and QTc>470 msec. 8. Lactating or pregnant.

Example 13: Safety and Efficacy of Compound 1 in Subjects with Relapsed/Refractory Mantle Cell Lymphoma (MCL)

The primary objective of this trial is to evaluate the efficacy of Compound 1 in relapsed/refractory subjects with Mantle Cell Lymphoma (MCL). The secondary objective is to evaluate the safety of a fixed daily dosing regimen of Compound 1 (560 mg/day in the form of capsules) in this population.

Primary Outcome Measures: To measure the number of participants with a response to Compound 1.

Secondary Outcome Measures: To measure the number of participants with adverse events as a measure of safety and tolerability. To measure pharmacokinetics to assist in determining how the body responds to the study drug. Patient reported outcomes (to measure the number of participants reported outcomes in determining the health related quality of life).

Eligibility: 18 Years and older; both genders are eligible.

Inclusion Criteria: Men and women≥18 years of age. ECOG performance status of ≤2. Pathologically confirmed MCL, with documentation of either overexpression of cyclin D1 or t(11;14), and measurable disease on cross sectional imaging that is ≥2 cm in the longest diameter and measurable in 2 perpendicular dimensions. Documented failure to achieve at least partial response (PR) with, or documented disease progression disease after, the most recent treatment regimen. At least 1, but no more than 5, prior treatment regimens for MCL (Note: Subjects having received ≥2 cycles of prior treatment with bortezomib, either as a single agent or as part of a combination therapy regimen, will be considered to be bortezomib-exposed.). Willing and able to participate in all required evaluations and procedures in this study protocol including swallowing capsules without difficulty. Ability to understand the purpose and risks of the study and provide signed and dated informed consent and authorization to use protected health information (in accordance with national and local subject privacy regulations).

Major exclusion criteria: Prior chemotherapy within 3 weeks, nitrosoureas within 6 weeks, therapeutic anticancer antibodies within 4 weeks, radio- or toxin-immunoconjugates within 10 weeks, radiation therapy within 3 weeks, or major surgery within 2 weeks of first dose of study drug. Any life-threatening illness, medical condition or organ system dysfunction which, in the investigator's opinion, could compromise the subject's safety, interfere with the absorption or metabolism of Compound 1 capsules, or put the study outcomes at undue risk. Clinically significant cardiovascular disease such as uncontrolled or symptomatic arrhythmias, congestive heart failure, or myocardial infarction within 6 months of screening, or any Class 3 or 4 cardiac disease as defined by the New York Heart Association Functional Classification. Malabsorption syndrome, disease significantly affecting gastrointestinal function, or resection of the stomach or small bowel or ulcerative colitis, symptomatic inflammatory bowel disease, or partial or complete bowel obstruction. Any of the following laboratory abnormalities: 1. Absolute neutrophil count (ANC)<750 cells/mm3 (0.75×109/L) unless there is documented bone marrow involvement. 2. Platelet count<50,000 cells/mm3 (50×109/L) independent of transfusion support unless there is documented bone marrow involvement. 3. Serum aspartate transaminase (AST/SGOT) or alanine transaminase (ALT/SGPT)≥3.0×upper limit of normal (ULN). 4. Creatinine>2.0×ULN.

Example 14: Phase 2 Study of the Combination of Compound 1 and Rituximab in High-Risk Chronic Lymphocytic Leukemia and Small Lymphocytic Lymphoma Patients Purpose: The goal of this clinical research study is to learn if Compound 1 combined with rituximab can help to control chronic lymphocytic leukemia (CLL) and small lymphocytic lymphoma (SLL). The safety of this combination will also be studied.

Rituximab (375 mg/m$^2$) given intravenously (IV) on Day 1, Day 8, Day 15, and Day 22, then continued once every 4 weeks only on Days 1 during cycles 2-6. Compound 1 started on Day 2 of cycle 1 at a dose of 420 mg (3×140-mg capsules) orally daily and will be continued daily.

Primary Outcome Measures: Progression free survival (PFS) [Time Frame: 3 months]—progression free survival defined as the time interval from treatment to progressive disease or death, whichever happens earlier. Patients in complete remission (CR), partial remission (PR) or stable disease (SD) are all counted as progression-free. Survival or times to progression functions estimated using the Kaplan-Meier method.

Secondary Outcome Measures: Toxicity [Time Frame: 3 months]—toxicity reported by type, frequency and severity. Worst toxicity grades per patient tabulated for selected adverse events and laboratory measurements. Toxicity (grade 3 or 4) monitored based on the Bayesian model (beta-binomial) by assuming a priori probability of toxicity following beta(1,1).

Eligibility: 18 Years and older; both genders are eligible.

Inclusion Criteria: 1. Patients must have a diagnosis of high-risk CLL/SLL and be previously treated with up to 3 lines of prior therapy. High-risk CLL and high-risk SLL is defined by the presence of a 17p deletion or 11q deletion or TP53 mutation. Any CLL and SLL patient who has a short remission duration of less than 3 years after prior first-line chemo-immunotherapy, such as the FCR regimen, also fulfills criteria of high-risk CLL/SLL, regardless of the presence or absence of cytogenetic abnormalities. 2. CLL and SLL patients with 17p deletion or TP53 mutation will not be required to have received any prior therapy, given the poor outcome of CLL/SLL patients to standard frontline chemo-immunotherapy, such patients will be eligible if they are untreated or if they have received up to 3 lines of prior therapy. 3. Patients must have an indication for treatment by 2008 IWCLL Criteria. 4. Patients age>18 years at the time of signing informed consent. Understand and voluntarily sign an informed consent. Be able to comply with study procedures and follow-up examinations. 5. ECOG/WHO performance status of 0-1. 6. Patients of childbearing potential must be willing to practice highly effective birth control (e.g., condoms, implants, injectables, combined oral contraceptives, some intrauterine devices [IUDs], sexual abstinence, or sterilized partner) during the study and for 30 days after the last dose of study drug. Women of childbearing potential include any female who has experienced menarche and who has not undergone successful surgical sterilization (hysterectomy, bilateral tubal ligation, or bilateral oophorectomy) or is not postmenopausal. Post menopause is defined as follows: Amenorrhea>/=12 consecutive months without another cause and a documented serum follicle stimulating hormone (FSH) level>35 mIU/mL; a male of childbearing potential is any male that has not been surgically sterilized. 7. Adequate renal and hepatic function as indicated by all of the following: Total bilirubin</=1.5×institutional Upper Limit of Normal (ULN) except for patients with bilirubin elevation due to Gilbert's disease who will be allowed to participate; an ALT</=2.5×ULN; and an estimated creatinine clearance (CrCl) of >30 mL/min, as calculated by the Cockroft-Gault equation unless disease related. 8. Free of prior malignancies for 3 years with exception of currently treated basal cell, squamous cell carcinoma of the skin, or carcinoma in situ of the cervix or breast. 9. A urine pregnancy test (within 7 days of Day 1) is required for women with childbearing potential Exclusion Criteria: 1. Pregnant or breast-feeding females. 2. Treatment including chemotherapy, chemo-immunotherapy, monoclonal antibody therapy, radiotherapy, high-dose corticosteroid therapy (more than 60 mg Prednisone or equivalent daily), or immunotherapy within 21 days prior to enrollment or concurrent with this trial. 3. Investigational agent received within 30 days prior to the first dose of study drug or have previously taken Compound 1. If received any investigational agent prior to this time point, drug-related toxicities must have recovered to Grade 1 or less prior to first dose of study drug. 4. Systemic fungal, bacterial, viral, or other infection not controlled (defined as exhibiting ongoing signs/symptoms related to the infection and without improvement, despite appropriate antibiotics or other treatment). 5. Patients with uncontrolled Autoimmune Hemolytic Anemia (AIHA) or autoimmune thrombocytopenia (ITP). 6. Patients with severe hematopoietic insufficiency, as defined by an absolute neutrophil count of less than 500/micro-L and/or a platelet count of less than 30,000/micro-L at time of screening for this protocol. 7. Any other severe concurrent disease, or have a history of serious organ dysfunction or disease involving the heart, kidney, liver or other organ system that may place the patient at undue risk to undergo therapy with Compound 1 and rituximab. 8. Significant cardiovascular disease such as uncontrolled or symptomatic arrhythmias, congestive heart failure, or myocardial infarction within 6 months of screening, or any Class 3 or 4 cardiac disease as defined by the New York Heart Association Functional Classification. 9. Significant screening ECG abnormalities including left bundle branch block, 2nd degree AV block type II, 3rd degree block, bradycardia, and QTc>470 msec. 10. Any serious medical condition, laboratory abnormality, or psychiatric illness that places the subject at unacceptable risk if he/she were to participate in the study. 11. History of stroke or cerebral hemorrhage within 6 months. 12. Evidence of bleeding diathesis or coagulopathy. 13. Major surgical procedure, open biopsy, or significant traumatic injury within 28 days prior to Day 1, anticipation of need for major surgical procedure during the course of the study. 14. Minor surgical procedures, fine needle aspirations or core biopsies within 7 days prior to Day 1. Bone marrow aspiration and/or biopsy are allowed. 15. Serious, non-healing wound, ulcer, or bone fracture. 16. Treatment with Coumadin. Patients who recently received Coumadin must be off Coumadin for at least 7 days prior to start of the study. 17. Any chemotherapy (e.g., bendamustine, cyclophosphamide, pentostatin, or fludarabine), immunotherapy (e.g., alemtuzumab, or ofatumumab), bone marrow transplant, experimental therapy, or radiotherapy is prohibited during therapy on this study. 18. Use of medications known to prolong QTc interval or that may be associated with Torsades de Pointes (refer to Appendix F) are prohibited within 7 days of starting study drug and during study-drug treatment.

The examples and embodiments described herein are illustrative and various modifications or changes suggested to persons skilled in the art are to be included within this disclosure. As will be appreciated by those skilled in the art, the specific components listed in the above examples may be replaced with other functionally equivalent components, e.g., diluents, binders, lubricants, fillers, and the like.

What is claimed is:

1. A crystalline form of 1-((R)-3-(4-amino-3-(4-phenoxyphenyl)-1H-pyrazolo[3,4-d]pyrimidin-1-yl)piperidin-1-yl) prop-2-en-1-one that has an X-ray powder diffraction (XRPD) pattern comprising 2-Theta peaks at about 16.1°, about 18.9°, and about 21.6°.

2. The crystalline form of claim 1, wherein the crystalline form is unsolvated.

3. A pharmaceutical formulation comprising the crystalline form of claim 1 and at least one pharmaceutically acceptable ingredient.

4. The pharmaceutical formulation of claim 3, wherein the crystalline form is unsolvated.

* * * * *